(12) United States Patent
Kobayashi et al.

(10) Patent No.: US 8,492,007 B2
(45) Date of Patent: Jul. 23, 2013

(54) METAL COMPLEX AND ORGANIC ELECTROLUMINESCENT DEVICE

(75) Inventors: Satoshi Kobayashi, Tsukuba (JP); Shuji Doi, Tsukuba (JP); Satoshi Mikami, Tsukuba (JP)

(73) Assignee: Sumitomo Chemical Company, Osaka (JP)

( * ) Notice: Subject to any disclaimer, the term of this patent is extended or adjusted under 35 U.S.C. 154(b) by 0 days.

(21) Appl. No.: 13/116,480

(22) Filed: May 26, 2011

(65) Prior Publication Data

US 2011/0227050 A1 Sep. 22, 2011

Related U.S. Application Data

(62) Division of application No. 10/508,861, filed as application No. PCT/JP03/03494 on Mar. 24, 2003, now Pat. No. 8,003,226.

(30) Foreign Application Priority Data

Mar. 26, 2002 (JP) ................. 2002-086173
Mar. 26, 2002 (JP) ................. 2002-086174

(51) Int. Cl.
*H01L 51/54* (2006.01)
*C09K 11/06* (2006.01)

(52) U.S. Cl.
USPC .... 428/690; 428/917; 313/504; 257/E51.028; 257/E51.036; 257/E51.044; 528/9; 528/394; 528/395; 528/423

(58) Field of Classification Search
None
See application file for complete search history.

(56) References Cited

U.S. PATENT DOCUMENTS

| 6,953,628 | B2 | 10/2005 | Kamatani et al. |
| 7,094,897 | B2 | 8/2006 | Stossel et al. |
| 2003/0224208 | A1 | 12/2003 | Kamatani et al. |
| 2004/0247934 | A1 | 12/2004 | Takeuchi et al. |
| 2005/0116622 | A1 | 6/2005 | Lo et al. |

FOREIGN PATENT DOCUMENTS

| EP | 1245659 | A1 | 10/2002 |
| JP | 2001-257076 | A | 9/2001 |
| JP | 2003-119179 | A | 4/2003 |
| JP | 2003-231692 | A | 8/2003 |
| JP | 2003-277444 | A | 10/2003 |
| JP | 2004-002755 | A | 1/2004 |
| WO | 00/44851 | A2 | 8/2000 |
| WO | 02/081488 | A1 | 10/2002 |
| WO | 03/001616 | A2 | 1/2003 |
| WO | 03/079736 | A1 | 9/2003 |

OTHER PUBLICATIONS

Quidan Ling et al., "PL and EL properties of a novel Eu-containing copolymer", Thin Solid Films, vol. 417, No. 1-2, 2002, pp. 127-131.
Wai-yeung Wong et al., "Synthesis and Electronic Properties of New Photoluminescent Platinum-Containing Polyynes with 9,9-Dihexylfluorene and 9-Butylcarbazole Units", Macromolecules, vol. 35, No. 9, 2002, pp. 3506-3513.
Quidan Ling et al., "A novel high photoluminescence efficiency polymer incorporated with pendant europium complexes", Polymer, vol. 42, No. 10, 2001, pp. 4605-4610.
M.J. Yang et al., "Eu complex-based multiple-quantum-well electroluminescent devices as voltage indicators", Materials Science and Engineering B, vol. B85, No. 2-3, 2001, pp. 100-103.
Mathew R. Robinson et al., "Synthesis morphology and optoelectronic properties of tris [(N-ethylcarbazolyl)(3',5'-hexyloxybenzoyl)methane(phenanthroline)-europium", Chemical Communications, No. 17, 2000, pp. 1645-1646.
M.A. Baldo, et al., "Very high-efficiency green organic light-emitting devices based on electrophosphorescence", vol. 75, No. 1, Applied Physics Letters, Jul. 5, 1999, pp. 4-6.
M.A. Baldo, et al., "Highly efficient phosphorescent emission from organic electroluminescent devices", Nature, Vo. 395, Sep. 10, 1998, pp. 151-154.
Takeshi Sano, et al., "Novel Europium Complex fo electrolminescent devices with sharp red emission", Jpn. J. Appl. Phys., vol. 34 (1995), pt. 1, No. 4A, pp. 1883-1887.

*Primary Examiner* — Marie R. Yamnitzky
(74) *Attorney, Agent, or Firm* — Sughrue Mion, PLLC

(57) ABSTRACT

A metal complex which has a metal complex structure showing light emission from triplet excited state, and has a monovalent group derived from carbazole, and a light-emitting device using said metal complex.

5 Claims, No Drawings

METAL COMPLEX AND ORGANIC ELECTROLUMINESCENT DEVICE

CROSS REFERENCE TO RELATED APPLICATIONS

This application is a Divisional of pending prior application Ser. No. 10/508,861 filed Sep. 24, 2004, which is a 371 application of PCT/JP03/03494 filed Mar. 24, 2003, which claims benefit of priority from Japanese patent application No. 2002-086173 filed Mar. 26, 2002 and Japanese patent application No. 2002-086174 filed Mar. 26, 2002. The entire disclosures of the prior applications are incorporated by reference herein.

TECHNICAL FIELD

The present invention relates to a new metal complex, and a light-emitting device using said metal complex as a light-emitting substance.

BACKGROUND ART

As the light-emitting material having phosphorescence in visible region used for a light emitting layer of light-emitting device, devices using a metal complex (hereafter may be referred to as triplet light-emitting complex) showing light emission from triplet excited state have been known.

As the triplet light-emitting complex, for example, Ir(ppy)3 which includes iridium as the central metal, (Appl. Phys. Lett., 75, 4 (1999)), PtOEP which includes platinum as the central metal (Nature, 395, 151 (1998)), Eu(TTA)3-phen which includes europium as the central metal (Jpn. J. Appl. Phys., 34, 1883 (1995)) are known.

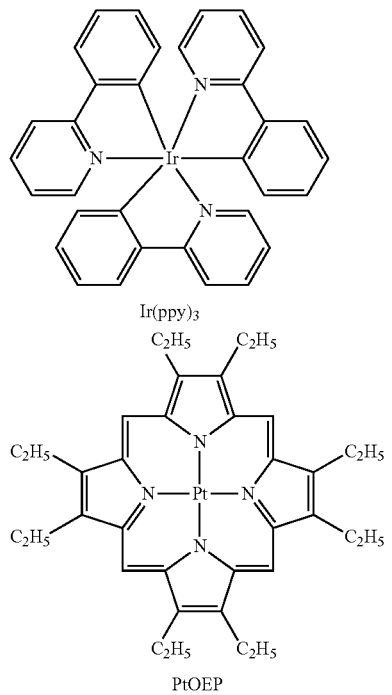

Ir(ppy)3

PtOEP

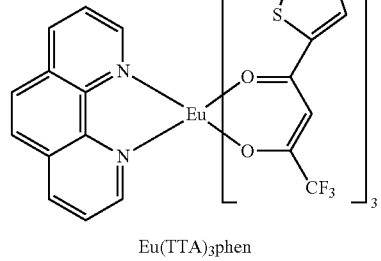

Eu(TTA)3phen

However, for forming a light emitting layer using the above well-known triplet light-emitting complexes, only the methods, such as vacuum-depositing method, are applicable, and it has been difficult to form a light emitting layer by coating method.

DISCLOSURE OF THE INVENTION

The object of the present invention is to provide a metal complex having phosphorescence in visible region, which has more excellent light emitting efficiency than the above-mentioned light-emitting materials. Moreover, the object of the present invention is to provide a new metal complex which has a triplet light-emitting complex structure in the molecule, and can be used for forming a light emitting layer by coating method, and to provide a light-emitting device using said complex.

That is, the present invention provides a metal complex which has a monovalent group having a metal complex structure which shows light emission from triplet excited state, and represented by the following formula (1) or (2). Said complex can form an efficient light emitting layer by coating method.

(1)

(In formula (1), A is a single bond or a divalent group derived from conjugate system. $R^1$ and $R^2$ each independently represent a halogen atom, alkyl group, alkoxy group, alkylthio group, alkylamino group, alkylsilyl group, aryl group, aryloxy group, arylthio group, arylamino group, arylsilyl group, arylalkyl group, arylalkoxy group, arylalkylthio group, arylalkylamino group, arylalkyl silyl group, acyl group, acyloxy group, imino group, amide group, arylalkenyl group, arylalkynyl group, cyano group, or a monovalent heterocyclic group. $R^3$ represents alkyl group, aryl group, arylalkyl group, arylalkenyl group, arylalkynyl group, or a monovalent heterocyclic group. a represents an integer of 0 to 3. b represents an integer of 0 to 4. When a is two or more, a plurality of $R^1$s may be the same or different. When b is two or more, a plurality of $R^2$s may be the same or different.)

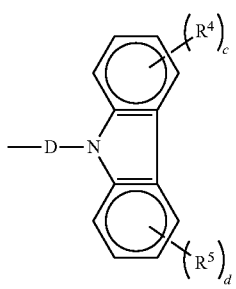
(2)

(In formula (2), D is a single bond or a divalent group derived from conjugate system. $R^4$ and $R^5$ each independently represent a halogen atom, alkyl group, alkoxy group, alkylthio group, alkylamino group, alkylsilyl group, aryl group, aryloxy group, arylthio group, arylamino group, arylsilyl group, arylalkyl group, arylalkoxy group, arylalkylthio group, arylalkyl amino group, arylalkyl silyl group, acyl group, acyloxy group, imino group, amide group, arylalkenyl group, arylalkynyl group, cyano group, or a monovalent heterocyclic group. c and d each independently represent an integer of 0 to 4. When c is two or more, a plurality of $R^4$s may be the same or different. When d is two or more, a plurality of $R^5$ may be the same or different.)

BEST MODE FOR CARRYING OUT THE INVENTION

In the present invention, the metal complex structure showing light emission from triplet excited state means a structure derived from a triplet light-emitting complex.

The triplet light-emitting complex which is a ground material of the metal complex structure showing light emission from triplet excited state will be explained.

The triplet light-emitting complex is usually a heavy metal complex, for example, a complex which may generate phosphorescence emission from said complex. Complexes in which fluorescence emission is observed in addition to phosphorescence emission are also included.

The triplet light-emitting complexes are those having been used as a low molecular weight EL material. Such materials are disclosed, for example, in: Nature, (1998) 395, 151; Appl. Phys. Lett., (1999) 75(1), 4; Proc. SPIE-Int. Soc. Opt. Eng., (2001) 4105; (Organic Light-Emitting Materials and Devices IV), 119; J. Am. Chem. Soc., (2001) 123, 4304; Appl. Phys. Lett., (1997) 71(18), 2596; Syn. Met., (1998) 94(1), 103; Syn. Met., (1999) 99(2), 1361; and Adv. Mater., (1999), 11 (10), 852.

The central metal of the metal complex structure showing light emission from triplet excited state of the present invention is usually an atom having atomic number of 50 or more, spin-orbit interaction occurs in the complex, and intersystem crossing between a singlet state and a triplet state can occur in the metal.

As the central metal, exemplified are rhenium, iridium, osmium, scandium, yttrium, platinum, gold; and lanthanoids such as europium, terbium, thulium, dysprosium, samarium, praseodymium, gadolinium, etc. Iridium, platinum, gold, and europium are preferable; iridium, platinum, and gold are especially preferable; and iridium is the most preferable.

The ligand of the triplet light-emitting complex is usually an organic ligand, and the number of carbon atoms is usually about 3 to 60.

As the ligand of the triplet light-emitting complex, exemplified are 8-quinolinol and derivatives thereof, benzoquinolinol and derivatives thereof, 2-phenyl-pyridine and derivatives thereof, 2-phenyl-benzothiazole and derivatives thereof, 2-phenyl-benzoxazole and derivatives thereof, porphyrin derivatives thereof, etc.

As the triplet light-emitting complex, followings are exemplified.

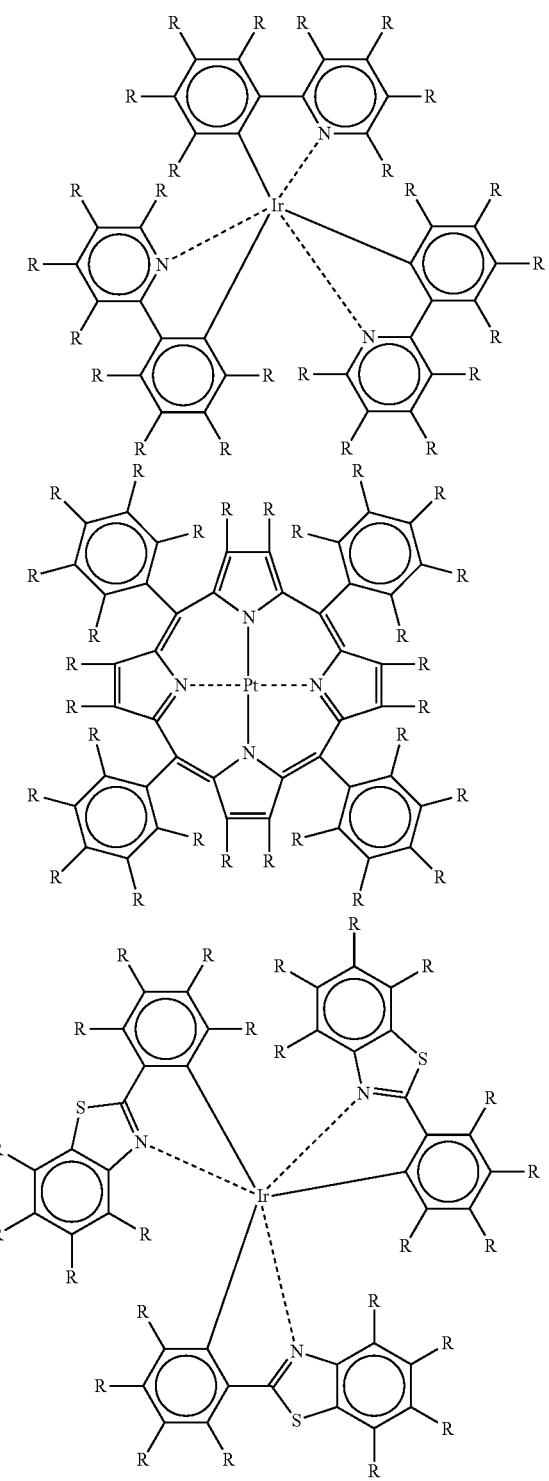

-continued
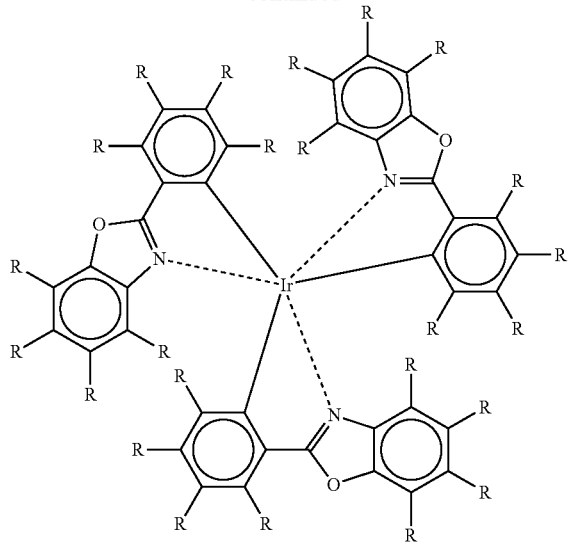
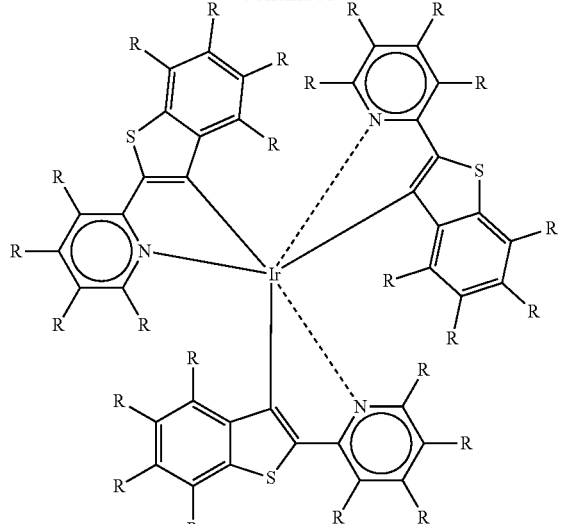
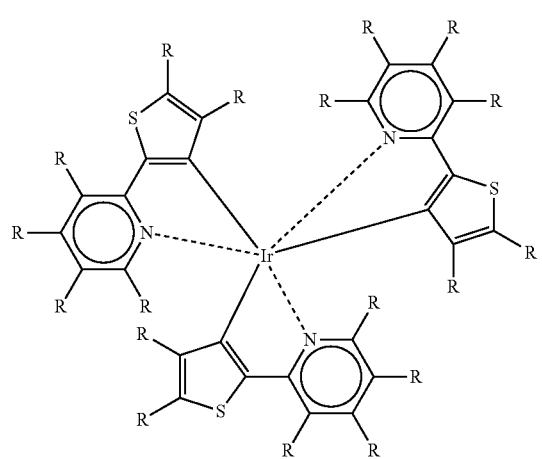
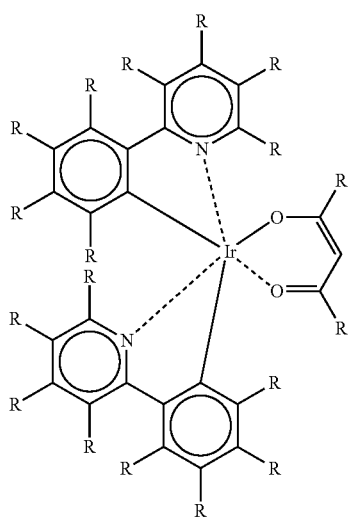
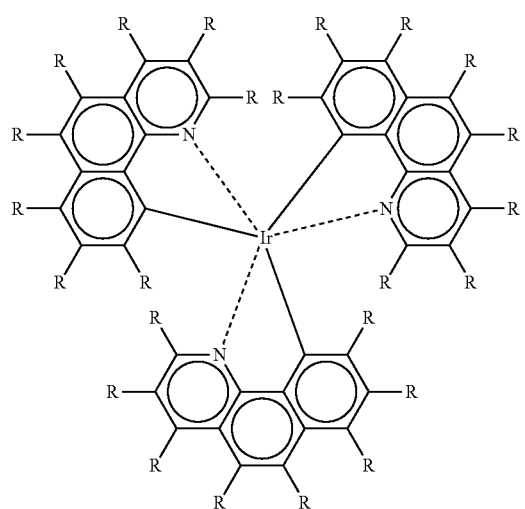
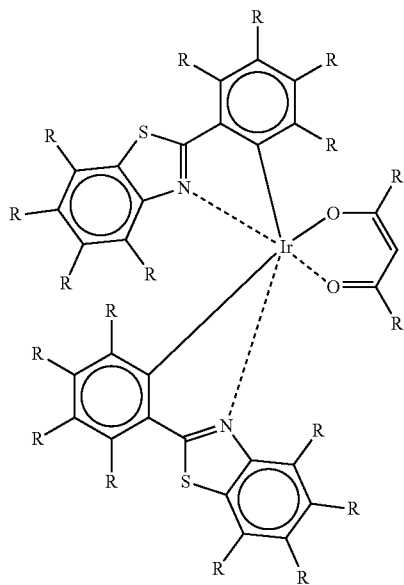

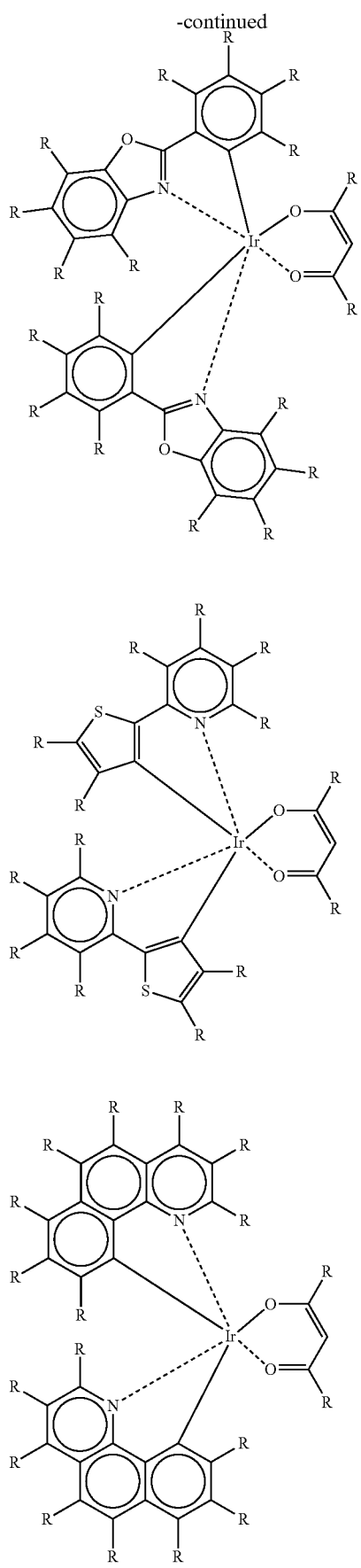
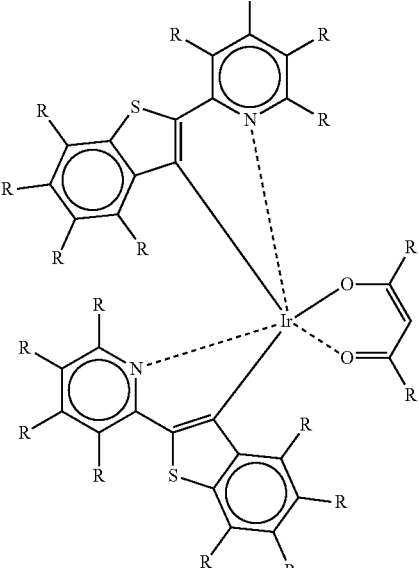
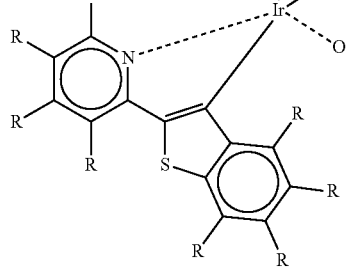
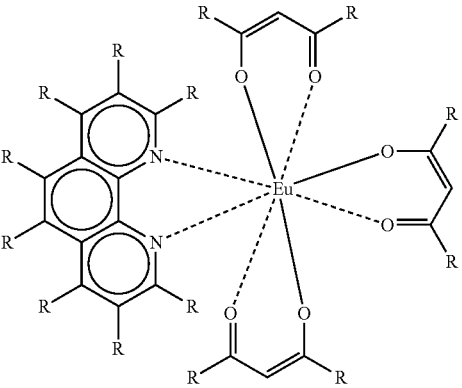
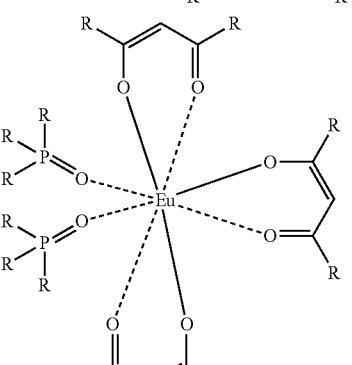

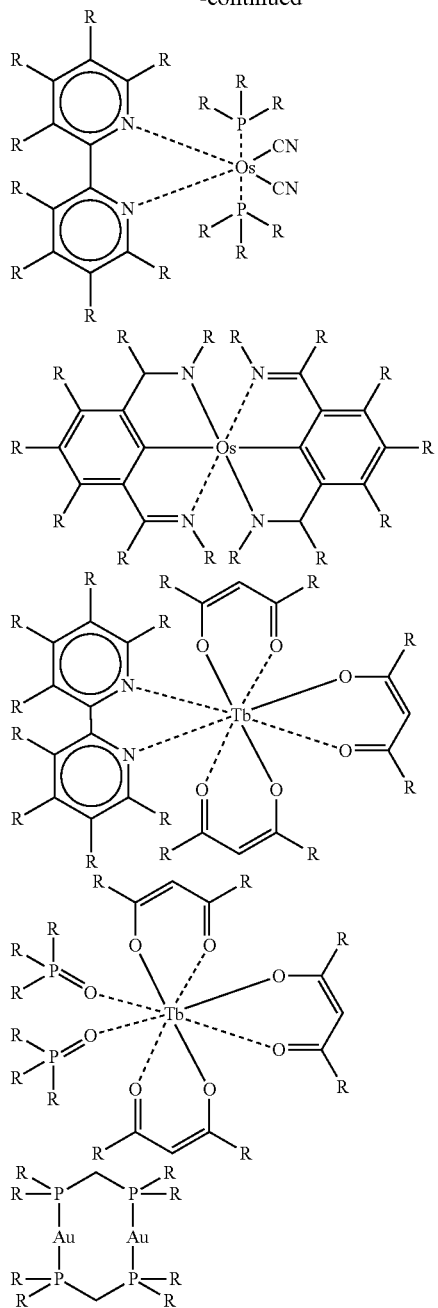

Here, R each independently represent a group selected from a halogen atom, alkyl group, alkoxy group, alkylthio group, alkylamino group, alkyl silyl group, aryl group, aryloxy group, arylthio group, aryl amino group, arylsilyl group, arylalkyl group, arylalkoxy group, arylalkylthio group, arylalkylamino group, arylalkylsilyl group, acyl group, acyloxy group, imino group, amide group, arylalkenyl group, arylalkynyl group, cyano group, monovalent heterocyclic group, a group represented by the above formula (1), and a group represented by the above formula (2). In order to improve the solubility into a solvent, it is preferable that one or more of Rs contain an alkyl chain having cyclic or long chain, and examples of R include a cyclopentyl group, cyclohexyl group, pentyl group, hexyl group, octyl group, 2-ethylhexyl group, decyl group, and 3,7-dimethyloctyl group. Two sub-stituents may be connected to form a ring. Furthermore, a part of carbon atoms in alkyl chain may be replaced by a group having a hetero atom, and examples of the hetero atom include an oxygen atom, a sulfur atom, a nitrogen atom, etc. Examples of the halogen atom include fluorine, chlorine, bromine, and iodine.

The alkyl group may be any of linear, branched or cyclic, and may have one or more substituents. The number of carbon atoms is usually from about 1 to 20, and specific examples thereof include methyl group, ethyl group, propyl group, i-propyl group, butyl group, i-butyl group, t-butyl group, pentyl group, cyclopentyl group, hexyl group, cyclohexyl group, heptyl group, octyl group, 2-ethylhexyl group, nonyl group, decyl group, 3,7-dimethyloctyl group, lauryl group, trifluoromethyl group, pentafluoroethyl group, perfluorobutyl group, perfluorohexyl group, perfluorooctyl group, etc.; and pentyl group, hexyl group, octyl group, 2-ethylhexyl group, decyl group, and 3,7-dimethyloctyl group are preferable.

The alkoxy group may be any of linear, branched or cyclic, and may have one or more substituents. The number of carbon atoms is usually from about 1 to 20, and specific examples thereof include methoxy group, ethoxy group, propyloxy group, i-propyloxy group, butoxy group, i-butoxy group, t-butoxy group, pentyloxy group, cyclopentyloxy group, hexyloxy group, cyclohexyloxy group, heptyloxy group, octyloxy group, 2-ethyl hexyloxy group, nonyloxy group, decyloxy group, 3,7-dimethyl octyloxy group, lauryloxy group, trifluoromethoxy group, pentafluoroethoxy group, perfluorobutoxy group, perfluoro hexyl group, perfluorooctyl group, methoxymethyloxy group, 2-methoxyethyloxy group, etc.; and pentyloxy group, hexyloxy group, octyloxy group, 2-ethylhexyloxy group, decyloxy group, and 3,7-dimethyloctyloxy group are preferable.

The alkylthio group may be any of linear, branched or cyclic, and may have one or more substituents. The number of carbon atoms is usually from about 1 to 20, and specific examples thereof include methylthio group, ethylthio group, propylthio group, i-propylthio group, butylthio group, i-butylthio group, t-butylthio group, pentylthio group, cyclopentylthio group, hexylthio group, cyclohexylthio group, heptylthio group, octylthio group, 2-ethylhexylthio group, nonylthio group, decylthio group, 3,7-dimethyloctylthio group, laurylthio group, trifluoromethylthio group, etc.; and pentylthio group, hexylthio group, octylthio group, 2-ethylhexylthio group, decylthio group, and 3,7-dimethyloctylthio group are preferable.

The alkylamino group may be any of linear, branched or cyclic, and may be monoalkylamino group or dialkylamino group. The number of carbon atoms is usually from about 1 to 40, and specific examples thereof include methylamino group, dimethyl amino group, ethylamino group, diethylamino group, propyl amino group, dipropylamino group, i-propylamino group, diisopropylamino group, butylamino group, i-butylamino group, t-butylamino group, pentylamino group, cyclopentylamino group, hexylamino group, cyclohexylamino group, heptylamino group, octylamino group, 2-ethylhexylamino group, nonylamino group, decylamino group, 3,7-dimethyloctylamino group, laurylamino group, cyclopentylamino group, dicyclopentylamino group, cyclohexylamino group, dicyclohexylamino group, pyrrolidyl group, piperidyl group, ditrifluoromethylamino group, etc.; and pentylamino group, hexylamino group, octylamino group, 2-ethylhexylamino group, decylamino group, and 3,7-dimethyl octylamino group are preferable.

The alkylsilyl group may be any of linear, branched or cyclic, and the number of carbon atoms is usually from about 1 to 60. Specific examples thereof include trimethylsilyl group, triethylsilyl group, tripropylsilyl group, tri-i-propylsilyl group, dimethyl-i-propylsilyl group, diethyl-i-propylsilyl group, t-butylsilyldimethylsilyl group, pentyldimethylsilyl group, hexyldimethylsilyl group, heptyldimethylsilyl group, octyldimethylsilyl group, 2-ethylhexyl-dimethylsilyl group, nonyldimethylsilyl group, decyldimethylsilyl group, 3,7-dimethyloctyl-dimethylsilyl group, lauryldimethylsilyl group etc.; and pentyldimethylsilyl group, hexyldimethylsilyl group, octyldimethylsilyl group, 2-ethylhexyl-dimethyl silyl group, decyldimethylsilyl group, and 3,7-dimethyloctyl dimethylsilyl group are preferable.

The aryl group may have one or more substituents, and the number of carbon atoms is usually from about 6 to 60. Specific examples thereof include phenyl group, $C_1$-$C_{12}$ alkoxyphenyl group ($C_1$-$C_{12}$ represents the number of carbon atoms 1-12. Hereafter the same.), $C_1$-$C_{12}$ alkylphenyl group, 1-naphtyl group, 2-naphtyl group, pentafluorophenyl group, pyridyl group, pyridazinyl group, pyrimidyl group, pyrazyl group, triazyl group, etc.; and $C_1$-$C_{12}$ alkoxyphenyl group, and $C_1$-$C_{12}$ alkylphenyl group are preferable.

The aryloxy group may have one or more substituents on the aromatic ring, and the number of carbon atoms is usually from about 6 to 60. Specific examples thereof include phenoxy group, $C_1$-$C_{12}$ alkoxyphenoxy group, $C_1$-$C_{12}$ alkylphenoxy group, 1-naphtyloxy group, 2-naphtyloxy group, pentafluorophenyloxy group, pyridyloxy group, pyridazinyloxy group, pyrimidyloxy group, pyrazyloxy group, triazyloxy group, etc.; and $C_1$-$C_{12}$ alkoxyphenoxy group, and $C_1$-$C_{12}$ alkylphenoxy group are preferable.

The arylthio group may have one or more substituents on the aromatic ring, and the number of carbon atoms is usually from about 6 to 60. Specific examples thereof include phenylthio group, $C_1$-$C_{12}$ alkoxyphenylthio group, $C_1$-$C_{12}$ alkyl phenylthio group, 1-naphthylthio group, 2-naphthylthio group, pentafluorophenylthio group, pyridylthio group, pyridazinylthio group, pyrimidylthio group, pyrazylthio group, triazylthio group, etc.; and $C_1$-$C_{12}$ alkoxyphenylthio group, and $C_1$-$C_{12}$ alkylphenylthio group are preferable.

The arylamino group may have one or more substituents on the aromatic ring, and the number of carbon atoms is usually from about 6 to 60. Specific examples thereof include phenylamino group, diphenylamino group, $C_1$-$C_{12}$ alkoxyphenylamino group, di($C_1$-$C_{12}$ alkoxyphenyl)amino group, di($C_1$-$C_{12}$ alkylphenyl)amino group, 1-naphtylamino group, 2-naphtylamino group, pentafluorophenylamino group, pyridyl amino group, pyridazinylamino group, pyrimidylamino group, pyrazylamino group, triazylamino group, etc.; and $C_1$-$C_{12}$ alkylphenylamino group and di($C_1$-$C_{12}$ alkylphenyl)amino group are preferable.

The arylsilyl group may have one or more substituents on the aromatic ring, and the number of carbon atoms is usually from about 6 to 60. Specific examples thereof include triphenyl silyl group, tri-p-xylylsilyl group, tribenzylsilyl group, diphenylmethylsilyl group, t-butyldiphenylsilyl group, dimethylphenylsilyl group, etc.

The arylalkyl group may have one or more substituents, and the number of carbon atoms is usually from about 7 to 60. Specific examples thereof include phenyl-$C_1$-$C_{12}$ alkyl group, $C_1$-$C_{12}$ alkoxyphenyl-$C_1$-$C_{12}$ alkyl group, $C_1$-$C_{12}$ alkylphenyl-$C_1$-$C_{12}$ alkyl group, 1-naphtyl-$C_1$-$C_{12}$ alkyl group, 2-naphtyl-$C_1$-$C_{12}$ alkyl group, etc.; and $C_1$-$C_{12}$ alkoxyphenyl-$C_1$-$C_{12}$ alkyl group, and $C_1$-$C_{12}$ alkyl phenyl-$C_1$-$C_{12}$ alkyl group are preferable.

The arylalkoxy group may have one or more substituents, and the number of carbon atoms is usually from about 7 to 60. Specific examples thereof include phenyl-$C_1$-$C_{12}$ alkoxy group, $C_1$-$C_{12}$ alkoxyphenyl-$C_1$-$C_{12}$ alkoxy group, $C_1$-$C_{12}$ alkyl phenyl-$C_1$-$C_{12}$ alkoxy group, 1-naphtyl-$C_1$-$C_{12}$ alkoxy group, 2-naphtyl-$C_1$-$C_{12}$ alkoxy group, etc.; and $C_1$-$C_{12}$ alkoxy phenyl-$C_1$-$C_{12}$ alkoxy group, and $C_1$-$C_{12}$ alkyl phenyl-$C_1$-$C_{12}$ alkoxy group are preferable.

The arylalkylthio group may have one or more substituents, and the number of carbon atoms is usually from about 7 to 60. Specific examples thereof include phenyl-$C_1$-$C_{12}$ alkylthio group, $C_1$-$C_{12}$ alkoxyphenyl-$C_1$-$C_{12}$ alkylthio group, $C_1$-$C_{12}$ alkylphenyl-$C_1$-$C_{12}$ alkylthio group, 1-naphtyl-$C_1$-$C_{12}$ alkylthio group, 2-naphtyl-$C_1$-$C_{12}$ alkylthio group, etc.; and $C_1$-$C_{12}$ alkoxyphenyl-$C_1$-$C_{12}$ alkylthio group, and $C_1$-$C_{12}$ alkyl phenyl-$C_1$-$C_{12}$ alkylthio group are preferable.

The arylalkylamino group has usually about 7 to 60 carbon atoms. Specific examples thereof include phenyl-$C_1$-$C_{12}$ alkyl amino group, $C_1$-$C_{12}$ alkoxyphenyl-$C_1$-$C_{12}$ alkylamino group, $C_1$-$C_{12}$-alkylphenyl-$C_1$-$C_{12}$ alkylamino group, di($C_1$-$C_{12}$ alkoxy phenyl-$C_1$-$C_{12}$ alkyl)amino group, di($C_1$-$C_{12}$ alkyl phenyl-$C_1$-$C_{12}$ alkyl)amino group, 1-naphtyl-$C_1$-$C_{12}$ alkylamino group, 2-naphtyl-$C_1$-$C_{12}$ alkylamino group, etc.; and $C_1$-$C_{12}$ alkylphenyl-$C_1$-$C_{12}$ alkylamino group, and di($C_1$-$C_{12}$ alkyl phenyl-$C_1$-$C_{12}$ alkyl)amino group are preferable.

The arylalkylsilyl group has usually about 7 to 60 carbon atoms. Specific examples thereof include phenyl-$C_1$-$C_{12}$ alkyl silyl group, $C_1$-$C_{12}$ alkoxyphenyl-$C_1$-$C_{12}$ alkylsilyl group, $C_1$-$C_{12}$ alkylphenyl-$C_1$-$C_{12}$ alkylsilyl group, 1-naphtyl-$C_1$-$C_{12}$ alkylsilyl group, 2-naphtyl-$C_1$-$C_{12}$ alkylsilyl group, phenyl-$C_1$-$C_{12}$ alkyldimethylsilyl group, etc.; and $C_1$-$C_{12}$ alkoxyphenyl-$C_1$-$C_{12}$ alkylsilyl group, and $C_1$-$C_{12}$ alkyl phenyl-$C_1$-$C_{12}$ alkylsilyl group are preferable.

The acyl group has usually about 2 to 20 carbon atoms. Specific examples thereof include acetyl group, propionyl group, butyryl group, isobutyryl group, pivaloyl group, benzoyl group, trifluoroacetyl group, pentafluorobenzoyl group, etc.

The acyloxy group has usually about 2 to 20 carbon atoms. Specific examples thereof include acetoxy group, propionyloxy group, butyryloxy group, isobutyryloxy group, pivaloyloxy group, benzoyloxy group, trifluoroacetyloxy group, pentafluorobenzoyloxy group, etc.

The imino group has usually about 2 to 20 carbon atoms. Specific examples thereof include the compounds represented by following formulas.

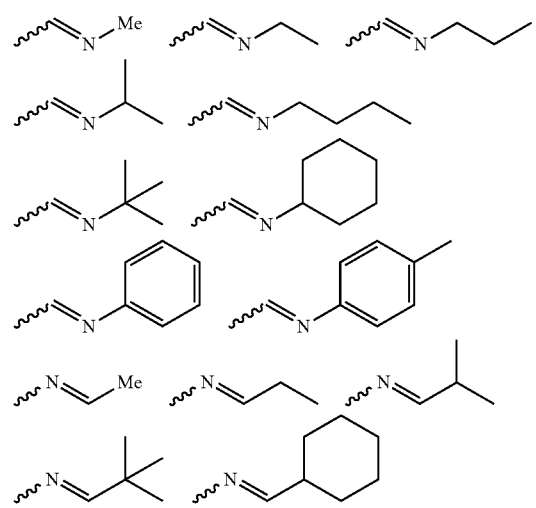

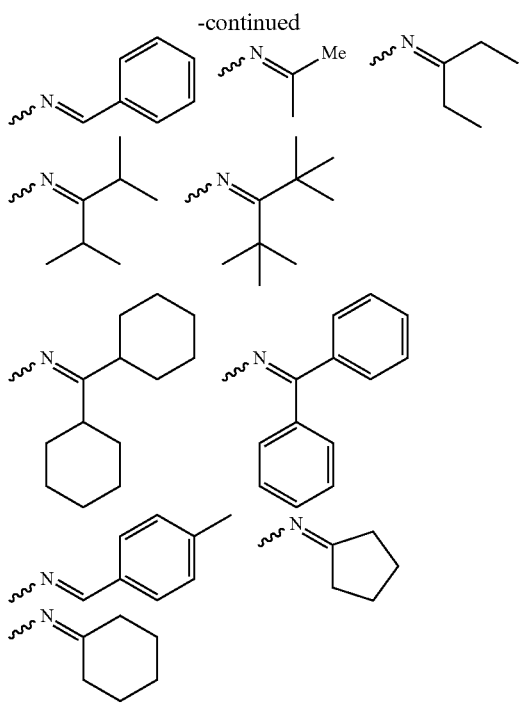

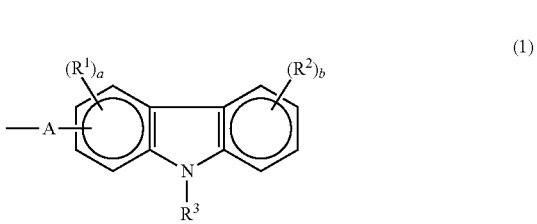

(1)

In the formula, A is a single bond or a divalent group derived from conjugate system. $R^1$ and $R^2$ each independently represent a halogen atom, alkyl group, alkoxy group, alkylthio group, alkylamino group, alkylsilyl group, aryl group, aryloxy group, arylthio group, arylamino group, arylsilyl group, arylalkyl group, arylalkoxy group, arylalkylthio group, arylalkylamino group, arylalkyl silyl group, acyl group, acyloxy group, imino group, amide group, arylalkenyl group, arylalkynyl group, cyano group, or a monovalent heterocyclic group. $R^3$ represents alkyl group, aryl group, arylalkyl group, arylalkenyl group, arylalkynyl group, or a monovalent heterocyclic group. a represents an integer of 0 to 3. b represents an integer of 0 to 4. When a is two or more, a plurality of $R^1$s may be the same or different, and mutually connected to form a ring. When b is two or more, a plurality of $R^2$s may be the same or different, and mutually connected to form a ring.

The amide group has usually about 2 to 20 carbon atoms. Specific examples thereof include formamide group, acetamide group, propioamide group, butyroamide group, benzamide group, trifluoroacetamide group, pentafluorobenzamide group, diform amide group, diacetoamide group, dipropioamide group, dibutyroamide group, dibenzamide group, ditrifluoro acetamide group, dipentafluorobenzamide group, etc.; and imides such as succinimide group and phthalic acid imide group, are also included.

The arylalkenyl group has usually about 7 to 60 carbon atoms. Specific examples thereof include phenyl-$C_1$-$C_{12}$ alkenyl group, $C_1$-$C_{12}$ alkoxyphenyl-$C_1$-$C_{12}$ alkenyl group, $C_1$-$C_{12}$ alkylphenyl-$C_1$-$C_{12}$ alkenyl group, 1-naphtyl-$C_1$-$C_{12}$ alkenyl group, 2-naphtyl-$C_1$-$C_{12}$ alkenyl group, etc.; and $C_1$-$C_{12}$ alkoxyphenyl-$C_1$-$C_{12}$ alkenyl group, and $C_1$-$C_{12}$ alkylphenyl-$C_1$-$C_{12}$ alkenyl group are preferable.

The arylalkynyl group has usually about 7 to 60 carbon atoms. Specific examples thereof include phenyl-$C_1$-$C_{12}$ alkynyl group, $C_1$-$C_{12}$ alkoxyphenyl-$C_1$-$C_{12}$ alkynyl group, $C_1$-$C_{12}$ alkylphenyl-$C_1$-$C_{12}$ alkynyl group, 1-naphtyl-$C_1$-$C_{12}$ alkynyl group, 2-naphtyl-$C_1$-$C_{12}$ alkynyl group, etc.; and $C_1$-$C_{12}$ alkoxyphenyl-$C_1$-$C_{12}$ alkynyl group, and $C_1$-$C_{12}$ alkylphenyl-$C_1$-$C_{12}$ alkynyl group are preferable.

The monovalent heterocyclic group means an atomic group in which a hydrogen atom is removed from a heterocyclic compound, and usually has about 4 to 60 carbon atoms. Specific examples thereof include thienyl group, $C_1$-$C_{12}$ alkylthienyl group, pyroryl group, furyl group, pyridyl group, $C_1$-$C_{12}$ alkylpyridyl group, etc.; and thienyl group, $C_1$-$C_{12}$ alkylthienyl group, pyridyl group, and $C_1$-$C_{12}$ alkylpyridyl group, are preferable. Furthermore, as for the aryl group and monovalent heterocyclic group in R, they may have one more or more substituents.

The metal complex of the present invention has a monovalent group represented by the below formula (1) or (2). Thereby, light emitting efficiency can be improved.

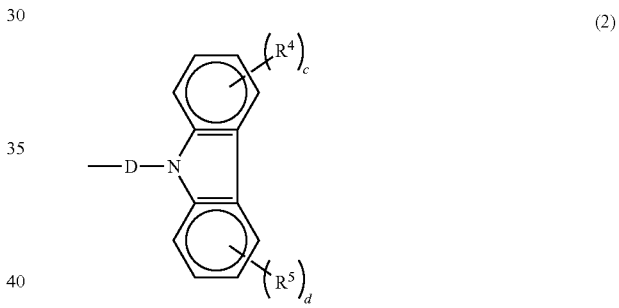

(2)

In the formula, D is a single bond or a divalent group derived from conjugate system. $R^4$ and $R^5$ each independently represent a halogen atom, alkyl group, alkoxy group, alkylthio group, alkylamino group, alkylsilyl group, aryl group, aryloxy group, arylthio group, arylamino group, arylsilyl group, arylalkyl group, arylalkoxy group, arylalkylthio group, arylalkyl amino group, arylalkyl silyl group, acyl group, acyloxy group, imino group, amide group, arylalkenyl group, arylalkynyl group, cyano group, or a monovalent heterocyclic group. c and d each independently represent an integer of 0 to 4. When c is two or more, a plurality of $R^4$s may be the same or different, and mutually connected to form a ring. When d is two or more, a plurality of $R^5$ may be the same or different, and mutually connected to form a ring.

In $R^1$ to $R^5$, the halogen atom, alkyl group, alkoxy group, alkylthio group, alkylamino group, alkylsilyl group, aryl group, aryloxy group, arylthio group, arylamino group, arylsilyl group, arylalkyl group, arylalkoxy group, arylalkylthio group, arylalkylamino group, arylalkylsilyl group, acyl group, acyloxy group, imino group, amide group, arylalkenyl group, arylalkynyl group, cyano group, and monovalent heterocyclic group, are the same as those of R exemplified above.

The divalent group derived from conjugate system in A or D is a group having a resonance structure to which delocalized π electron pair, unpaired electron, or lone electron pair join, and exemplified are vinylene group, acetylene group, an arylene group, a divalent heterocyclic group, bonding units shown below, and two or more combination thereof.

(In the formula, R' represents alkyl group, aryl group, arylalkyl group, arylalkenyl group, arylalkynyl group, or a monovalent heterocyclic group.)

The arylene group has usually 6-60, preferably 6-20 carbon atoms, and examples thereof include phenylene group (for example, following formulas 1-3), naphthalenediyl group (following formulas 4-13), anthracenylene group (following formulas 14-19), biphenylene group (following formulas 20-25), triphenylene group (following formulas 26-28), condensed-ring compound group (following formulas 29-38), etc. Here, the number of carbon atoms of substituent R is not counted as the number of carbon atoms of arylene group.

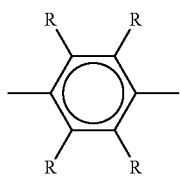
1

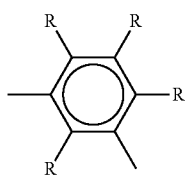
2

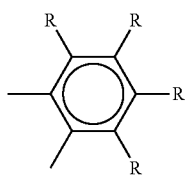
3

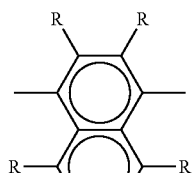
4

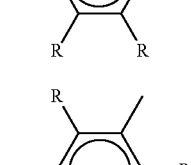
5

-continued

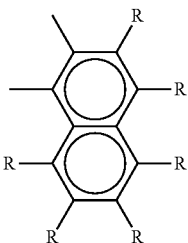
6

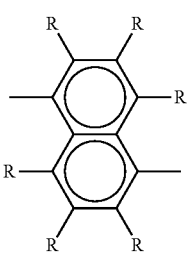
7

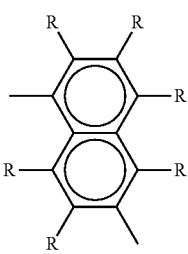
8

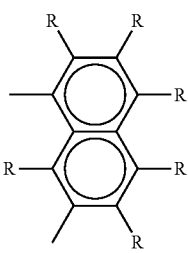
9

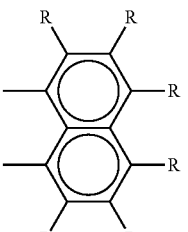
10

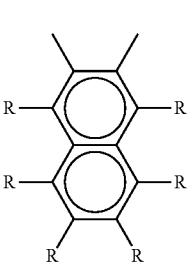
11

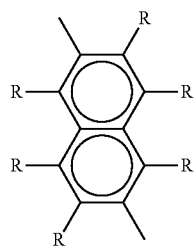
12
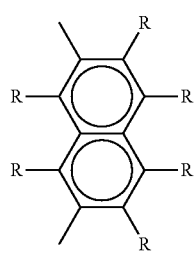
13
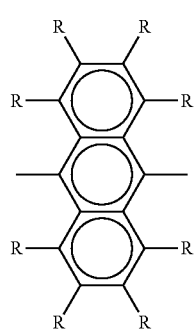
14
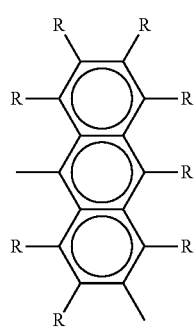
15
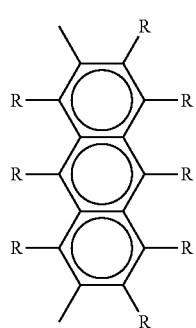
16
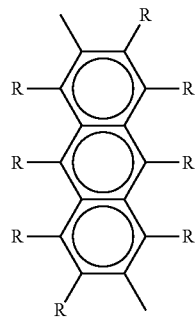
17
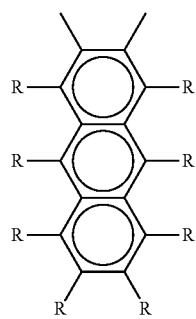
18
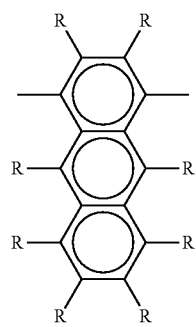
19
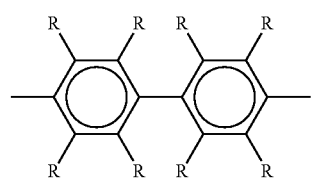
20
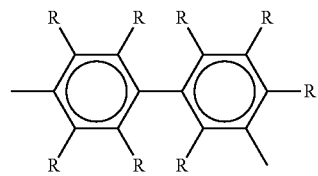
21
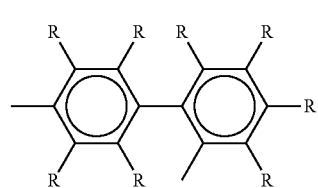
22

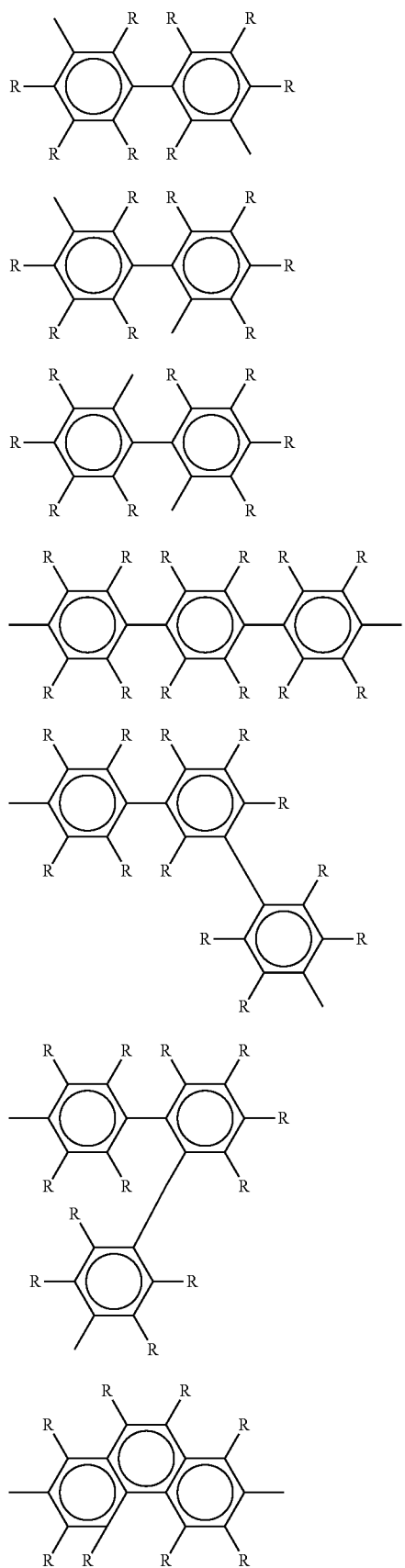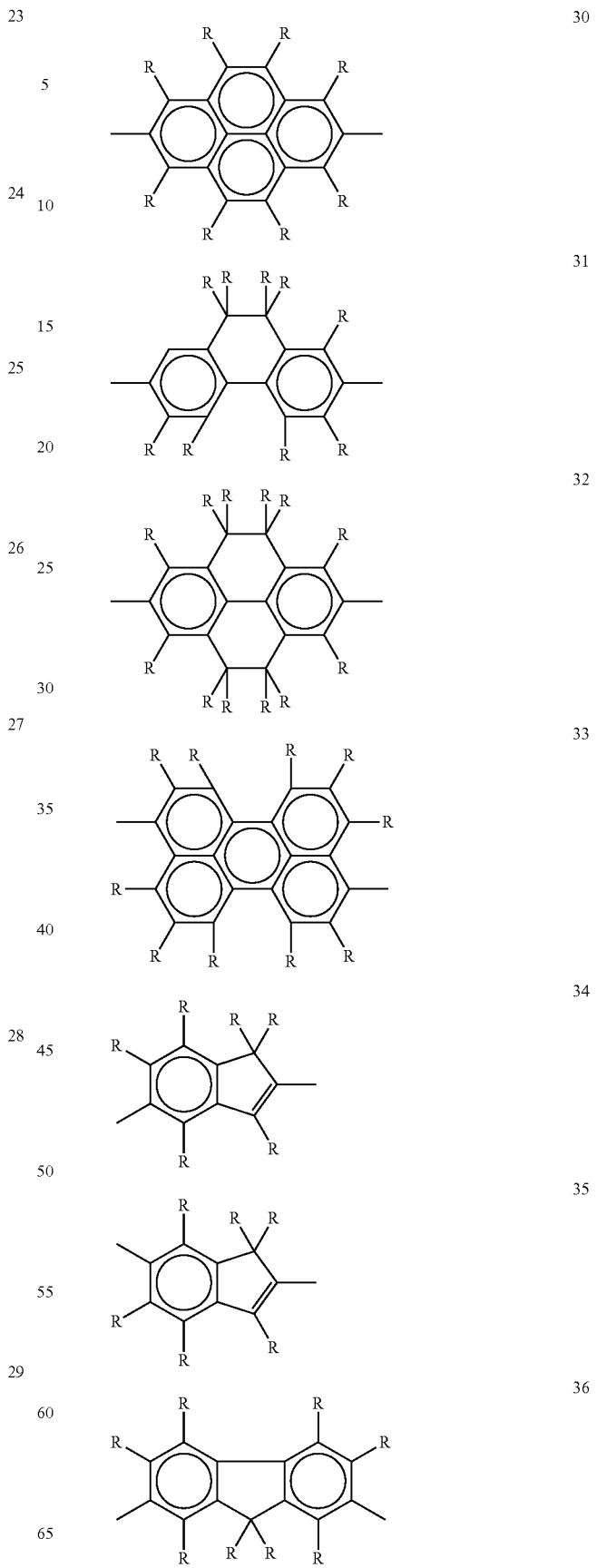

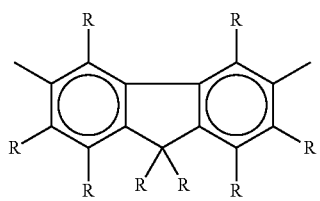
37

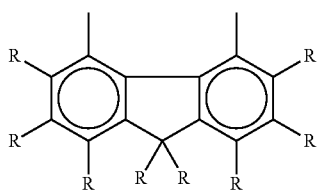
38

In the present invention, the divalent heterocyclic group means an atomic group in which two hydrogen atoms are removed from a heterocyclic compound, and the number of carbon atoms is usually 4-60, and preferably 4-20. Here, the number of carbon atoms of substituent is not counted as the number of carbon atoms of the divalent heterocyclic group.

The heterocyclic compound means an organic compound having a cyclic structure in which at least one heteroatom such as oxygen, sulfur, nitrogen, phosphorus, boron, etc. is contained in the cyclic structure as the element other than carbon atoms.

Examples of the divalent heterocyclic group include followings.

Divalent heterocyclic groups containing nitrogen as a hetero atom; pyridine-diyl group (following formulas 39-44), diaza phenylene group (following formulas 45-48), quinolinediyl group (following formulas 49-63), quinoxalinediyl group (following formulas 64-68), acridinediyl group (following formulas 69-72), bipyridyldiyl group (following formulas 73-75), phenanthrolinediyl group (following formulas 76-78), etc.

Groups having a fluorene structure containing silicon, nitrogen, sulfur, selenium, etc. as a hetero atom (following formulas 79-93). It is preferable to have an aromatic amine monomer containing a nitrogen atom, such as carbazole of formulas 82-84 or triphenylaminediyl group, in view of light emitting efficiency.

5 membered heterocyclic groups containing silicon, nitrogen, sulfur, selenium, etc. as a hetero atom: (following formulas 94-98)

Condensed 5 membered heterocyclic groups containing silicon, nitrogen, sulfur, selenium, etc. as a hetero atom: (following formulas 99-109), benzothiadiazole-4,7-diyl group, benzo oxadiazole-4,7-diyl group, etc.

5 membered heterocyclic groups containing silicon, nitrogen, sulfur, selenium, etc. as a hetero atom, which are connected at the α position of the hetero atom to form a dimer or an oligomer (following formulas 110-118); and 5 membered ring heterocyclic groups containing silicon, nitrogen, oxygen, sulfur, selenium, as a hetero atom is connected with a phenyl group at the α position of the hetero atom (following formulas 112-118).

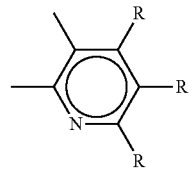
39

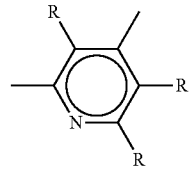
40

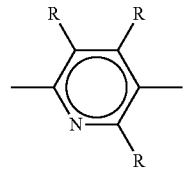
41

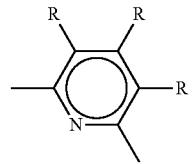
42

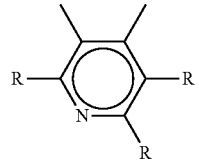
43

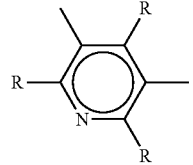
44

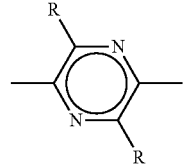
45

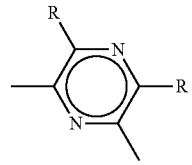
46

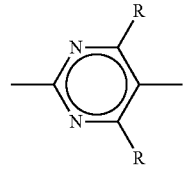
47

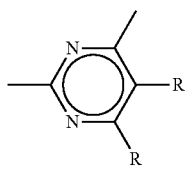
48
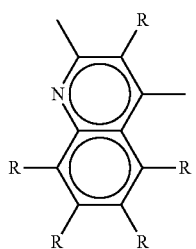
49
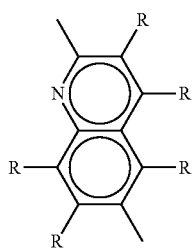
50
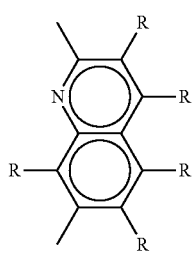
51
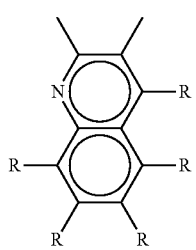
52
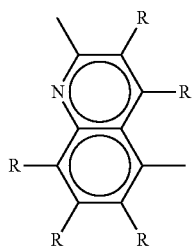
53
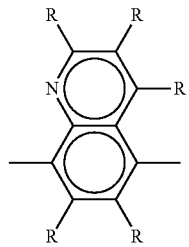
54
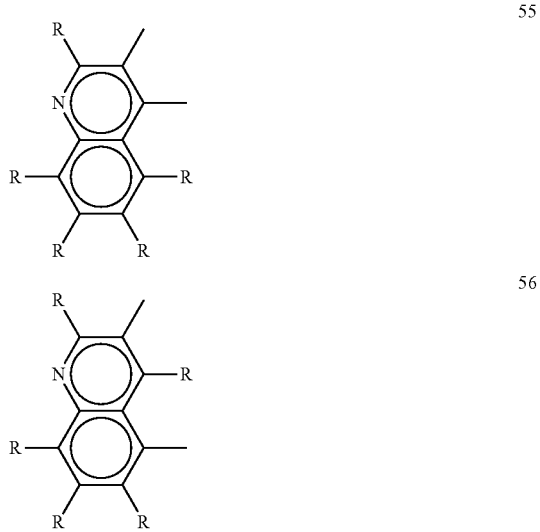
55
56
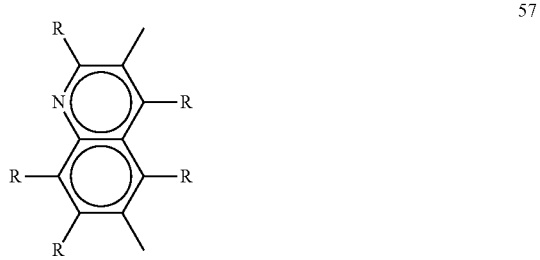
57
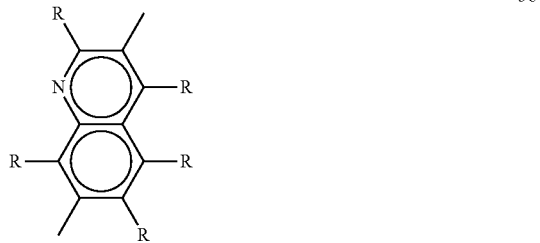
58
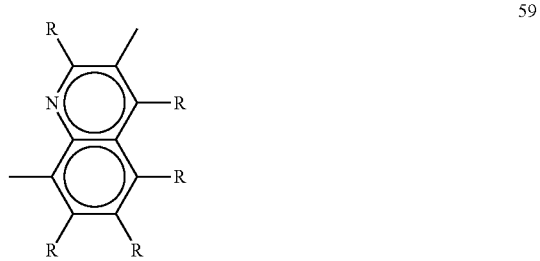
59

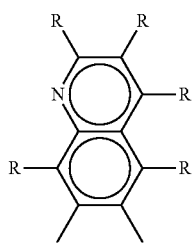
60
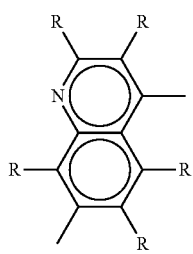
61
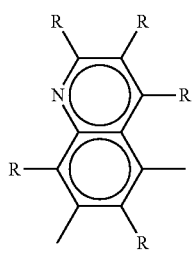
62
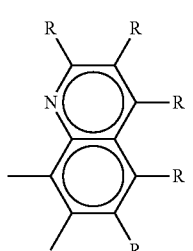
63
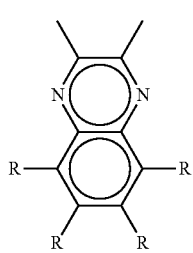
64
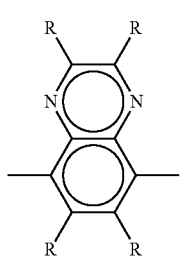
65
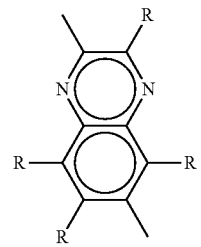
66
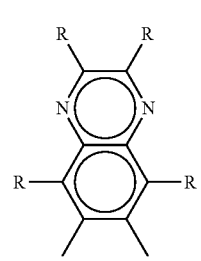
67
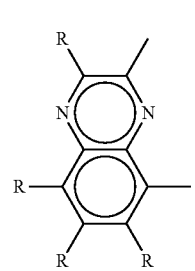
68
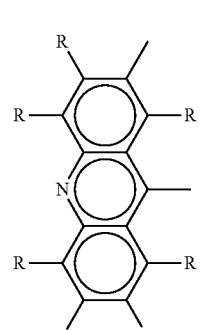
69
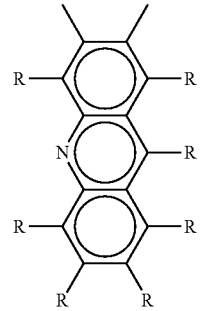
70

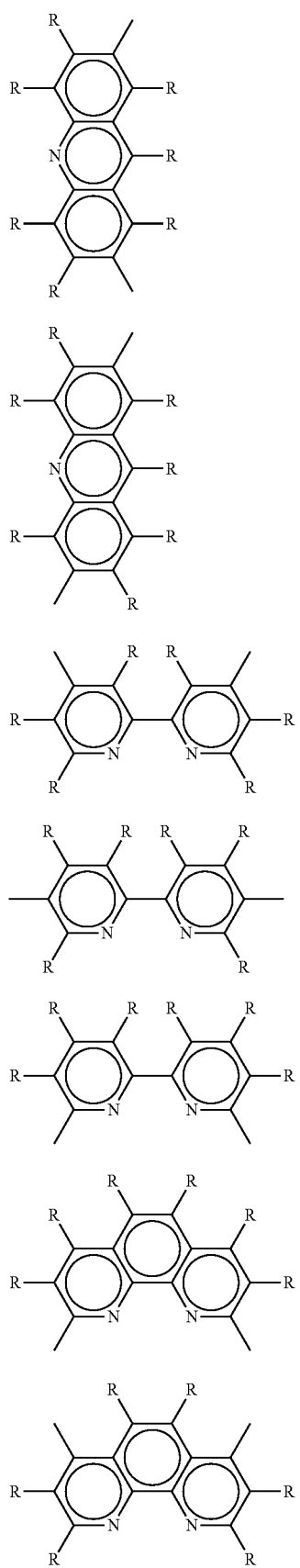
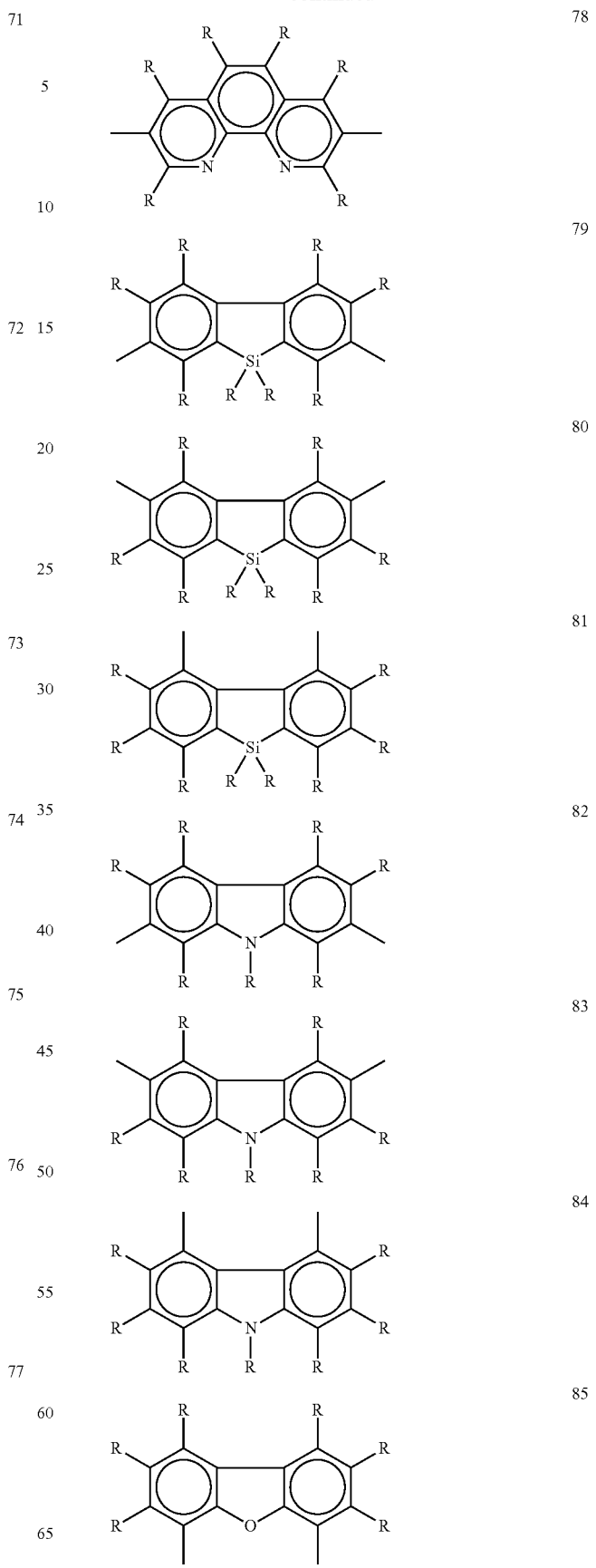

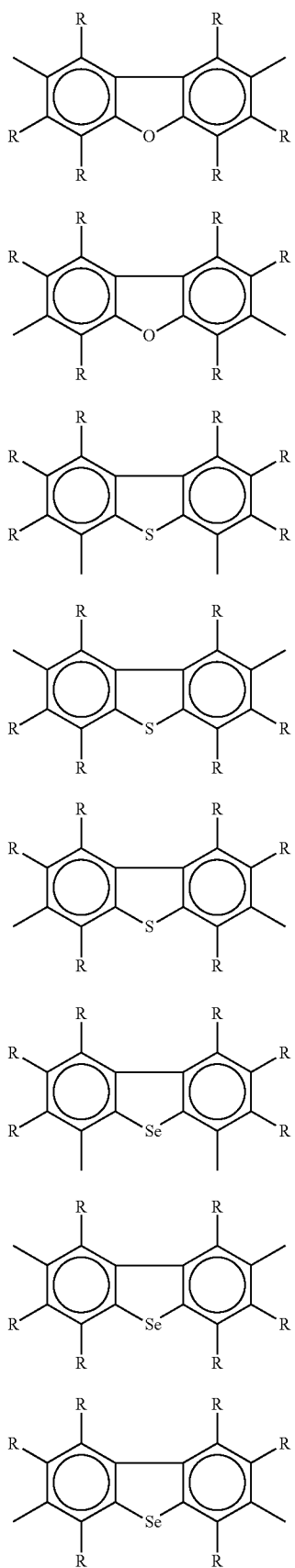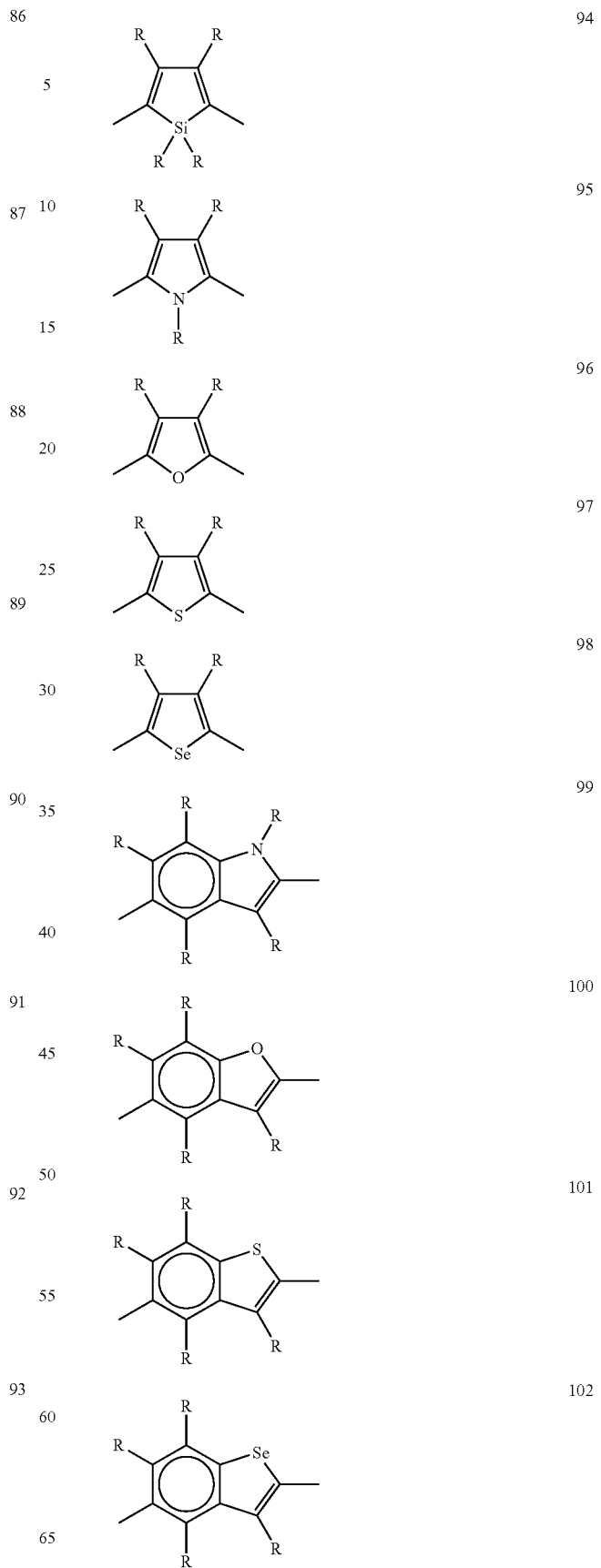

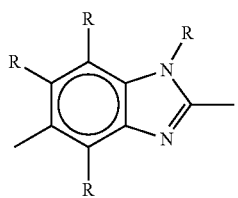
103
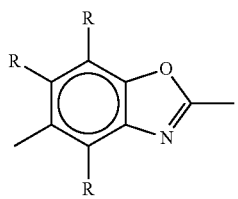
104
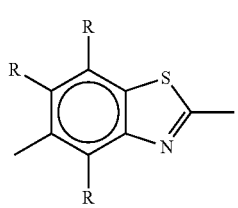
105
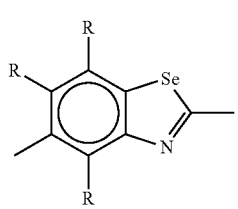
106
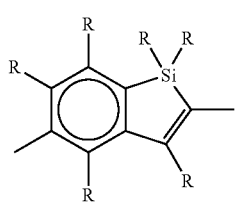
107
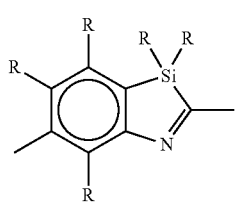
108
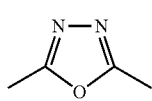
109
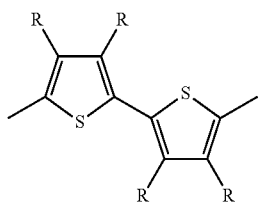
110
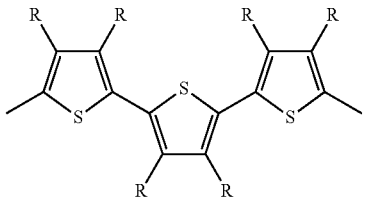
111
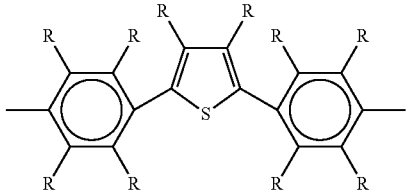
112
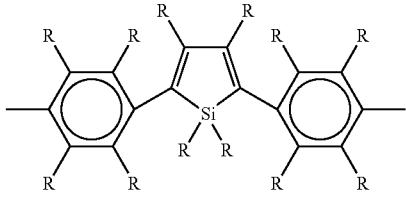
113
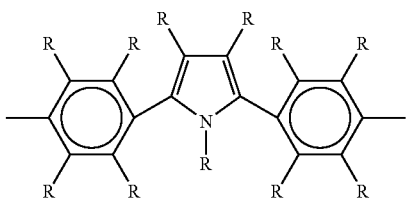
114
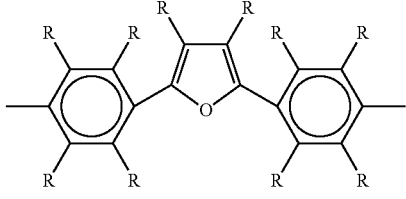
115
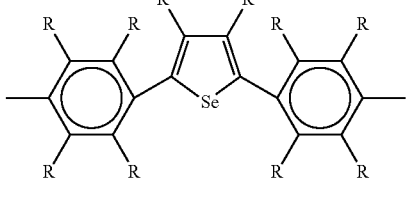
116
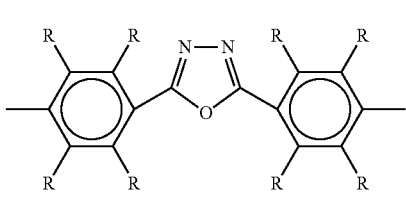
117
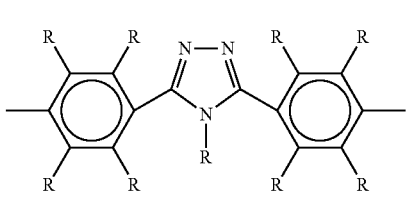
118
Here, R is the same group as those described above.

Concrete examples of A or D include following groups without being limited thereto.

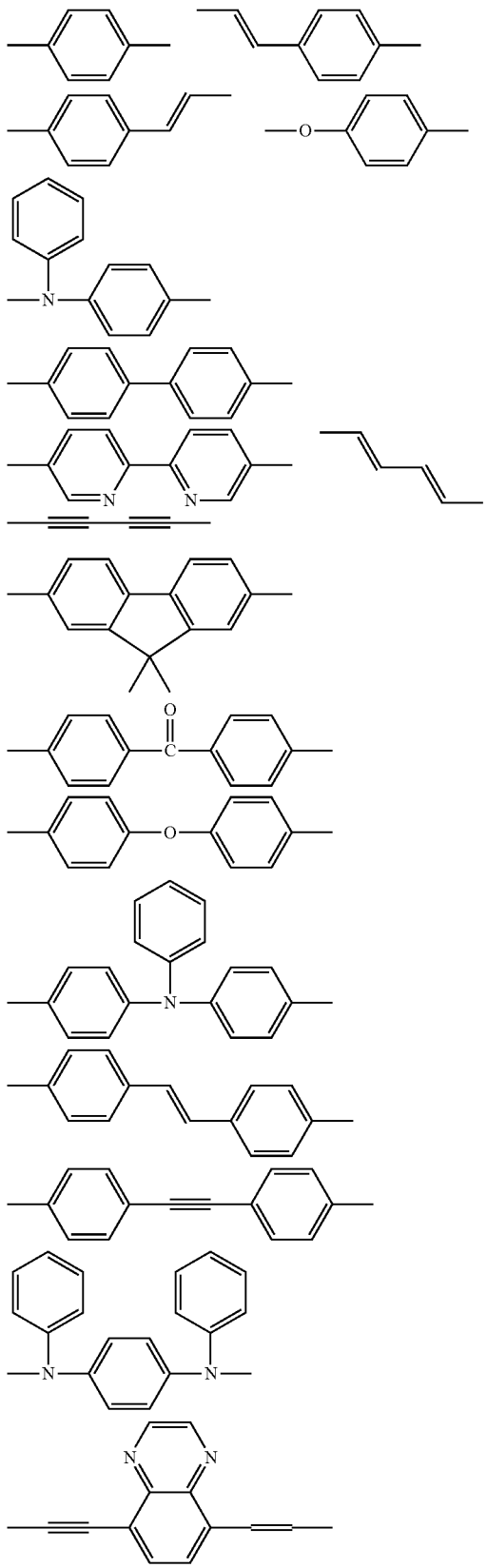

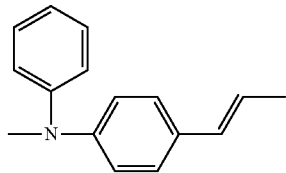 [SMILES: C/C=C/c1ccc(N(C)c2ccccc2)cc1]

The complex of the present invention is represented by the below formula (3), and is characterized by having phosphorescence in a visible region.

$$(L^1)_{\overline{l}}M^1\!\!-\!\!(L^2)_m \qquad (3)$$

Here, the phosphorescence in a visible region means phosphorescence having emission wavelength of 380-800 nm.

$M^1$ is a metal which is an atom having an atomic number of 50 or more, and intersystem crossing between a singlet state and a triplet state can occur in this complex by spin-orbit interaction. Examples of the atom represented by $M^1$ include: a rhenium atom, an osmium atom, an iridium atom, a platinum atom, a gold atom, a lanthanum atom, a cerium atom, a praseodymium atom, a neodymium atom, a promethium atom, a samarium atom, an europium atom, a gadolinium atom, a terbium atom, a dysprosium atom, etc.; preferably a rhenium atom, an osmium atom, an iridium atom, a platinum atom, a gold atom, a samarium atom, an europium atom, a gadolinium atom, a terbium atom, and a dysprosium atom; and more preferably, an iridium atom, a platinum atom, a gold atom, and an europium atom.

$L^2$ represents: a ligand which bonds to $M^1$ by one or more of nitrogen atom, oxygen atom, carbon atom, sulfur atom, or phosphorus atom; a halogen atom; or a hydrogen atom.

Here, as the ligand which bonds to $M^1$ by one or more of nitrogen atom, oxygen atom, carbon atom, sulfur atom, or phosphorus atom, may be zero-valent, mono-valent, or multi-valent.

Examples thereof include: alkyl group, alkoxy group, acyloxy group, alkylthio group, alkylamino group, aryl group, aryloxy group, arylthio group, arylamino group, arylalkyl group, aryl alkoxy group, arylalkylthio group, arylalkylamino group, sulfonate group, cyano group, heterocyclic ligand, carbonyl compound, ether, amine, imine, phosphine, phosphite, and sulfide; and multi-dentate ligands derived from combinations thereof.

As the alkyl group, alkoxy group, alkylthio group, alkylamino group, aryl group, aryloxy group, arylthio group, arylamino group, arylalkyl group, arylalkoxy group, arylalkylthio group, and arylalkylamino group, the groups described in the above R are exemplified.

Examples of the heterocyclic ligand include: a pyridine ring, pyrrole ring, thiophene ring, oxazole, and furan ring; and monovalent ligands in which a hydrogen atom is removed from these heterocyclic ring compounds.

Acyloxy group has about 2 to 20 carbon atoms, and specific examples thereof include acetyloxy group, trifluoroacetyloxy group, propionyloxy group, and benzoyloxy group. Examples of sulfonate group include benzene sulfonate group, p-toluene sulfonate group, methanesulfonate group, ethane sulfonate group, and trifluoromethane sulfonate group.

The carbonyl compound has a coordinate bond to $M^1$ through the oxygen atom, and examples thereof include: carbon monoxide; ketones such as acetone, and benzophenone; and diketones such as acetylacetone, and acenaphtoquinone.

The ether has a coordinate bond to $M^1$ through the oxygen atom, and examples thereof include dimethylether, diethylether, tetrahydrofuran, 1,2-dimethoxyethane, etc.

The amine has a coordinate bond to $M^1$ through the nitrogen atom, and examples thereof include: monoamines such as tri methylamine, triethylamine, tributylamine, tribenzylamine, triphenylamine, dimethylphenyl amine, and methyldiphenyl amine; and diamines such as 1,1,2,2-tetramethylethylene diamine, 1,1,2,2-tetraphenylethylenediamine, and 1,1,2,2-tetramethyl-o-phenylenediamine.

The imine has a coordinate bond to $M^1$ through the nitrogen atom, and examples thereof include: monoimines such as benzylidene aniline, benzylidenebenzylamine, and benzylidene methylamine; and diimines such as dibenzylidine ethylene diamine, dibenzylidine-o-phenylene diamine, and 2,3-bis(anilino) butane.

The phosphine has a coordinate bond to $M^1$ through the phosphorus atom, and examples thereof include triphenylphosphine, tri-o-tolylphosphine, tri-t-butylphosphine, tricyclohexyl phosphine, 1,2-bis(diphenylphosphino)ethane, and 1,3-bis(diphenylphosphino)propane.

The phosphite has a coordinate bond to $M^1$ through the phosphorus atom, and examples thereof include trimethylphosphite, triethylphosphite, triphenylphosphite, and tribenzyl phosphite.

The sulfide has a coordinate bond to $M^1$ through the sulfur atom, and examples thereof include dimethylsulfide, diphenyl sulfide, and thioanisole.

Examples of the multi-dentate ligands derived from combinations thereof include:

groups derived from the combination of a heterocyclic ring and a benzene ring such as phenylpyridine, 2-(paraphenylphenyl)pyridine, 2-phenylbenzoxazole, 2-(paraphenylphenyl)benzoxazole, 2-phenylbenzothiazole, 2-(paraphenylphenyl)benzothiazole, etc.;

groups derived from the combination of two or more heterocyclic rings such as 2-(4-thiophene-2-yl)pyridine, 2-(4-phenyl thiophene-2-yl)pyridine, 2-(benzothiophene-2-yl)pyridine, 2,3,7,8,12,13,17,18-octa ethyl-21H,23H-porphyrin, etc.; and acetonates such as acetylacetonate, dibenzomethylate, and thenoyltrifluoroacetonate.

l represents an integer of 1 to 3. m represents an integer of 0 to 3. When m is two or more, a plurality of $L^2$s may be the same or different. l+m is an integer of 2 to 6.

$L^1$ in formula (3) represents a ligand represented by the following formula (4) or formula (5).

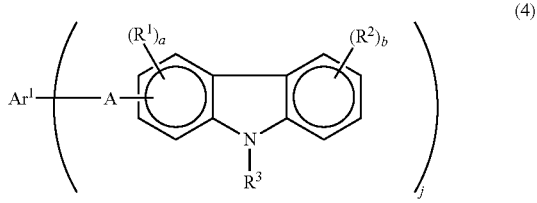

(4)

(Here, $Ar^1$ represents a residue of a ligand which bonds to $M^1$ by one or more of nitrogen atom, oxygen atom, carbon atom, sulfur atom, or phosphorus atom, and has covalent bonds to j pieces of As. j represents an integer of 1 to 3. In the formula, $R^1$ to $R^3$, A, a, b, and j are the same as those of the above formula (1)).

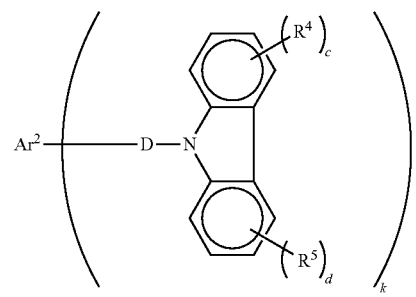

(5)

(Here, $Ar^2$ represents a residue of a ligand which bonds to $M^1$ by one or more of nitrogen atom, oxygen atom, carbon atom, sulfur atom, or phosphorus atom, and has covalent bonds to k pieces of Ds. In the formula, $R^4$, $R^5$, D, c, d, and k are the same as those of the above formula (2)).

In respect of the stability of a compound, it is preferable that $L^1$ has a coordinate bond to $M^1$ through at least one nitrogen atom or at least one carbon atom, and it is more preferable that $L^1$ is a multi-dentate ligand.

In view of light emitting efficiency, it is preferable that $L^1$ is a ligand represented by the above formula (4).

It is also preferable that $L^1$ is a ligand represented by the above formula (5), and D is a ligand of divalent group derived from conjugate system.

It is more preferable that $Ar^1$ or $Ar^2$ is a monovalent ligand represented by the below formula (6) or (7).

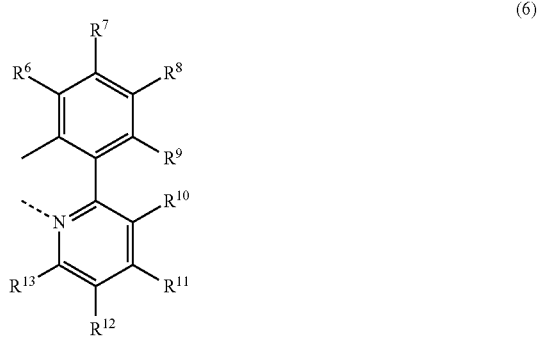

(6)

(here, $R^6$ to $R^{13}$ each independently represent a hydrogen atom, halogen atom, alkyl group, alkoxy group, alkylthio group, alkylamino group, alkylsilyl group, aryl group, aryloxy group, arylthio group, arylamino group, arylsilyl group, arylalkyl group, arylalkoxy group, arylalkylthio group, arylalkylamino group, arylalkylsilyl group, acyl group, acyloxy group, imino group, amide group, arylalkenyl group, arylalkynyl group, cyano group, monovalent heterocyclic group, or a group represented by the above formula (1) or formula (2), and they may be connected to form a ring. At least one of $R^6$ to $R^{13}$ is one represented by the above formula (1) or formula (2).)

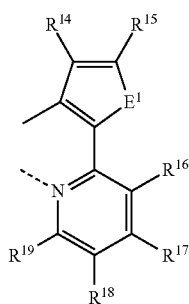
(7)

(In the formula, $E^1$ represents an oxygen atom or a sulfur atom.) $R^{14}$ to $R^{19}$ each independently represent a hydrogen atom, halogen atom, alkyl group, alkoxy group, alkylthio group, alkylamino group, alkylsilyl group, aryl group, aryloxy group, arylthio group, arylamino group, arylsilyl group, arylalkyl group, aryl alkoxy group, arylalkylthio group, arylalkylamino group, arylalkylsilyl group, acyl group, acyloxy group, imino group, amide group, arylalkenyl group, arylalkynyl group, cyano group, monovalent heterocyclic group, or a group represented by the above formula (1) or formula (2), and they may be connected to form a ring. At least one of $R^{14}$ to $R^{19}$ is one represented by the above formula (1) or formula (2).)

In respect to light emitting efficiency, it is preferable that $M^1$ is an iridium atom, platinum atom, gold atom, or europium atom.

Examples of $L^1$ include followings.

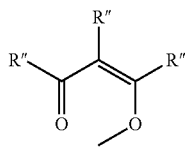

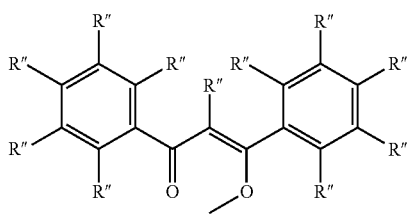

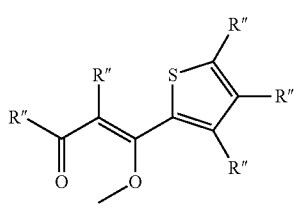

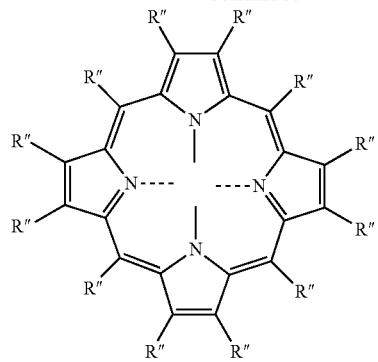

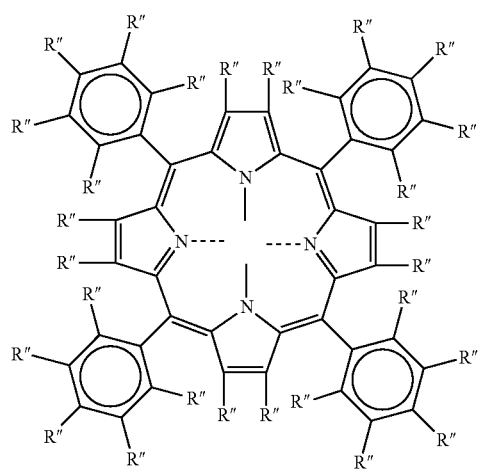

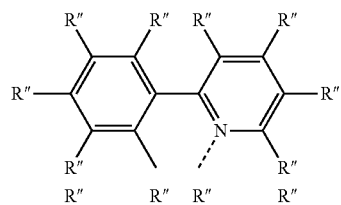

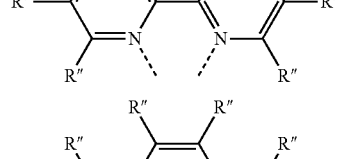

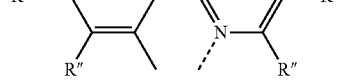

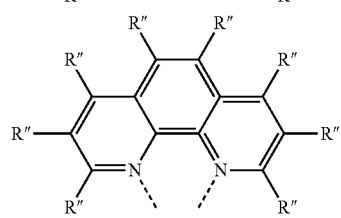

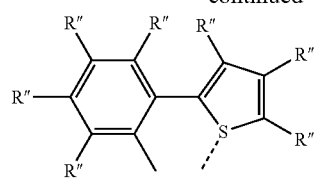
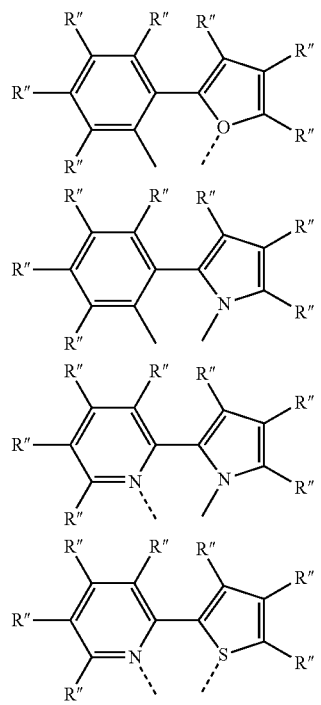
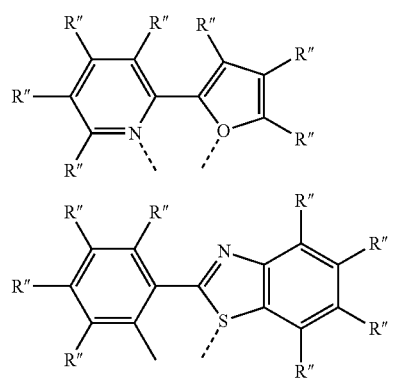
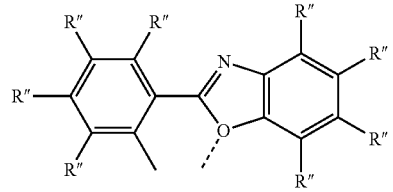
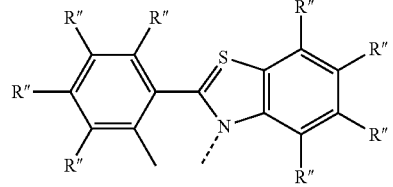
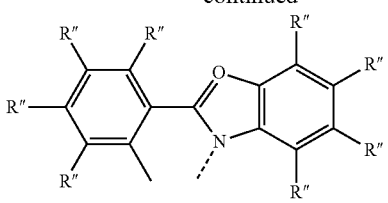
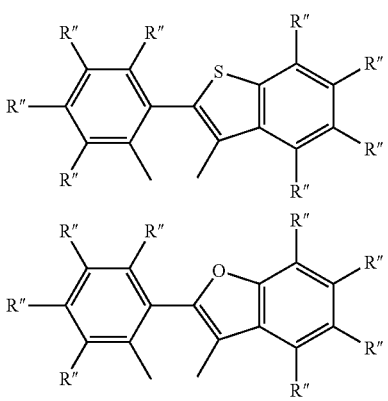
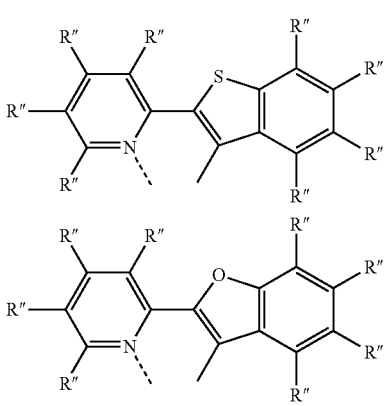
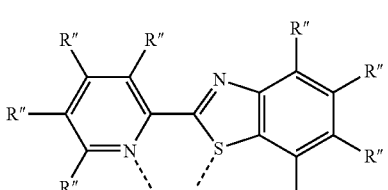
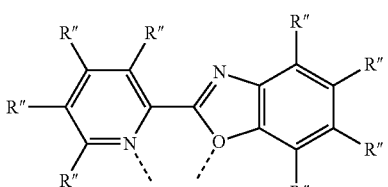
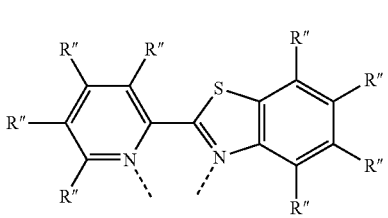

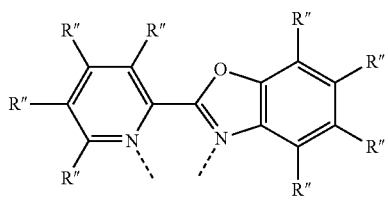

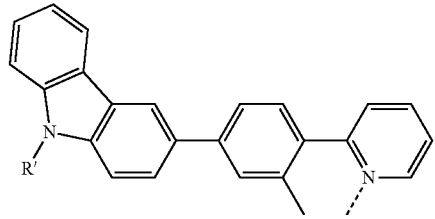

Here, R″ each independently represent a hydrogen atom, halogen atom, alkyl group, alkoxy group, alkylthio group, alkylamino group, alkylsilyl group, aryl group, aryloxy group, arylthio group, arylamino group, arylsilyl group, arylalkyl group, aryl alkoxy group, arylalkylthio group, arylalkylamino group, arylalkylsilyl group, acyl group, acyloxy group, imino group, amide group, arylalkenyl group, arylalkynyl group, cyano group, monovalent heterocyclic group, and a group represented by the above formula (1), or formula (2). Specific examples include those represented in the above R. In each ligand, at least one R″ is represented by the above formula (1) or formula (2). R″'s may be connected mutually to form a ring. In order to improve the solubility into a solvent, it is preferable that at least one of the R″ has a long alkyl group.

Examples of $L^1$ represented by formula (4) include followings.

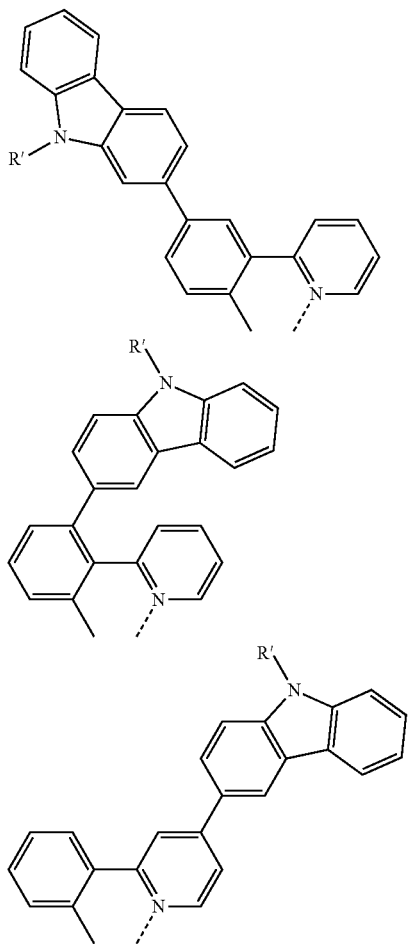

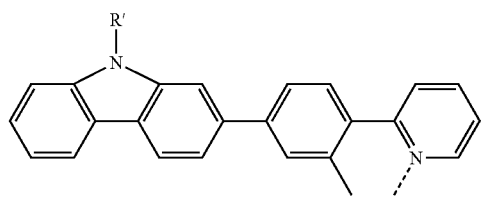

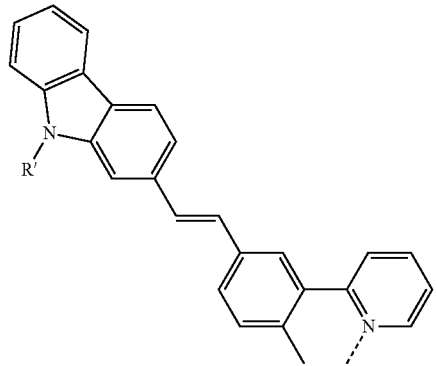

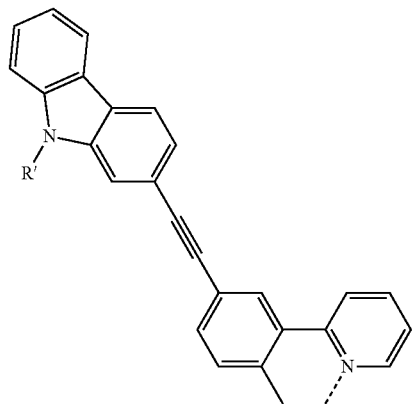

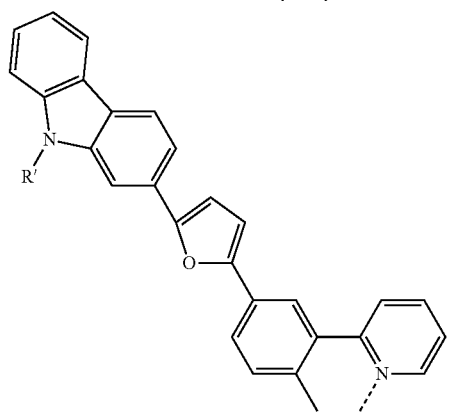

-continued
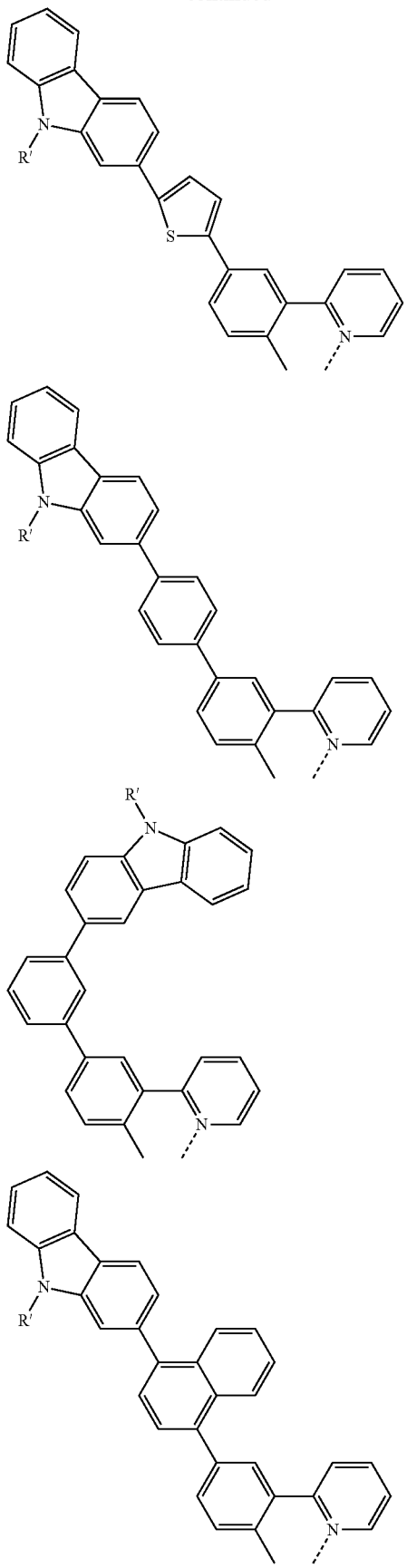
-continued
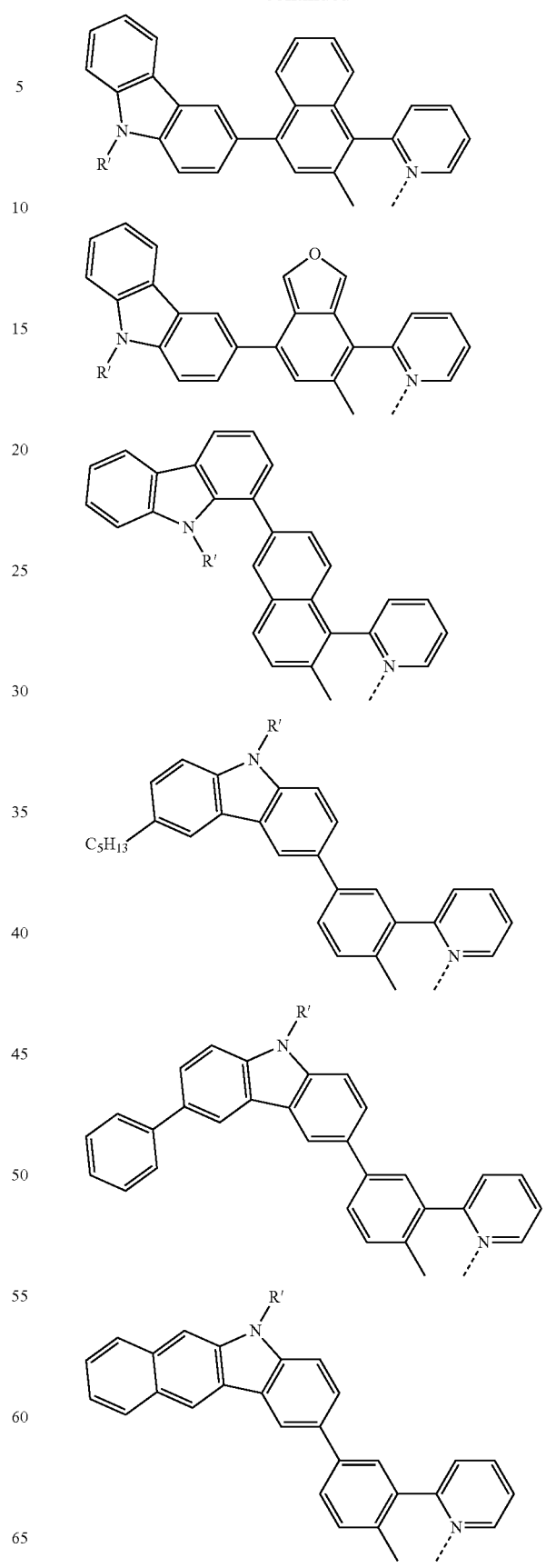

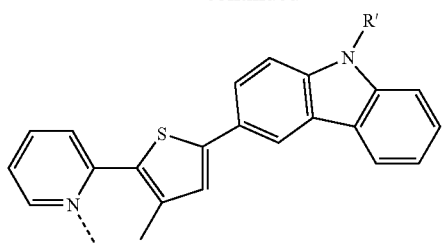
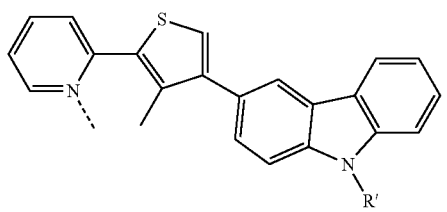
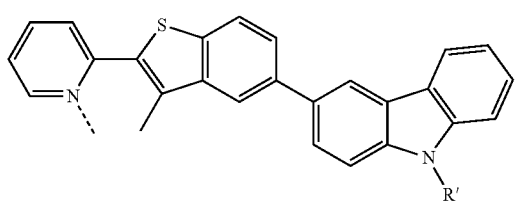
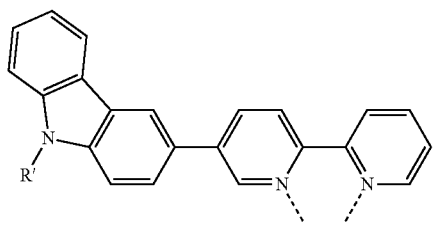
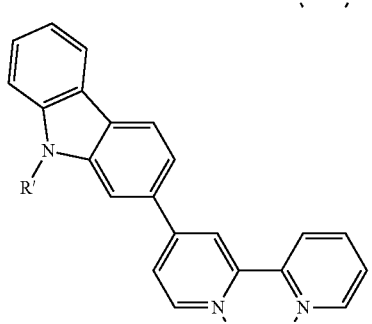
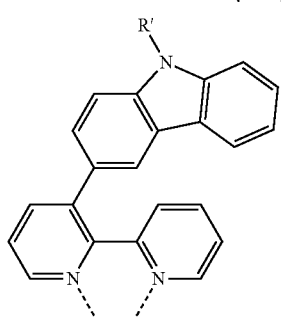
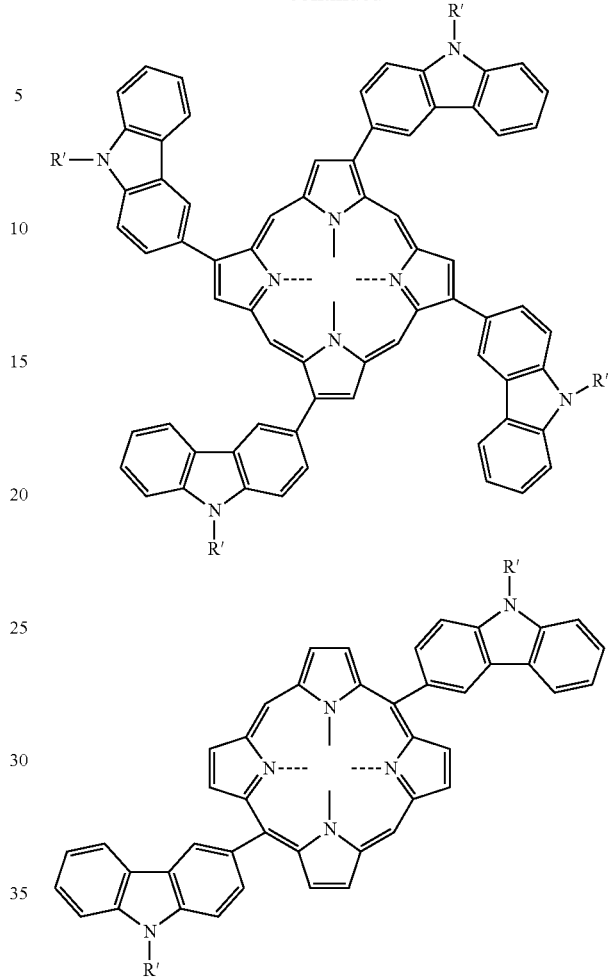
In the formula, R' represents an alkyl group, aryl group, arylalkyl group, arylalkenyl group, arylalkynyl group, or monovalent heterocyclic group.
Examples of $L^1$ represented by formula (5) include the following structures.
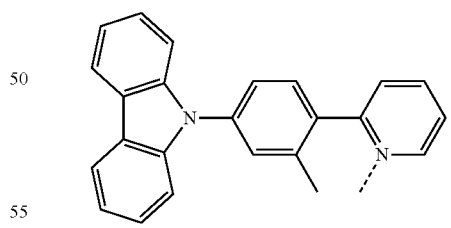
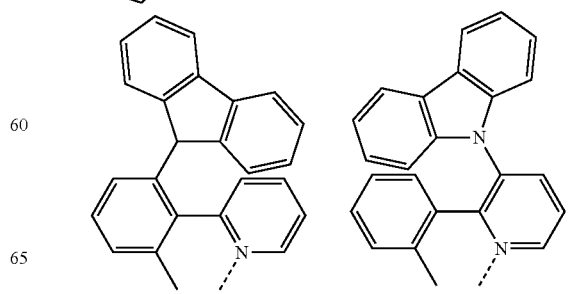

-continued
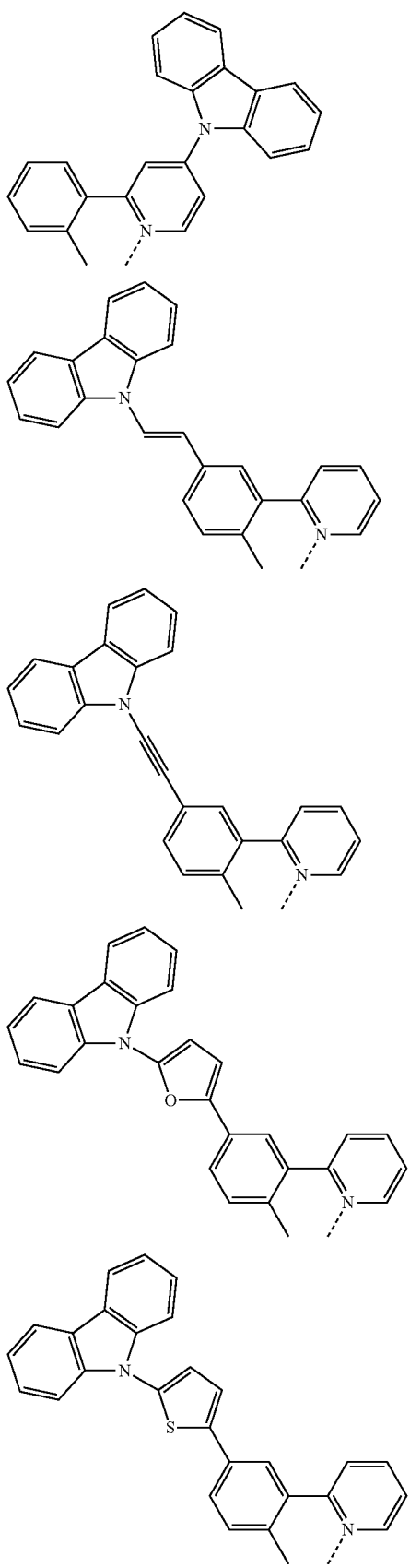
-continued
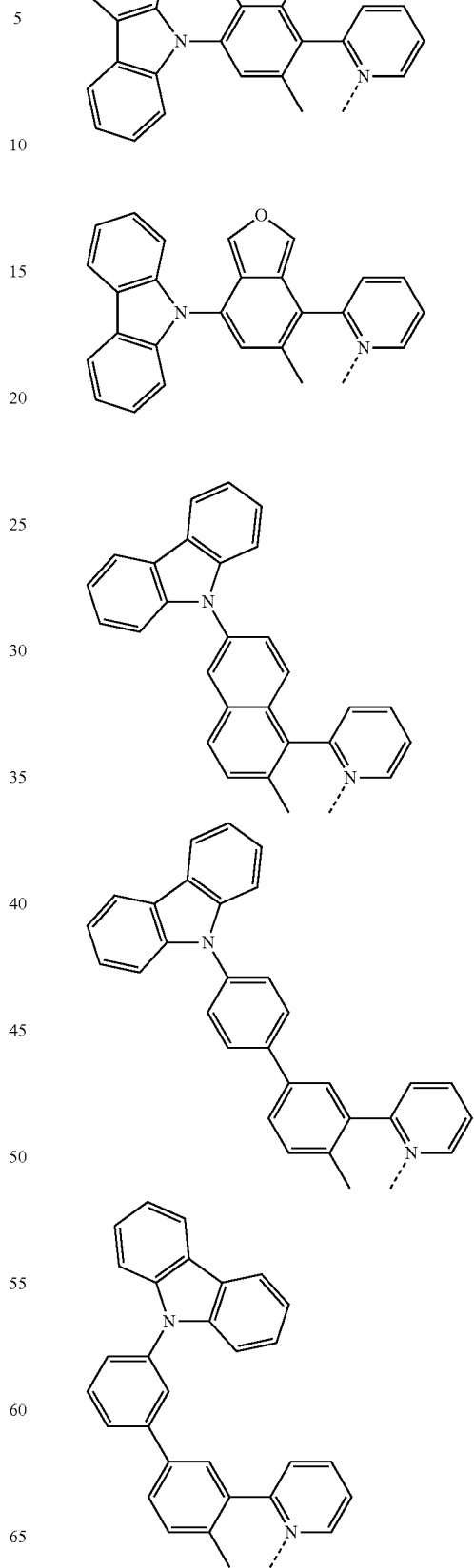

49
-continued
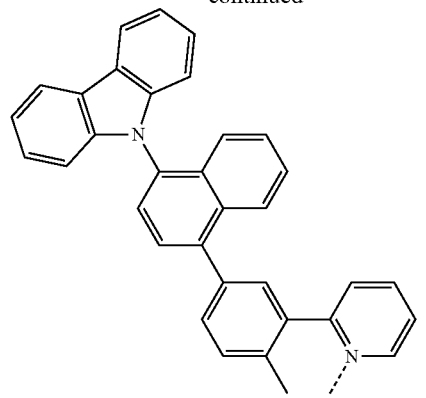
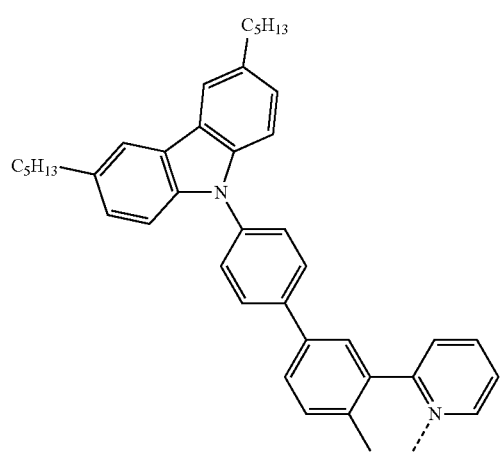
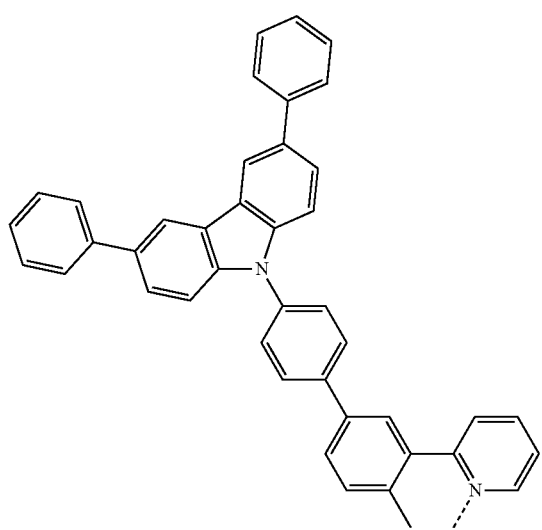
50
-continued
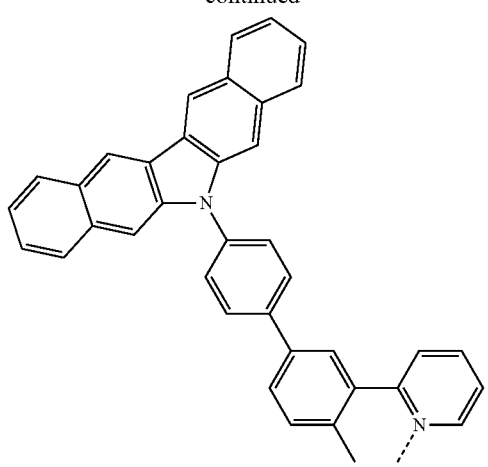
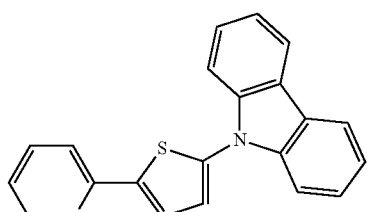
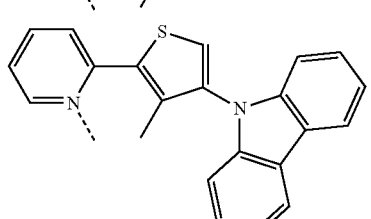
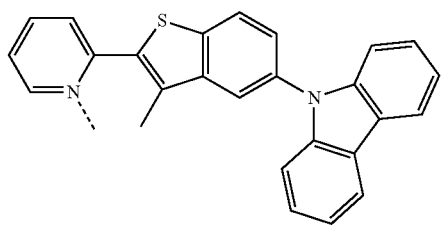
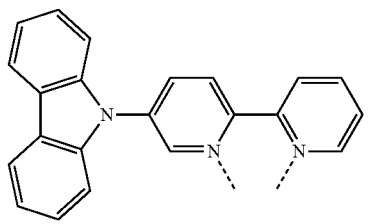
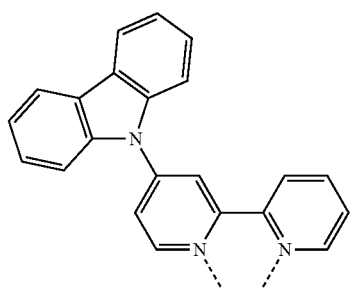

51
-continued
52
-continued
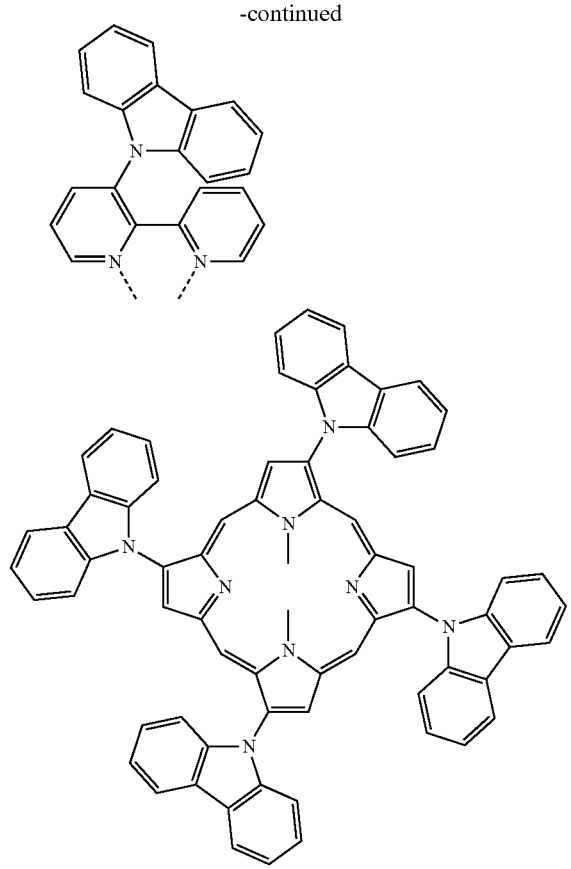
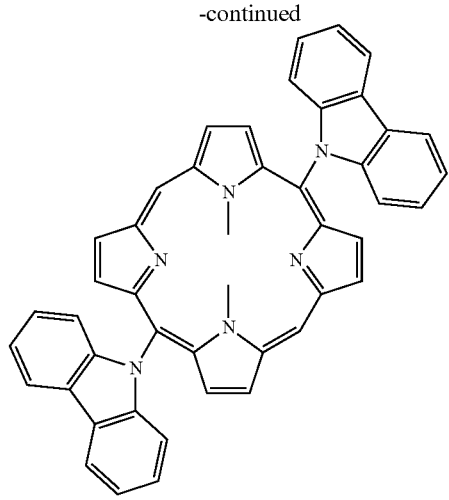
Specific examples of the complex represented by formula (3) is shown below.
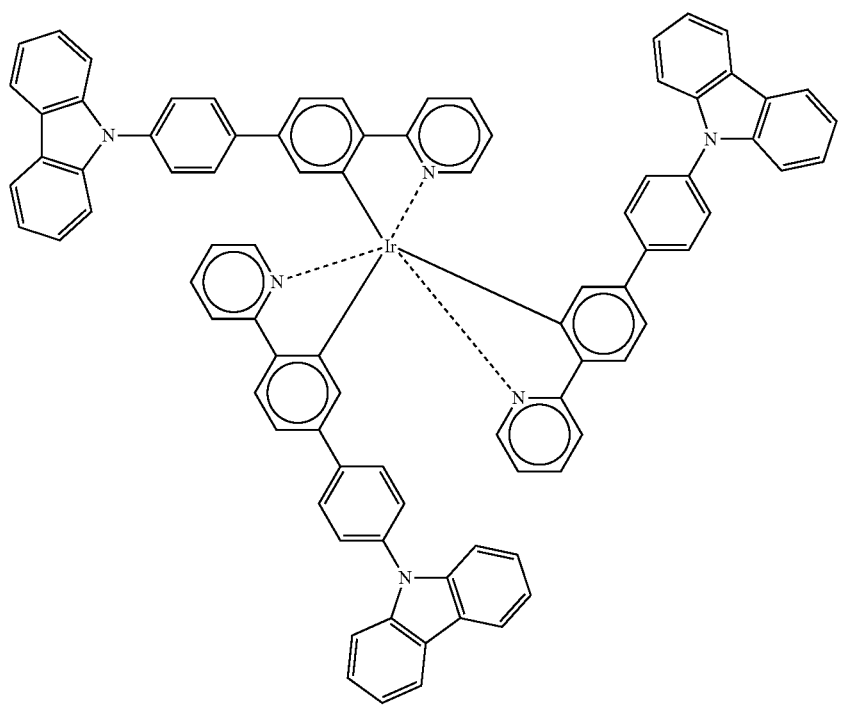

-continued
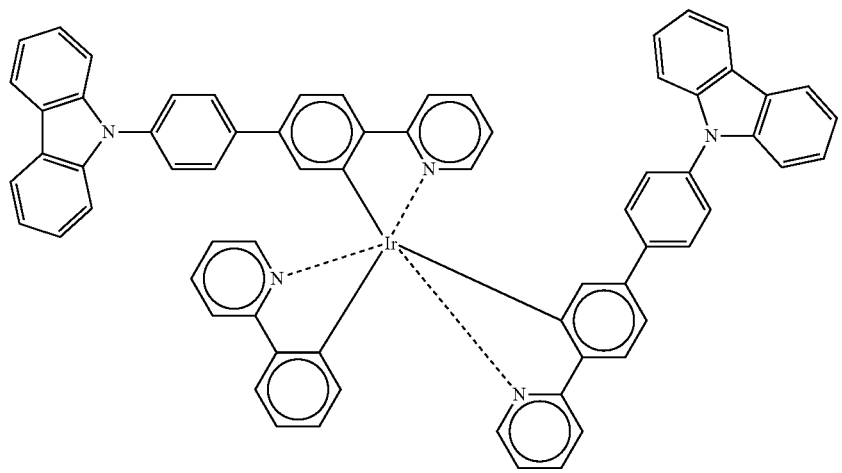
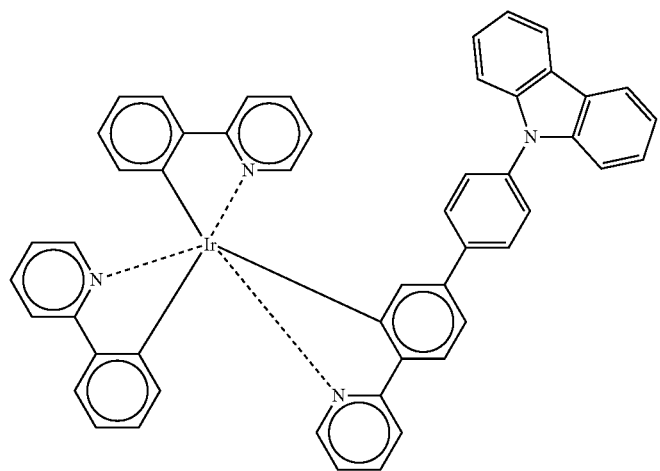
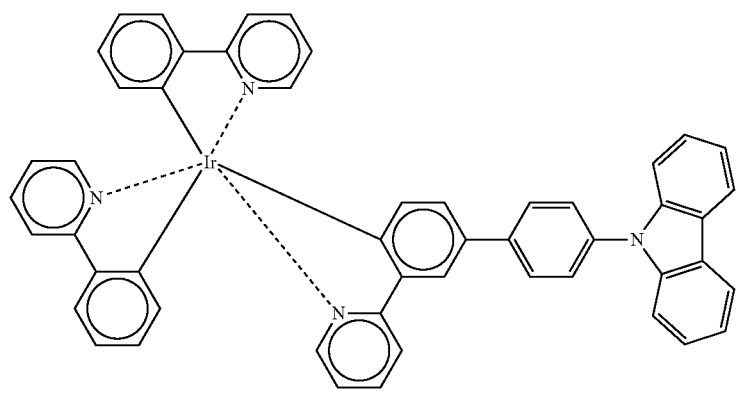

55
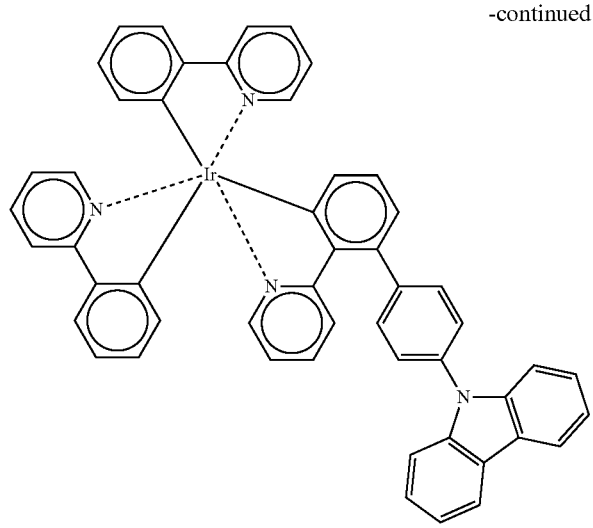
56
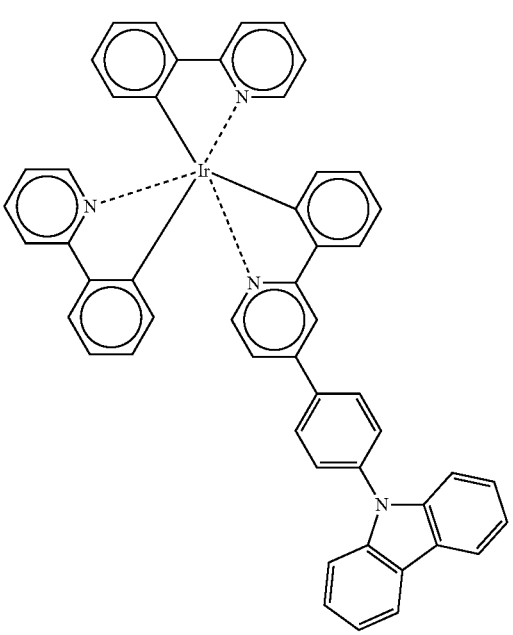
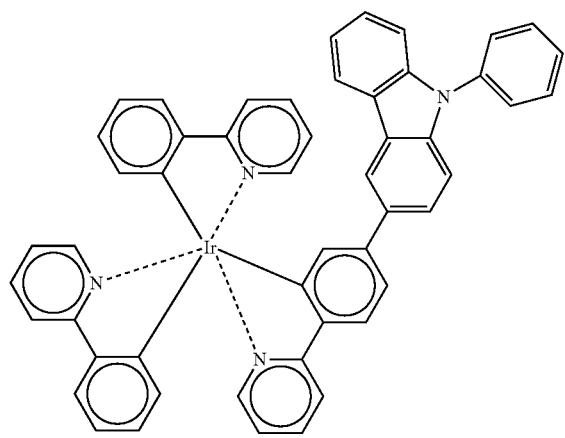
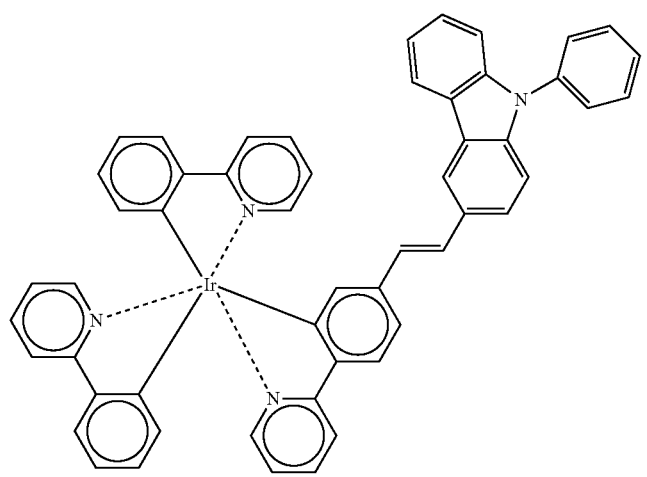

-continued
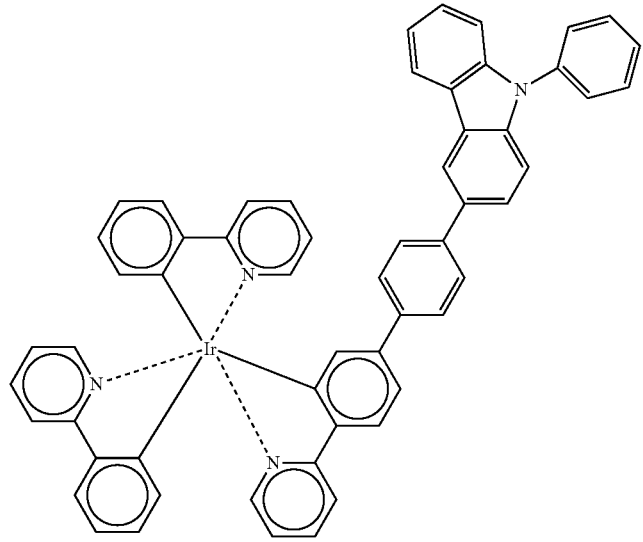
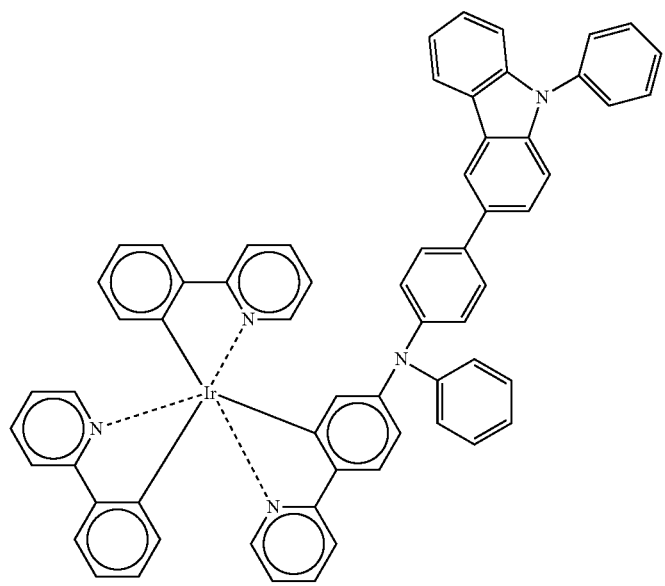
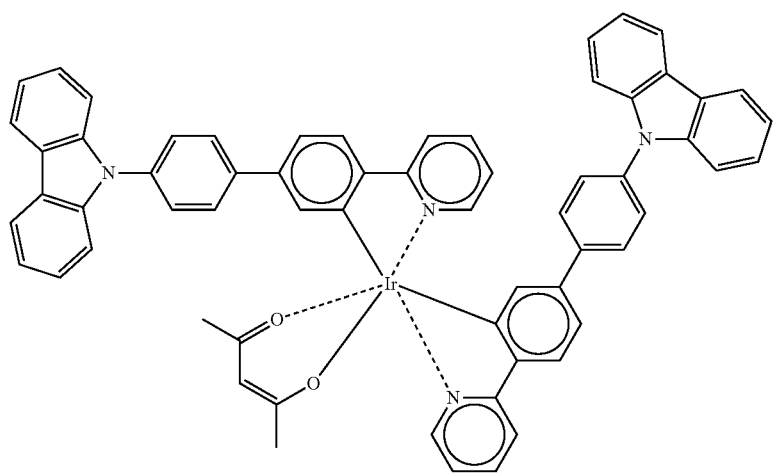

-continued
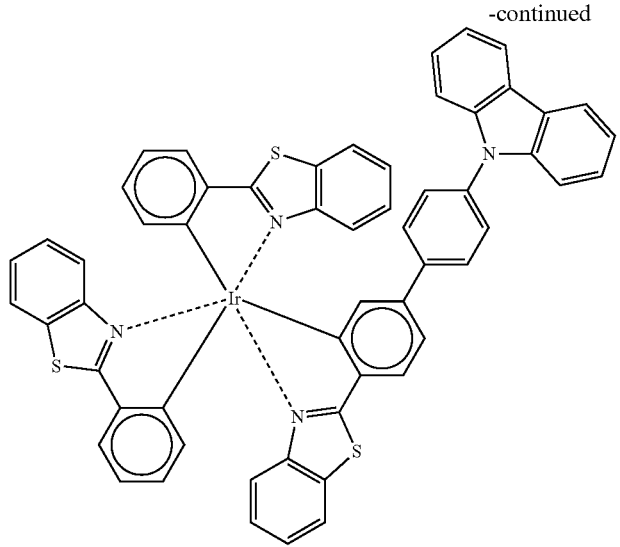
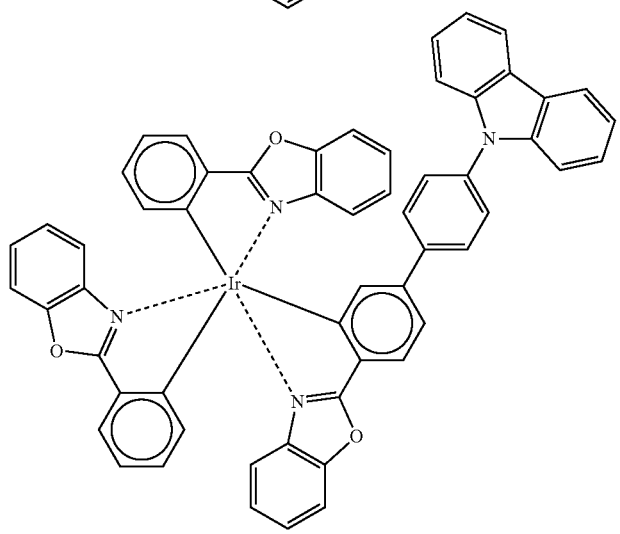
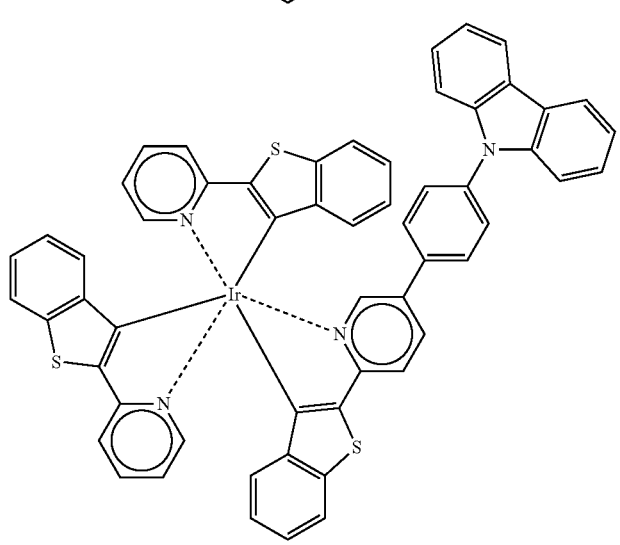
The complexes represented by the above formula (3) can be manufactured, for example, by a condensation reaction of a complex represented by the below formula (17) with a carbazole derivative represented by the below formula (18) or (19).

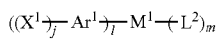 (17)

(Here, $M^1$, $Ar^1$, $L^2$, l, and m are the same as those of the above. $x^1$ represents a halogen atom, sulfonate group, boric acid group, boric ester group, sulfonium methyl group, phosphonium methyl group, phosphonate methyl group, monohalogenated methyl group, formyl group, cyano group, or vinyl group.)

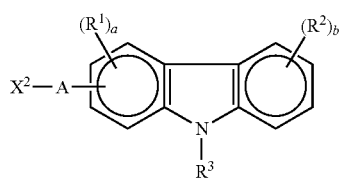 (18)

(Here, A, $R^1$, $R^2$, $R^3$, a, and b are the same as those of the above. $x^2$ represents a halogen atom, sulfonate group, boric acid group, boric ester group, sulfonium methyl group, phosphonium methyl group, phosphonate methyl group, monohalogenated methyl group, formyl group, cyano group, or vinyl group.)

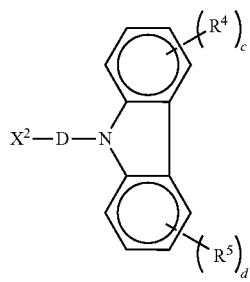 (19)

(Here, D, $Ar^3$, $R^4$, $R^5$, c, d, e, and $x^2$ are the same as those of the above.

As the halogen atom in $x^1$ and $x^2$, chlorine, bromine, and iodine are exemplified.

As the sulfonate group, benzene sulfonate group, p-toluene sulfonate group, methane sulfonate group, ethane sulfonate group, and trifluoromethane sulfonate group are exemplified.

As the boric ester group, groups represented by the below formulae are exemplified.

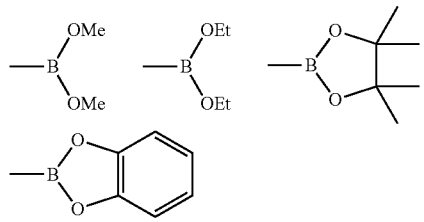

As the sulfonium methyl group, groups represented by the below formulae are exemplified.

—$CH_2SMe_2X$

—$CH_2SPh_2X$ (X Represents a Halogen Atom.)

As the phosphonium methyl group, a group represented by the below formula is exemplified.

 (X represents a halogen atom.)

As the phosphonate methyl group, a group represented by the below formula is exemplified

(R' represents an alkyl group, aryl group, or arylalkyl group.)

As the monohalogenated methyl group, chloromethyl group, bromomethyl group, and iodomethyl group are exemplified.

Examples of the condensation through a vinylene group include reactions such as: Wittig reaction of a compound having formyl group with a compound having phosphonium methyl group, or a compound having formyl group and phosphonium methyl group;

Heck reaction of a compound having vinyl group with a compound having halogen atom; Knoevenagel reaction of a compound having formyl group with a compound having cyano group; and McMurry reaction of a compound having formyl group, etc.

Examples of the formation of a single bond include Suzuki coupling, and Grignard coupling with using nickel catalyst.

The reactions can be carried out by solving in a organic solvent according to the necessity, with using alkali or an appropriate catalyst, at a temperature of from the melting point to the boiling point.

Known methods can be used described in: Organic Reactions, vol. 14, page 270-490, John Wiley & Sons, Inc. (1965); Organic Syntheses, Collective Volume VI, page 407-411, John Wiley & Sons, Inc. (1988); Chem. Rev., vol. 95, page 2457 (1995); J. Organomet. Chem., vol. 576, page 147 (1999); J. Prakt. Chem., vol. 336, page 247 (1994); Makromol. Chem., Macromol. Symp., vol. 12, page 229 (1987), etc.

They can be prepared also by a method of complex formation after synthesizing a ligand. As the synthetic method of the ligand, for example, it can be manufactured by a condensation reaction of a compound represented by the below formula (20) with a carbazole derivative represented by the above formula (18) or (19). Examples of the condensation reaction are the same as those of the coupling reaction of a complex represented by the above formula (17) with a carbazole derivative represented by the above formula (18) or (19).

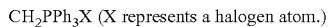 (20)

(Here, $Ar^1$ and $x^1$ are the same as those of the above.)

Examples of the method of complex formation from the above formula (20) include: in the case of an iridium complex, methods described in Inorg. Chem. 1991, 30, 1685 and Inorg. Chem. 2001, 40, 1704, etc.; in the case of a platinum complex, methods described in Chem. Mater. 1999, 11, 3709; in the case of an europium complex, methods described in J. Polymer Science, Part A, 2000, 38, 3405; and in the case of a ruthenium complex, methods described in Polymer Bulletin, 1999, 43, 135 and J. Mater. Chem., 1999, 9, 2103.

It is preferable that the organic solvent used is subjected to a deoxygenation treatment sufficiently and the reaction is progressed under an inert atmosphere, generally for suppressing a side reaction, though the treatment differs depending on the compound used and the reaction. Further, it is preferable to conduct a dehydration treatment likewise. However, this is not applicable in the case of a reaction in a two-phase system with water, such as a Suzuki coupling reaction.

For the reaction, an alkali or suitable catalyst is added appropriately. These may be selected according to the reaction used. It is preferable that the alkali or catalyst is soluble sufficiently in a solvent used for the reaction. As the method of mixing an alkali or catalyst, there is exemplified a method of adding a solution of an alkali or catalyst slowly while stirring under an inner atmosphere of argon and nitrogen and the like or a method of slowly adding the reaction solution to a solution of an alkali or catalyst, inversely.

Although the reaction temperature is not limited, it is usually about −100 to 350° C., and preferably from 0° C. to the boiling point of solvent. Although the reaction time is not limited, it is usually about 30 minutes to 30 hours.

About the extraction and purification of the desired product from a solution of reaction mixture, it differs depending on the complexes, but techniques of usual complex purification, such as recrystallization, sublimation, and chromatography, are used.

For example, 1N HCl aqueous solution which is a poor solvent to a complex, is added to deposit the complex, and filtrated to obtain a solid, which is dissolved into an organic solvent, such as dichloromethane or chloroform. This solution is filtrated to remove insoluble materials, concentrated again, and purified by silica gel column chromatography (dichloro methane elution). The fraction solutions of the desired product are collected, and for example, methanol (poor solvent) is added in an appropriate amount, and concentrated to deposit the desired complex, which is filtrated, and dried, and the complex is obtained. The method of producing complex (3) of the present invention is not limited to the above method.

For example, the complex of the present invention represented by the below formula (A) can be produced by the following synthetic route.

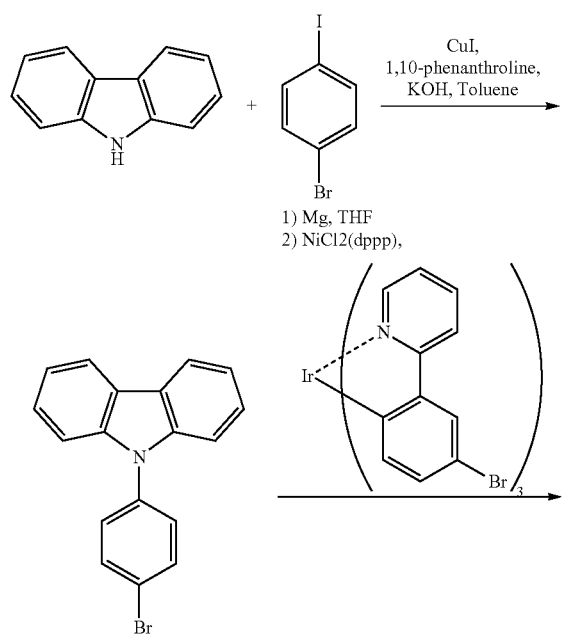

(A)

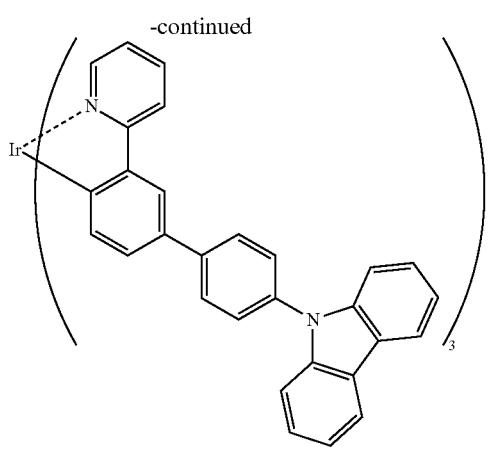

The polymeric light emitting substance of the present invention may have a metal complex structure showing light emission from triplet excited state in the main chain, in the side chain, or at the terminal of the main chain.

The polymeric light emitting substance having a metal complex structure showing light emission from triplet excited state in the main chain means the case wherein an aromatic ring part or condensed ring part which coordinate to the complex showing light emission from triplet excited state is contained in the main chain, or the case wherein a metal is contained in the main chain.

Specific examples of the metal complex structure showing light emission from triplet excited state in the a main chain include the repeating unit represented by the below formulas (8) and (9).

(8)

In the formula, $M^2$ is an atom having atomic number of 50 or more, spin-orbit interaction occurs in the complex, and intersystem crossing between a singlet state and a triplet state can occur in the metal.

$L^3$ represents a ligand represented by the below formula (12) or (13). $L^4$ represents: a ligand which bonds to $M^2$ with one or more of nitrogen atom, oxygen atom, carbon atom, sulfur atom, or phosphorus atom; a halogen atom; or a hydrogen atom. e represents an integer of 1-3. f represents an integer of 0-3. $L^5$ is a ligand which bonds to $M^2$ with one or more of nitrogen atom, oxygen atom, carbon atom, sulfur atom, or phosphorus atom, and has two bonds connected to two neighboring repeating units with covalent bonding. When e is two or more, a plurality of $L^3$ may be the same or different. When f is two or more, a plurality of $L^4$ may be the same or different. Moreover, e+f is an integer of 1-5.

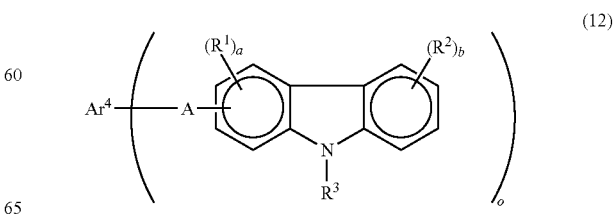

(12)

(in the formula, $Ar^4$ is a residue of the ligand which bonds to $M^2$ with one or more nitrogen atom, oxygen atom, carbon atom, sulfur atom, or phosphorus atom, and bonds to o pieces of As. o represents an integer of 1-3. A, $R^1$-$R^3$, a and b are respectively the same as those in the above formula (1).)

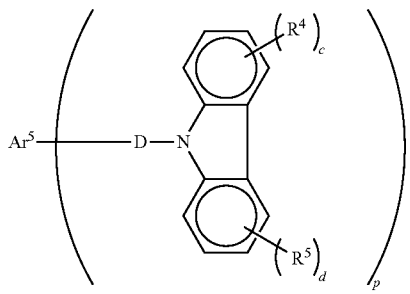

(13)

(In the formula, $Ar^5$ is a residue of the ligand which bonds to $M^2$ with one or more nitrogen atom, oxygen atom, carbon atom, sulfur atom, or phosphorus atom, and has covalent bonds to p pieces of Ds. p represents an integer of 1-3. D, $R^4$, $R^5$, c, and d are respectively the same as those in the above formula (2).)

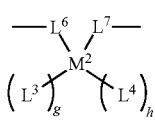

(9)

(In the formula, $M^2$, $L^3$, and $L^4$ are the same as above. $L^6$ and $L^7$ are each independently, a ligand which bonds to $M^2$ with one or more nitrogen atom, oxygen atom, carbon atom, sulfur atom, or phosphorus atom, and has a covalent bond to one neighboring repeating unit with one free bond, respectively. g represents an integer of 1-3 and h represents an integer of 0-3. When g or h is two or more, $L^3$s or $L^4$s may be the same or different. Moreover, g+h is an integer of 1-4.)

As the metal complex structure showing light emission from triplet excited state at the side chain, repeating units represented by the below formula (10) are specifically exemplified.

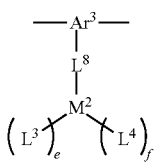

(10)

(In the formula, $M^2$, $L^3$, $L^4$, e, and f are the same as those in the above formula (8). $Ar^3$ is a trivalent aromatic group or a trivalent heterocyclic group. $L^8$ is a ligand which bonds to $M^2$ with one or more nitrogen atom, oxygen atom, carbon atom, sulfur atom, or phosphorus atom, and has a covalent bond to $Ar^3$ with one free bond.)

As the metal complex structure showing light emission from triplet excited state at the terminal of the main chain, repeating units represented by the below formula (11) are specifically exemplified.

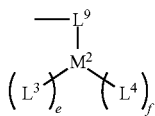

(11)

(In the formula, $M^2$, $L^3$, $L^4$, e, and f are the same as those in the above formula (8). $L^9$ is a ligand which bonds to $M^2$ with one or more nitrogen atom, oxygen atom, carbon atom, sulfur atom, or phosphorus atom, and has a covalent bond at the polymer terminal with one free bond.)

Moreover, a metal complex structure showing light emission from triplet excited state may be contained, and further a monovalent group represented by the above formula (1) or (2) may be contained on a repeating unit other than said metal complex structure.

Examples of the atom represented by $M^2$ include rhenium atom, osmium atom, iridium atom, platinum atom, gold atom, lanthanum atom, cerium atom, praseodymium atom, neodymium atom, promethium atom, samarium atom, europium atom, gadolinium atom, terbium atom, and dysprosium atom. Rhenium atom, osmium atom, iridium atom, platinum atom, gold atom, samarium atom, europium atom, gadolinium atom, terbium atom, and dysprosium atom are preferable, and iridium atom, platinum atom, gold atom, and europium atom are more preferable.

Examples of the ligand which bonds to $M^2$ with one or more nitrogen atom, oxygen atom, carbon atom, sulfur atom, or phosphorus atom include an alkyl group, alkoxy group, acyloxy group, alkylthio group, alkylamino group, aryl group, aryloxy group, arylthio group, arylamino group, arylalkyl group, arylalkoxy group, arylalkylthio group, arylalkyl amino group, sulfonate group, cyano group, heterocyclic ligand, carbonyl compound, ether, amine, imine, phosphine, phosphite, and sulfide, and multi-dentate ligand derived from combination thereof. Specifically, the compounds described in $L^2$ are exemplified.

The trivalent heterocyclic group in the present invention means an atomic group in which three hydrogen atoms are removed from a heterocyclic compound, and usually has 4 to 60, and preferably 4 to 20 carbon atoms. The number of carbon atoms of a substituent is not counted as the number of carbon atoms of the trivalent aromatic compound.

Specific examples thereof include groups described in A and D wherein a hydrogen atom is removed from the groups exemplified as a divalent heterocyclic group.

The polymeric compound of the present invention may have two or more kinds of repeating units represented by the above formula (8)-(10). The amount of these repeating units is usually 0.01-50% by mole to the total moles of all repeating units, and preferably 0.1-10% by mole.

Examples of the metal complex structure showing light emission from triplet excited state in the main chain, include specifically the following structures.

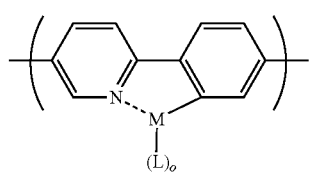

67
-continued
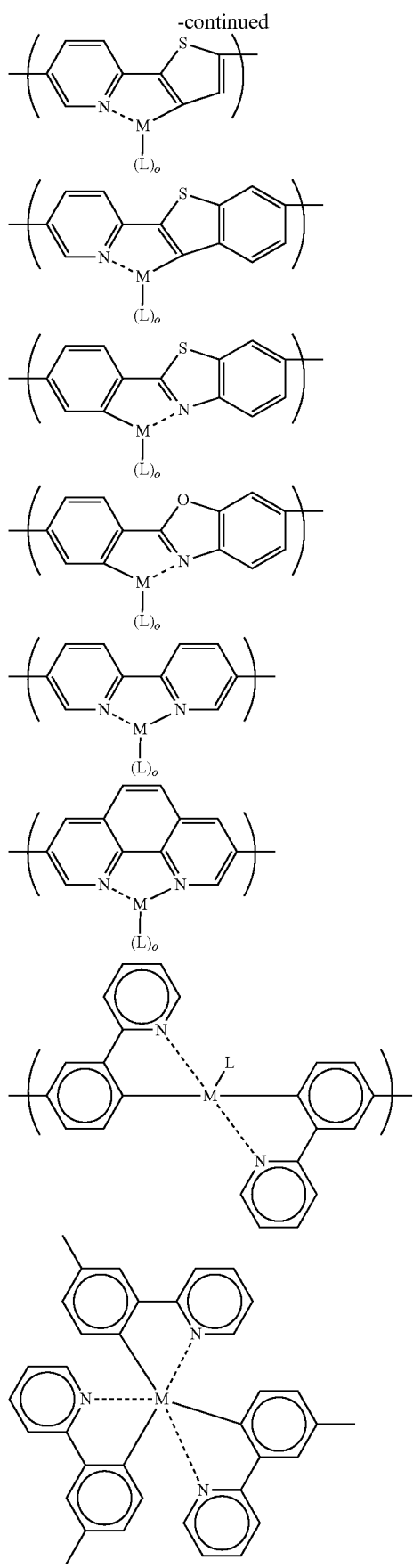
68
-continued
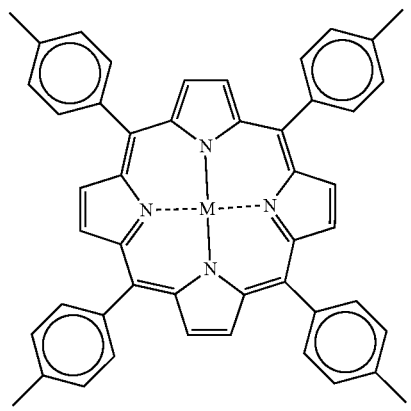
Moreover, examples of the case contained at the terminal of the main chain, include the following structures.
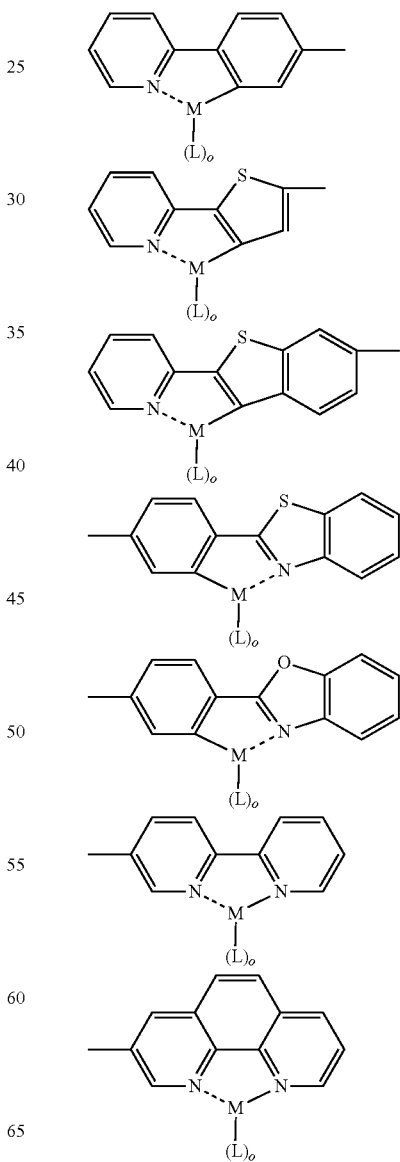

-continued

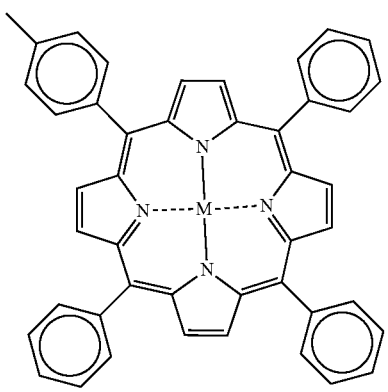

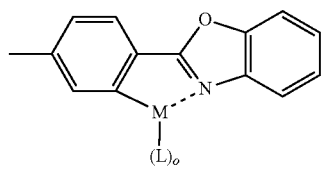

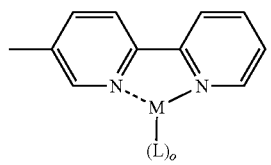

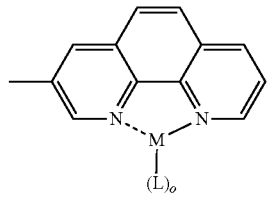

The polymeric light emitting substance having a metal complex structure showing light emission from triplet excited state in the side chain means the case wherein an aromatic ring part or condensed ring part which coordinate to the complex showing light emission from triplet excited state is connected to the main chain through bonding. Here, the bond means a direct bond such as a direct bond and a double bond; a bond through an atom, such as oxygen atom, sulfur atom, and selenium atom; or a bond through a divalent-bond such as a methylene group, alkylene group, and arylene group, etc.

Among them, it is preferable that a metal complex structure showing light emission from triplet excited state is contained in a side chain having conjugated bonding, and it is more preferable that an aromatic ring contained in at least one ligand of said metal complex structure and an aromatic ring contained in the polymer main chain are connected through a carbon-carbon single bond.

Specifically, following structures are exemplified. The free bond is a bonding group to the main chain.

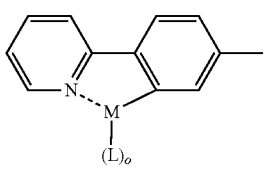

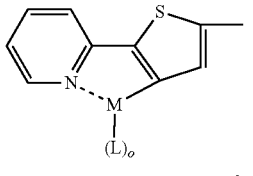

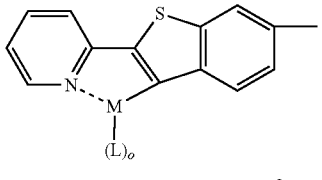

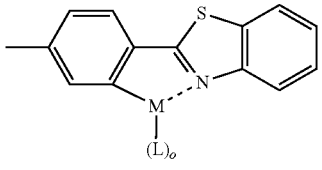

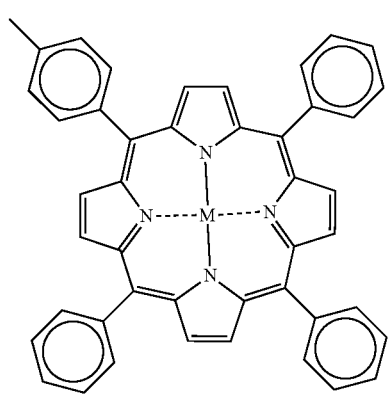

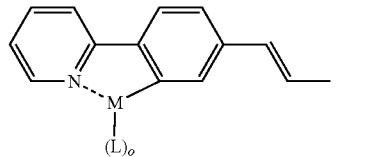

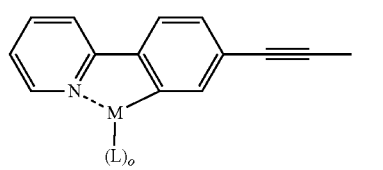

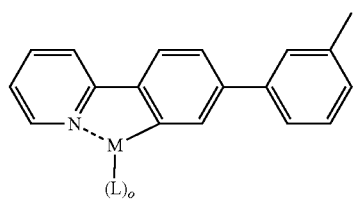

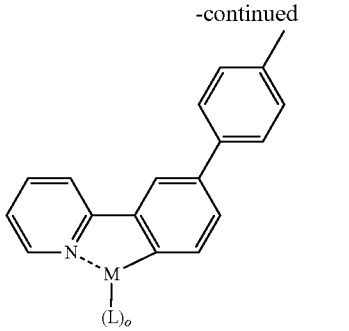
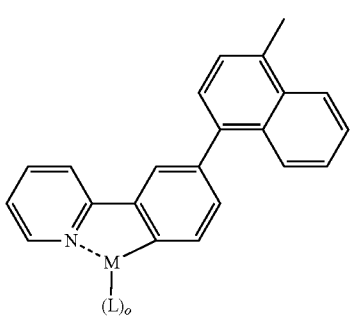
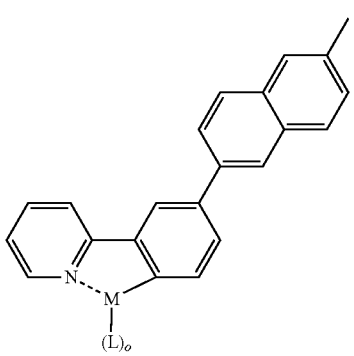
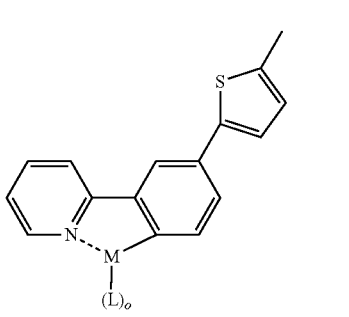
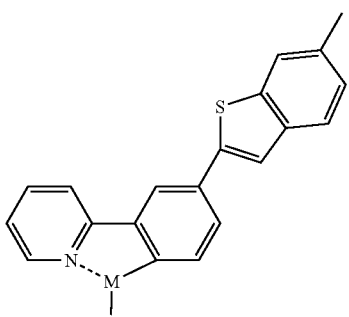

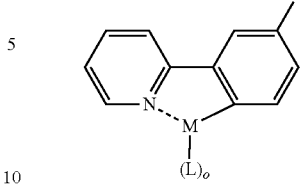

In the above formula, M is an atom having atomic number of 50 or more, spin-orbit interaction occurs in the complex, and intersystem crossing between a singlet state and a triplet state can occur in the metal.

L is a ligand of M, and represents an alkyl group, alkoxy group, alkylthio group, alkylamino group, aryl group, aryloxy group, arylthio group, arylamino group, arylalkyl group, arylalkoxy group, arylalkylthio group, arylalkylamino group, sulfonate group, heterocyclic group, acyloxy group, cyano group, heterocyclic ligand, carbonyl compound, ether, amine, imine, phosphine, phosphite, or sulfide, and may be a multidentate ligand derived from the combination thereof.

o represents an integer of 1-5. When o is two or more, Ls may be mutually the same, or different.

Examples of the atom represented by M include: rhenium atom, osmium atom, iridium atom, platinum atom, gold atom, lanthanum atom, cerium atom, praseodymium atom, neodymium atom, promethium atom, samarium atom, europium atom, gadolinium atom, terbium atom, dysprosium atom, etc.; preferably, rhenium atom, osmium atom, iridium atom, platinum atom, gold atom, samarium atom, europium atom, gadolinium atom, terbium atom, and dysprosium atom; and more preferably, iridium atom, platinum atom, gold atom, and europium atom.

The ligand represented by L may be zero-valent, monovalent or more. In the group represented by L, examples of alkyl group, alkoxy group, alkylthio group, alkylamino group, aryl group, aryloxy group, arylthio group, arylamino group, arylalkyl group, arylalkoxy group, arylalkylthio group, arylalkylamino group, heterocyclic group, acyloxy group, carbonyl compound, ether, amine, imine, phosphine, phosphite, and sulfide, include the compounds described in the above $R^2$.

Of the polymeric light-emitting substance of the present invention, it is preferable that the main chain is a conjugated type polymeric light-emitting substance. Here, the conjugated type polymeric light-emitting substance means a polymeric light-emitting substance in which delocalized π electron pair exist along with the main-chain of the polymer, i.e., a polymeric light-emitting substance whose main chain is a conjugated polymer. As this delocalized electron, a unpaired electron or a lone electron pair may join to the resonance instead of a double bond.

One embodiment of the present invention is a polymeric light-emitting substance having two or more kinds of metal complex structures showing light emission from triplet excited state, i.e., a polymeric light-emitting substance having 2 or more kinds of metal complex structures showing light emission from triplet excited state, on two or more of the main chain, side chain, or the terminal. Metal complex structures may have the same metal each other, and may have different metals. Moreover, metal complex structures may have mutually different light emission color. For example, exemplified is a case where both of a metal complex structure which emits green light and a metal complex structure which emits red light are contained in one polymeric light-emitting substance. The case is preferable, since a light emission color is controllable by designing to contain an appropriate amount of the metal complex structure.

As for the polymeric light-emitting substance of the present invention, it is preferable that the repeating unit represented by the below formula (14) is contained.

  (14)

(In the formula, $Ar^6$ represents an arylene group or a divalent heterocyclic group. These groups may have a substituent. $R^{20}$ and $R^{21}$ each independently represent a hydrogen atom, alkyl group, aryl group, arylalkyl group, arylalkenyl group, arylalkynyl group, monovalent heterocyclic group, cyano group, and a group represented by the above formula (1) or formula (2). At least one of $R^{20}$, $R^{21}$, or the substituents on $Ar^6$, represents a group represented by the above formula (1) or (2). n is 0 or 1.)

As the alkyl group, aryl group, and monovalent heterocyclic group represented by $R^{20}$ or $R^{21}$, exemplified are the same as those of the above R.

As the arylene group and divalent heterocyclic group represented by $Ar^6$, exemplified are the same as those of the above A or D.

As for the polymeric light-emitting substance of the present invention, it is preferable that the repeating unit represented by the below formula (21) is included in respect of light emitting efficiency.

  (21)

(In the formula, $Ar^7$ and $Ar^8$ each independently represent an arylene group or a divalent heterocyclic group. $R^{36}$ represents alkyl group, aryl group, monovalent heterocyclic group, a group represented by the above formula (1), a group represented by the above formula (2), a group represented by the following formula (22), or a group represented by the following formula (23). t is an integer of 1-4.)

  (22)

(In the formula, $Ar^9$ is an arylene group or a divalent heterocyclic group. $R^{37}$ is a hydrogen atom, alkyl group, aryl group, monovalent heterocyclic group, or a group represented by the below formula (23). $Z^1$ represents $-CR^{38}=CR^{39}-$ or $-C\equiv C-$. $R^{38}$ and $R^{39}$ each independently represent a hydrogen atom, alkyl group, aryl group, a monovalent heterocyclic group, a group represented by the above formula (1), a group represented by the above formula (2), or cyano group. u is an integer of 0-2.)

  (23)

(In the formula, $Ar^{10}$ and $Ar^{11}$ each independently represent an arylene group or a divalent heterocyclic group. $R^{40}$ represents an alkyl group, aryl group, a group represented by the above formula (1), a group represented by the above formula (2), or a monovalent heterocyclic group. $R^{41}$ represents a hydrogen atom, alkyl group, aryl group, or monovalent heterocyclic group. v is an integer of 1-4.)

As the arylene group and divalent heterocyclic group in $Ar^7$ to $Ar^{11}$, exemplified are the same as those of the above $Ar^1$.

As the alkyl group, aryl group and monovalent heterocyclic group in $R^{36}$ to $R^{41}$, exemplified are the same as those of the above R.

As the preferable example of the repeating unit represented by the above formula (21), exemplified are those represented by the following formulae.

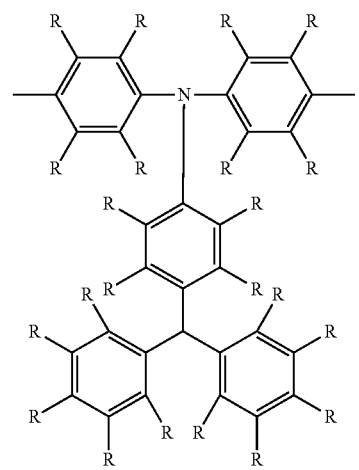

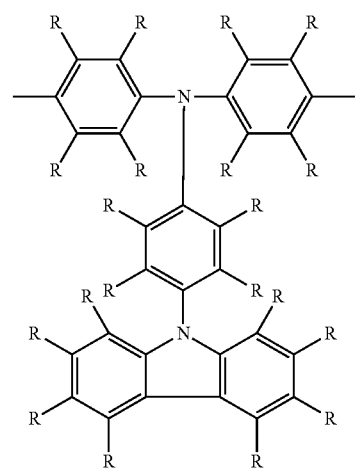

75
-continued
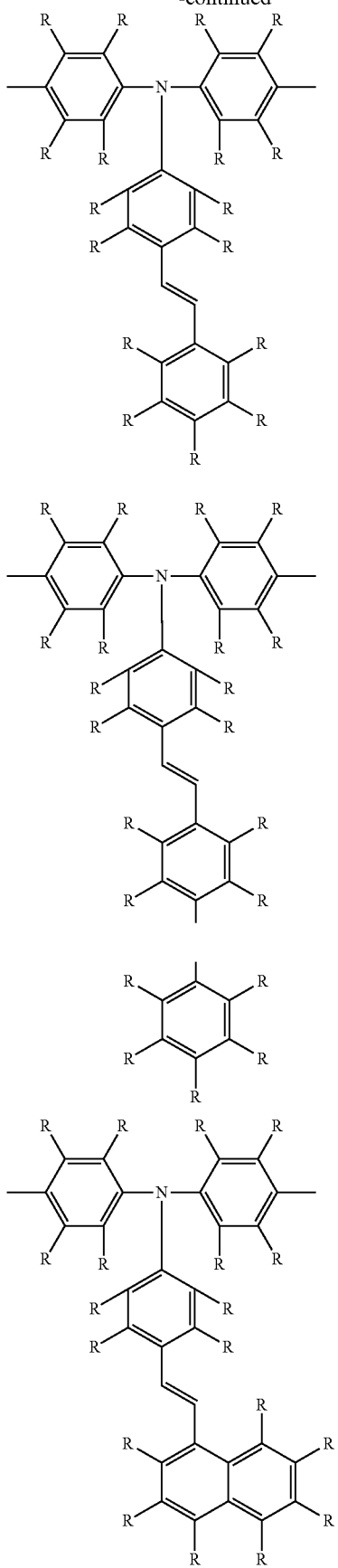
76
-continued
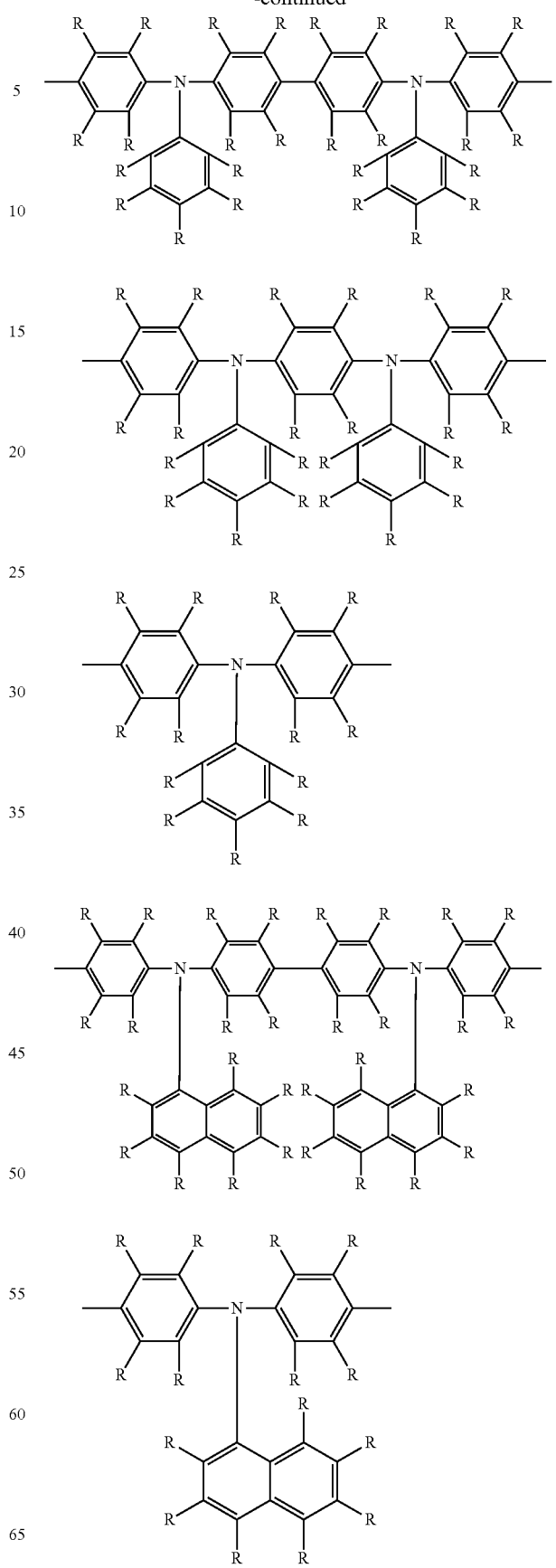

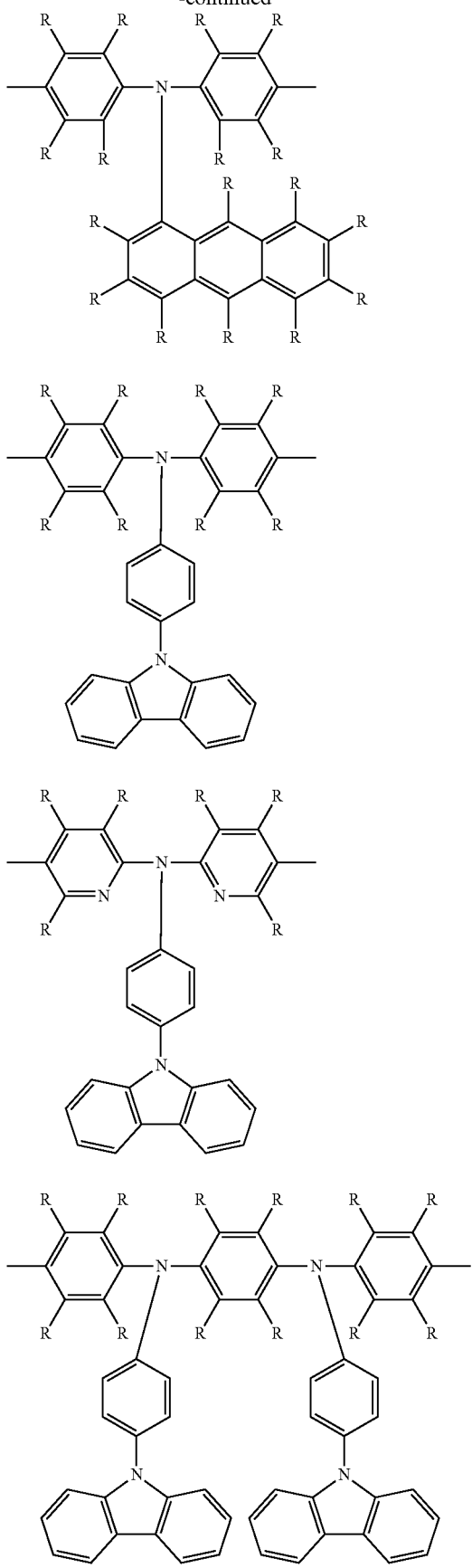
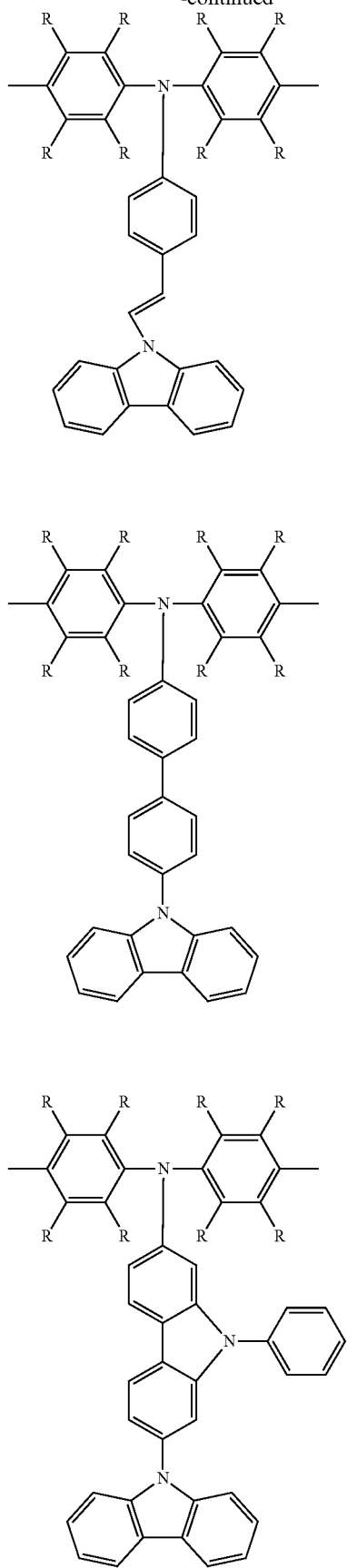

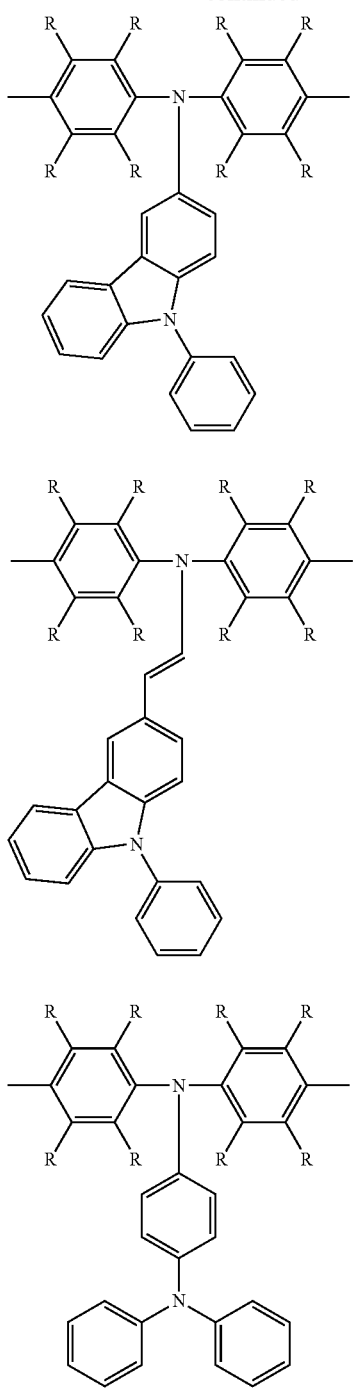

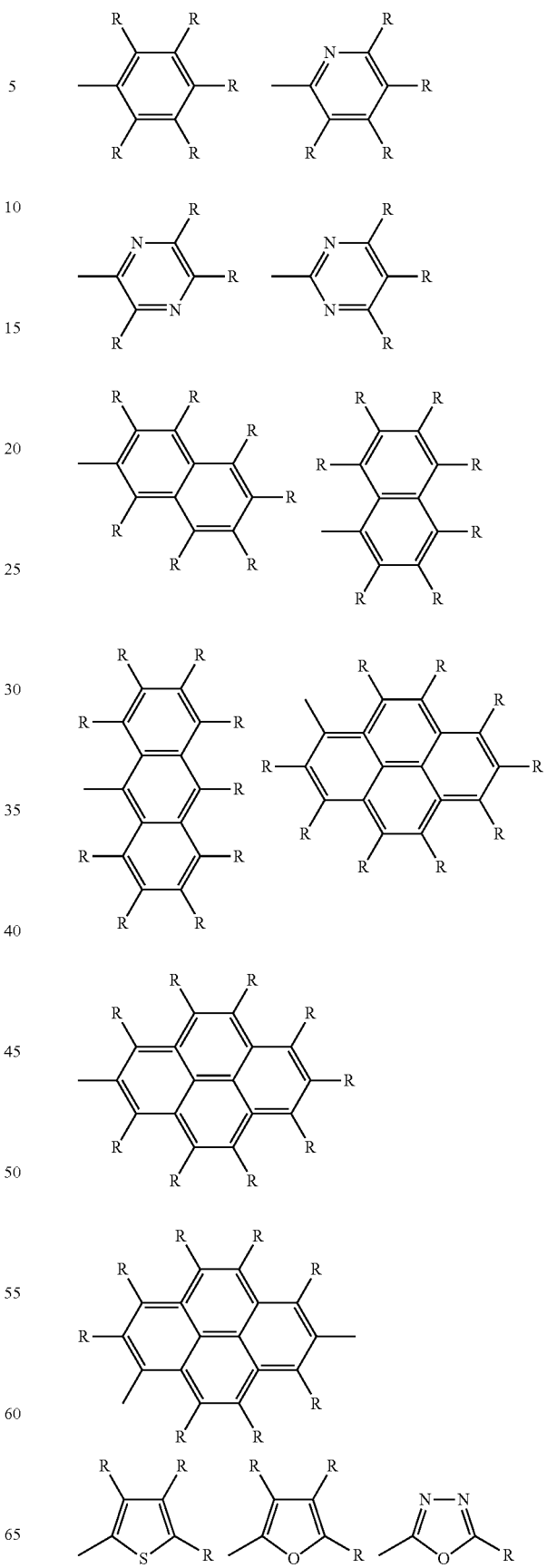

(In the Formula, R is the Same as that of the Above.)

Furthermore, the end group of polymeric compound may also be protected with a stable group since if a polymerization active group remains intact, there is a possibility of reduction in light emitting property and life-time when made into an device. Those having a conjugated bond continuing to a conjugated structure of the main chain are preferable, and there are exemplified structures connected to an aryl group or heterocyclic compound group via a carbon-carbon bond. Specifically, the following structures are exemplified. (In the formula, R is the same as that of the above.)

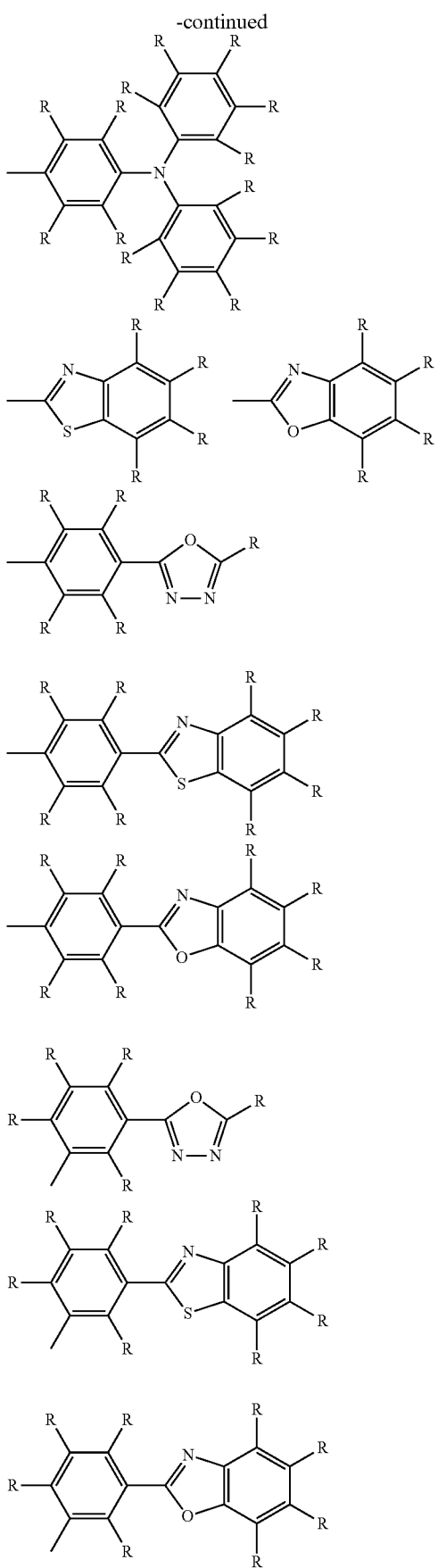
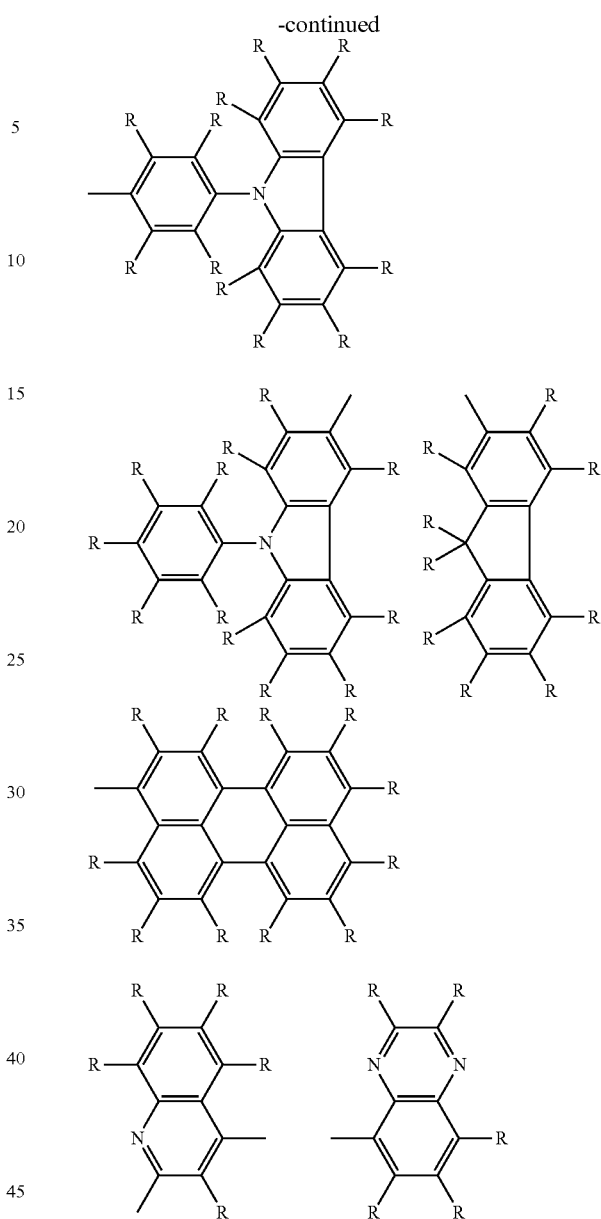

The polymer of the present invention may also be a random, block or graft copolymer, or a polymer having an intermediate structure thereof, for example, a random copolymer having block property. From the viewpoint for obtaining a polymeric fluorescent substance having high fluorescent quantum yield, random copolymers having block property and block or graft copolymers are more preferable than complete random copolymers. Further, a polymer having a branched main chain and more than three terminals, and a dendrimer may also be included.

Furthermore, it is preferable that at least one of the ligands of the metal complex portion showing triplet light emission is a nitrogen atom or a carbon atom in view of the stability of a polymeric light emitting substance. Moreover, it is preferable that at least one of the ligands is a multi-dentate ligand.

It is more preferable that at least one of the ligands is a monovalent ligand represented by the below formula (15) or (16).

(15)

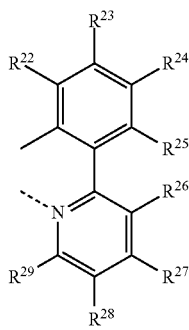

(In the formula, $R^{22}$ to $R^{29}$ each independently represent a hydrogen atom, halogen atom, alkyl group, alkoxy group, alkylthio group, alkylamino group, alkylsilyl group, aryl group, aryloxy group, arylthio group, arylamino group, aryl silyl group, arylalkyl group, arylalkoxy group, arylalkylthio group, arylalkylamino group, arylalkylsilyl group, acyl group, acyloxy group, imino group, amide group, arylalkenyl group, arylalkynyl group, cyano group, or monovalent heterocyclic group, and they may be mutually connected to form a ring. At least one of $R^{22}$ to $R^{29}$ is a free bond with a main chain or a side chain.)

(16)

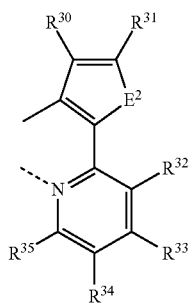

(In the formula, $E^2$ represents an oxygen atom or a sulfur atom. $R^{20}$ to $R^{35}$ each independently represent a hydrogen atom, halogen atom, alkyl group, alkoxy group, alkylthio group, alkylamino group, alkylsilyl group, aryl group, aryloxy group, arylthio group, arylamino group, arylsilyl group, arylalkyl group, aryl alkoxy group, arylalkylthio group, arylalkylamino group, arylalkylsilyl group, acyl group, acyloxy group, imino group, amide group, arylalkenyl group, arylalkynyl group, cyano group, or monovalent heterocyclic, and they may be mutually connected to form a ring. At least one of $R^{30}$ to $R^{35}$ is a free bond with a main chain or a side chain.)

It is more preferable that the central metal of the metal complex portion showing light emission from triplet excited state is an iridium atom, platinum atom, gold atom, or europium atom.

Next, the manufacture method of the polymeric light-emitting substance of the present invention will be explained. The polymeric light-emitting substance of the present invention can be manufactured by a method of copolymerizing a monomer unit having a metal complex structure showing light emission from a triplet state, with a monomer unit having a carbazole group represented by the above formula (1) or (2), or by a method of polymerizing a monomer unit having a carbazole group represented by the above formula (1) or (2) in the ligand, and having a metal complex structure showing light emission from triplet state. Moreover, the monomer unit having a metal complex structure showing light emission from a triplet state, and the monomer unit having a carbazole group represented by the above formula (1) or (2), can be used as two or more kinds thereof, and also can be used for the copolymerization with a monomer unit containing neither the monomer unit having a metal complex structure showing light emission from a triplet state, nor the monomer unit having a carbazole group represented by the above formula (1) or (2).

Specifically, it can be manufactured by carrying out condensation polymerization of two or more monomers represented by the below formulas (24) and (25).

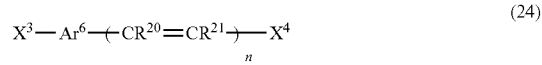

(24)

(In the formula, $Ar^6$, $R^{20}$, $R^{21}$, and n respectively represent the same as those of the above formula (14). $x^3$ and $x^4$ each independently represent a halogen atom, sulfonate group, boric-acid group, boric ester group, sulfonium methyl group, phosphonium methyl group, phosphonate methyl group, monohalogenated methyl group, formyl group, cyano group, or vinyl group.)

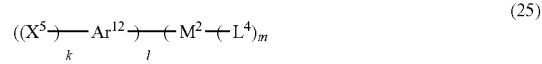

(25)

(In the formula, $M^2$ and $L^4$ are the same as those of the above formula (8). $Ar^{12}$ represents a ligand which connects to $M^2$ with one or more of a nitrogen atom, an oxygen atom, a carbon atom, a sulfur atom, or a phosphorus atom. $X^5$ represents a halogen atom, sulfonate group, boric-acid group, boric ester group, sulfonium methyl group, phosphonium methyl group, phosphonate methyl group, monohalogenated methyl group, formyl group, cyano group, or vinyl group. k represents an integer of 1-3, and l represent an integer of 1-6, and m represents an integer of 0-6.)

As the halogen atom, sulfonate group, boric-acid group, boric ester group, sulfonium methyl group, phosphonium methyl group, phosphonate methyl group, and monohalogenated-methyl group, in $X^3$-$X^5$, exemplified are the compounds of those described in the above $X^1$ and $X^2$.

As the method of reaction, an example of condensation reaction of the above formula (17) with a carbazole derivative represented by (18) or (19) is specifically given.

The polymeric light-emitting substance of the present invention can be manufactured also by a method of forming a complex, after manufacturing a polymeric compound having a structure of the ligand contained in the metal complex structure of the polymeric light-emitting substance in the main chain. In this case, it is preferable as the metal content can be controlled.

Specifically, the following structures are exemplified.

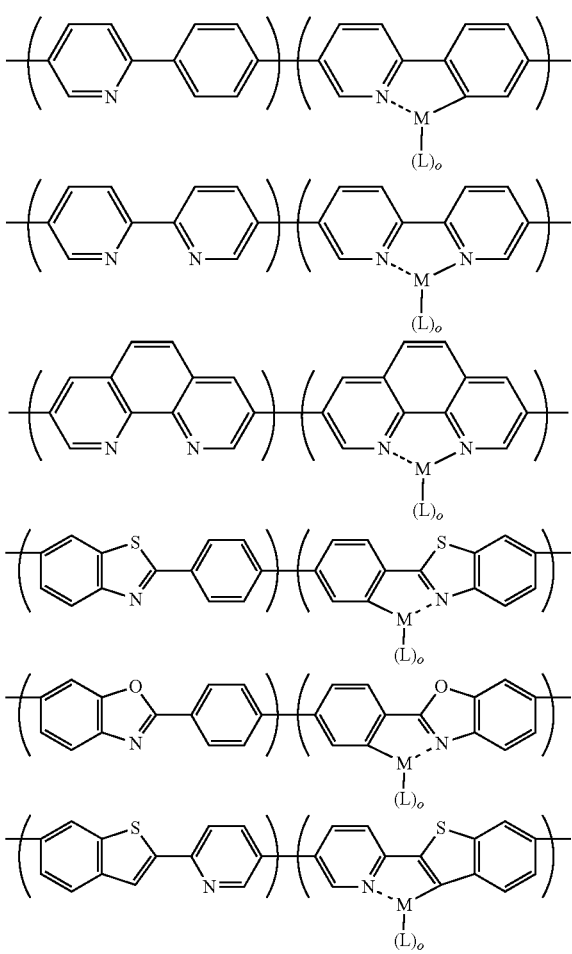

As the method of forming a complex, the same methods of forming a complex from the compound represented by the above formula (20) are exemplified.

It is preferable that the organic solvent used is subjected to a deoxygenation treatment sufficiently and the reaction is progressed under an inert atmosphere, generally for suppressing a side reaction, though the treatment differs depending on compounds and reactions used. Further, it is preferable to conduct a dehydration treatment likewise However, this is not applicable in the case of a reaction in a two-phase system with water, such as a Suzuki coupling reaction.

When these polymeric light-emitting substances of the present invention are used for a light-emitting materials of a polymer LED, the purity thereof exerts an influence on light emitting property, therefore, it is preferable that a monomer is purified by a method such as distillation, sublimation purification, re-crystallization and the like before being polymerized. Further, it is preferable to conduct a purification treatment such as re-precipitation purification, chromatographic separation and the like after the polymerization.

Next, the polymer LED of the present invention will be explained. The polymer LED of the present invention comprises an light emitting layer between the electrodes consisting of an anode and a cathode, and the light emitting layer contains the polymeric light-emitting substance of the present invention.

As the polymer LED of the present invention, exemplified are: a polymer LED having an electron transporting layer between a cathode and a light emitting layer; a polymer LED having an hole transporting layer between an anode and a light emitting layer; and a polymer LED having an electron transporting layer between an cathode and a light emitting layer, and a hole transporting layer between an anode and a light emitting layer.

Also exemplified are: a polymer LED having a layer containing a conductive polymer between at least one of the electrodes and a light emitting layer adjacently to the electrode; and a polymer LED having a buffer layer having a mean thickness of 2 nm or less between at least one of the electrodes and a light emitting layer adjacently to the electrode.

For example, the following structures a) to d) are specifically exemplified.

a) anode/light emitting layer/cathode b) anode/hole transporting layer/light emitting layer/cathode c) anode/light emitting layer/electron transporting layer/cathode d) anode/hole transporting layer/light emitting layer/electron transporting layer/cathode (wherein, "/" indicates adjacent lamination of layers. Hereinafter, the same).

Herein, the light emitting layer is a layer having function to emit a light, the hole transporting layer is a layer having function to transport a hole, and the electron transporting layer is a layer having function to transport an electron. Herein, the electron transporting layer and the hole transporting layer are generically called a charge transporting layer.

The light emitting layer, hole transporting layer and electron transporting layer also may be used each independently in two or more layers.

Of charge transporting layers disposed adjacent to an electrode, that having function to improve charge injecting efficiency from the electrode and having effect to decrease driving voltage of an device are particularly called sometimes a charge injecting layer (hole injecting layer, electron injecting layer) in general.

For enhancing adherence with an electrode and improving charge injection from an electrode, the above-described charge injecting layer or insulation layer having a thickness of 2 nm or less may also be provided adjacent to an electrode, and further, for enhancing adherence of the interface, preventing mixing and the like, a thin buffer layer may also be inserted into the interface of a charge transporting layer and light emitting layer.

The order and number of layers laminated and the thickness of each layer can be appropriately applied while considering light emitting efficiency and life of the device.

In the present invention, as the polymer LED having a charge injecting layer (electron injecting layer, hole injecting layer) provided, there are listed a polymer LED having a charge injecting layer provided adjacent to a cathode and a polymer LED having a charge injecting layer provided adjacent to an anode.

For example, the following structures e) to p) are specifically exemplified.

e) anode/charge injecting layer/light emitting layer/cathode f) anode/light emitting layer/charge injecting layer/cathode g) anode/charge injecting layer/light emitting layer/charge injecting layer/cathode h) anode/charge injecting layer/hole transporting layer/light emitting layer/cathode i) anode/hole transporting layer/light emitting layer/charge injecting layer/cathode j) anode/charge injecting layer/hole transporting layer/light emitting layer/charge injecting layer/cathode k) anode/charge injecting layer/light emitting layer/electron transporting layer/cathode l) anode/light emitting layer/electron transporting layer/charge injecting layer/cathode m) anode/charge injecting layer/light emitting layer/electron transporting layer/charge injecting layer/cathode n) anode/charge injecting layer/hole transporting layer/light emitting layer/electron transporting layer/cathode o) anode/hole transporting layer/light emitting layer/electron transporting layer/charge injecting layer/cathode p) anode/charge injecting layer/hole transporting layer/light emitting layer/electron transporting layer/charge injecting layer/cathode As the specific examples of the charge injecting layer, there are exemplified layers containing an conducting polymer, layers which are disposed between an anode and a hole transporting layer and contain a material having an ionization potential between the ionization potential of an anode material and the ionization potential of a hole transporting material contained in the hole transporting layer, layers which are disposed between a cathode and an electron transporting layer and contain a material having an electron affinity between the electron affinity of a cathode material and the electron affinity of an electron transporting material contained in the electron transporting layer, and the like.

When the above-described charge injecting layer is a layer containing an conducting polymer, the electric conductivity of the conducting polymer is preferably $10^{-5}$ S/cm or more and $10^3$ S/cm or less, and for decreasing the leak current between light emitting pixels, more preferably $10^{-5}$ S/cm or more and $10^2$ S/cm or less, further preferably $10^{-5}$ S/cm or more and $10^1$ S/cm or less.

Usually, to provide an electric conductivity of the conducting polymer of $10^{-5}$ S/cm or more and $10^3$ S/cm or less, a suitable amount of ions are doped into the conducting polymer.

Regarding the kind of an ion doped, an anion is used in a hole injecting layer and a cation is used in an electron injecting layer. As examples of the anion, a polystyrene sulfonate ion, alkylbenzene sulfonate ion, camphor sulfonate ion and the like are exemplified, and as examples of the cation, a lithium ion, sodium ion, potassium ion, tetrabutyl ammonium ion and the like are exemplified.

The thickness of the charge injecting layer is for example, from 1 nm to 100 nm, preferably from 2 nm to 50 nm.

Materials used in the charge injecting layer may properly be selected in view of relation with the materials of electrode and adjacent layers, and there are exemplified conducting polymers such as polyaniline and derivatives thereof, polythiophene and derivatives thereof, polypyrrole and derivatives thereof, poly(phenylene vinylene) and derivatives thereof, poly(thienylene vinylene) and derivatives thereof, polyquinoline and derivatives thereof, polyquinoxaline and derivatives thereof, polymers containing aromatic amine structures in the main chain or the side chain, and the like, and metal phthalocyanine (copper phthalocyanine and the like), carbon and the like.

The insulation layer having a thickness of 2 nm or less has function to make charge injection easy. As the material of the above-described insulation layer, metal fluoride, metal oxide, organic insulation materials and the like are listed. As the polymer LED having an insulation layer having a thickness of 2 nm or less, there are listed polymer LEDs having an insulation layer having a thickness of 2 nm or less provided adjacent to a cathode, and polymer LEDs having an insulation layer having a thickness of 2 nm or less provided adjacent to an anode.

Specifically, there are listed the following structures q) to ab) for example.

q) anode/insulation layer having a thickness of 2 nm or less/light emitting layer/cathode r) anode/light emitting layer/insulation layer having a thickness of 2 nm or less/cathode s) anode/insulation layer having a thickness of 2 nm or less/light emitting layer/insulation layer having a thickness of 2 nm or less/cathode t) anode/insulation layer having a thickness of 2 nm or less/hole transporting layer/light emitting layer/cathode u) anode/hole transporting layer/light emitting layer/insulation layer having a thickness of 2 nm or less/cathode v) anode/insulation layer having a thickness of 2 nm or less/hole transporting layer/light emitting layer/insulation layer having a thickness of 2 nm or less/cathode w) anode/insulation layer having a thickness of 2 nm or less/light emitting layer/electron transporting layer/cathode x) anode/light emitting layer/electron transporting layer/insulation layer having a thickness of 2 nm or less/cathode y) anode/insulation layer having a thickness of 2 nm or less/light emitting layer/electron transporting layer/insulation layer having a thickness of 2 nm or less/cathode z) anode/insulation layer having a thickness of 2 nm or less/hole transporting layer/light emitting layer/electron transporting layer/cathode aa) anode/hole transporting layer/light emitting layer/electron transporting layer/insulation layer having a thickness of 2 nm or less/cathode ab) anode/insulation layer having a thickness of 2 nm or less/hole transporting layer/light emitting layer/electron transporting layer/insulation layer having a thickness of 2 nm or less/cathode In producing a polymer LED, when a film is formed from a solution by using such polymeric fluorescent substance soluble in an organic solvent, only required is removal of the solvent by drying after coating of this solution, and even in the case of mixing of a charge transporting material and a light emitting material, the same method can be applied, causing an extreme advantage in production. As the film forming method from a solution, there can be used coating methods such as a spin coating method, casting method, micro gravure coating method, gravure coating method, bar coating method, roll coating method, wire bar coating method, dip coating method, spray coating method, screen printing method, flexo printing method, offset printing method, inkjet printing method and the like.

Regarding the thickness of the light emitting layer, the optimum value differs depending on material used, and may properly be selected so that the driving voltage and the light emitting efficiency become optimum values, and for example, it is from 1 nm to 1 μm, preferably from 2 nm to 500 nm, further preferably from 5 nm to 200 nm.

In the polymer LED of the present invention, light emitting materials other than the above-described polymeric fluorescent substance can also be mixed in a light emitting layer. Further, in the polymer LED of the present invention, the light emitting layer containing light emitting materials other than the above-described polymeric fluorescent substance may also be laminated with a light emitting layer containing the above-described polymeric fluorescent substance.

As the light emitting material, known materials can be used. In a compound having lower molecular weight, there can be used, for example, naphthalene derivatives, anthracene or derivatives thereof, perylene or derivatives thereof; dyes such as polymethine dyes, xanthene dyes, coumarine dyes, cyanine dyes; metal complexes of 8-hydroxyquinoline or derivatives thereof, aromatic amine, tetraphenylcyclopentane or derivatives thereof, or tetraphenylbutadiene or derivatives thereof, and the like.

Specifically, there can be used known compounds such as those described in JP-A Nos. 57-51781, 59-195393 and the like, for example.

When the polymer LED of the present invention has a hole transporting layer, as the hole transporting materials used, there are exemplified polyvinylcarbazole or derivatives thereof, polysilane or derivatives thereof, polysiloxane derivatives having an aromatic amine in the side chain or the main chain, pyrazoline derivatives, arylamine derivatives, stilbene derivatives, triphenyldiamine derivatives, polyaniline or derivatives thereof, polythiophene or derivatives thereof, polypyrrole or derivatives thereof, poly(p-phenylenevinylene) or derivatives thereof, poly(2,5-thienylenevinylene) or derivatives thereof, or the like.

Specific examples of the hole transporting material include those described in JP-A Nos. 63-70257, 63-175860, 2-135359, 2-135361, 2-209988, 3-37992 and 3-152184.

Among them, as the hole transporting materials used in the hole transporting layer, preferable are polymer hole transporting materials such as polyvinylcarbazole or derivatives thereof, polysilane or derivatives thereof, polysiloxane derivatives having an aromatic amine compound group in the side chain or the main chain, polyaniline or derivatives thereof, polythiophene or derivatives thereof, poly(p-phenylenevinylene) or derivatives thereof, poly(2,5-thienylenevinylene) or derivatives thereof, or the like, and further preferable are polyvinylcarbazole or derivatives thereof, polysilane or derivatives thereof and polysiloxane derivatives having an aromatic amine compound group in the side chain or the main chain. In the case of a hole transporting material having lower molecular weight, it is preferably dispersed in a polymer binder for use.

Polyvinylcarbazole or derivatives thereof are obtained, for example, by cation polymerization or radical polymerization from a vinyl monomer.

As the polysilane or derivatives thereof, there are exemplified compounds described in Chem. Rev., 89, 1359 (1989) and GB 2300196 published specification, and the like. For synthesis, methods described in them can be used, and a Kipping method can be suitably used particularly.

As the polysiloxane or derivatives thereof, those having the structure of the above-described hole transporting material having lower molecular weight in the side chain or main chain, since the siloxane skeleton structure has poor hole transporting property. Particularly, there are exemplified those having an aromatic amine having hole transporting property in the side chain or main chain.

The method for forming a hole transporting layer is not restricted, and in the case of a hole transporting layer having lower molecular weight, a method in which the layer is formed from a mixed solution with a polymer binder is exemplified. In the case of a polymer hole transporting material, a method in which the layer is formed from a solution is exemplified.

The solvent used for the film forming from a solution is not particularly restricted providing it can dissolve a hole transporting material. As the solvent, there are exemplified chlorine solvents such as chloroform, methylene chloride, dichloroethane and the like, ether solvents such as tetrahydrofuran and the like, aromatic hydrocarbon solvents such as toluene, xylene and the like, ketone solvents such as acetone, methyl ethyl ketone and the like, and ester solvents such as ethyl acetate, butyl acetate, ethylcellosolve acetate and the like.

As the film forming method from a solution, there can be used coating methods such as a spin coating method, casting method, micro gravure coating method, gravure coating method, bar coating method, roll coating method, wire bar coating method, dip coating method, spray coating method, screen printing method, flexo printing method, offset printing method, inkjet printing method and the like, from a solution.

The polymer binder mixed is preferably that does not disturb charge transport extremely, and that does not have strong absorption of a visible light is suitably used. As such polymer binder, polycarbonate, polyacrylate, poly(methyl acrylate), poly(methyl methacrylate), polystyrene, polyvinyl chloride), polysiloxane and the like are exemplified.

Regarding the thickness of the hole transporting layer, the optimum value differs depending on material used, and may properly be selected so that the driving voltage and the light emitting efficiency become optimum values, and at least a thickness at which no pin hole is produced is necessary, and too large thickness is not preferable since the driving voltage of the device increases. Therefore, the thickness of the hole transporting layer is, for example, from 1 nm to 1 μm, preferably from 2 nm to 500 nm, further preferably from 5 nm to 200 nm.

When the polymer LED of the present invention has an electron transporting layer, known compounds are used as the electron transporting materials, and there are exemplified oxadiazole derivatives, anthraquinonedimethane or derivatives thereof, benzoquinone or derivatives thereof, naphthoquinone or derivatives thereof, anthraquinone or derivatives thereof, tetracyanoanthraquinodimethane or derivatives thereof, fluorenone derivatives, diphenyldicyanoethylene or derivatives thereof, diphenoquinone derivatives, or metal complexes of 8-hydroxyquinoline or derivatives thereof, polyquinoline and derivatives thereof, polyquinoxaline and derivatives thereof, polyfluorene or derivatives thereof, and the like.

Specifically, there are exemplified those described in JP-A Nos. 63-70257, 63-175860, 2-135359, 2-135361, 2-209988, 3-37992 and 3-152184.

Among them, oxadiazole derivatives, benzoquinone or derivatives thereof, anthraquinone or derivatives thereof, or metal complexes of 8-hydroxyquinoline or derivatives thereof, polyquinoline and derivatives thereof, polyquinoxaline and derivatives thereof, polyfluorene or derivatives thereof are preferable, and 2-(4-biphenyl)-5-(4-t-butylphenyl)-1,3,4-oxadiazole, benzoquinone, anthraquinone, tris(8-quinolinol)aluminum and polyquinoline are further preferable.

The method for forming the electron transporting layer is not particularly restricted, and in the case of an electron transporting material having lower molecular weight, a vapor deposition method from a powder, or a method of film-forming from a solution or melted state is exemplified, and in the case of a polymer electron transporting material, a method of film-forming from a solution or melted state is exemplified, respectively.

The solvent used in the film-forming from a solution is not particularly restricted provided it can dissolve electron transporting materials and/or polymer binders. As the solvent, there are exemplified chlorine solvents such as chloroform, methylene chloride, dichloroethane and the like, ether solvents such as tetrahydrofuran and the like, aromatic hydrocarbon solvents such as toluene, xylene and the like, ketone solvents such as acetone, methyl ethyl ketone and the like, and ester solvents such as ethyl acetate, butyl acetate, ethylcellosolve acetate and the like.

As the film-forming method from a solution or melted state, there can be used coating methods such as a spin coating method, casting method, micro gravure coating method, gravure coating method, bar coating method, roll coating method, wire bar coating method, dip coating method, spray coating method, screen printing method, flexo printing method, offset printing method, inkjet printing method and the like.

The polymer binder to be mixed is preferably that which does not extremely disturb a charge transport property, and that does not have strong absorption of a visible light is suitably used. As such polymer binder, poly(N-vinylcarbazole), polyaniline or derivatives thereof, polythiophene or derivatives thereof, poly(p-phenylene vinylene) or derivatives thereof, poly(2,5-thienylene vinylene) or derivatives thereof, polycarbonate, polyacrylate, poly(methyl acrylate), poly(methyl methacrylate), polystyrene, polyvinyl chloride), polysiloxane and the like are exemplified.

Regarding the thickness of the electron transporting layer, the optimum value differs depending on material used, and may properly be selected so that the driving voltage and the light emitting efficiency become optimum values, and at least a thickness at which no pin hole is produced is necessary, and too large thickness is not preferable since the driving voltage of the device increases. Therefore, the thickness of the electron transporting layer is, for example, from 1 nm to 1 µm, preferably from 2 nm to 500 nm, further preferably from 5 nm to 200 nm.

The substrate forming the polymer LED of the present invention may preferably be that does not change in forming an electrode and layers of organic materials, and there are exemplified glass, plastics, polymer film, silicon substrates and the like. In the case of a opaque substrate, it is preferable that the opposite electrode is transparent or semitransparent.

At least one of the electrodes consisting of an anode and a cathode, is transparent or semitransparent. It is preferable that the anode is transparent or semitransparent.

As the material of this anode, electron conductive metal oxide films, semitransparent metal thin films and the like are used. Specifically, there are used indium oxide, zinc oxide, tin oxide, and films (NESA and the like) fabricated by using an electron conductive glass composed of indium/tin/oxide (ITO), indium/zinc/oxide and the like, which are metal oxide complexes, and gold, platinum, silver, copper and the like are used, and among them, ITO, indium/zinc/oxide, tin oxide are preferable. As the fabricating method, a vacuum vapor deposition method, sputtering method, ion plating method, plating method and the like are used. As the anode, there may also be used organic transparent conducting films such as polyaniline or derivatives thereof, polythiophene or derivatives thereof and the like.

The thickness of the anode can be appropriately selected while considering transmission of a light and electric conductivity, and for example, from 10 nm to 10 µm, preferably from 20 nm to 1 µm, further preferably from 50 nm to 500 nm.

Further, for easy charge injection, there may be provided on the anode a layer comprising a phthalocyanine derivative conducting polymers, carbon and the like, or a layer having an average film thickness of 2 nm or less comprising a metal oxide, metal fluoride, organic insulating material and the like.

As the material of a cathode used in the polymer LED of the present invention, that having lower work function is preferable. For example, there are used metals such as lithium, sodium, potassium, rubidium, cesium, beryllium, magnesium, calcium, strontium, barium, aluminum, scandium, vanadium, zinc, yttrium, indium, cerium, samarium, europium, terbium, ytterbium and the like, or alloys comprising two of more of them, or alloys comprising one or more of them with one or more of gold, silver, platinum, copper, manganese, titanium, cobalt, nickel, tungsten and tin, graphite or graphite intercalation compounds and the like. Examples of alloys include a magnesium-silver alloy, magnesium-indium alloy, magnesium-aluminum alloy, indium-silver alloy, lithium-aluminum alloy, lithium-magnesium alloy, lithium-indium alloy, calcium-aluminum alloy and the like. The cathode may be formed into a laminated structure of two or more layers.

The thickness of the cathode can be appropriately selected while considering transmission of a light and electric conductivity, and for example, from 10 nm to 10 µm, preferably from 20 nm to 1 µm, further preferably from 50 nm to 500 nm.

As the method for fabricating a cathode, there are used a vacuum vapor deposition method, sputtering method, lamination method in which a metal thin film is adhered under heat and pressure, and the like. Further, there may also be provided, between a cathode and an organic layer, a layer comprising an conducting polymer, or a layer having an average film thickness of 2 nm or less comprising a metal oxide, metal fluoride, organic insulation material and the like, and after fabrication of the cathode, a protective layer may also be provided which protects the polymer LED. For stable use of the polymer LED for a long period of time, it is preferable to provide a protective layer and/or protective cover for protection of the device in order to prevent it from outside damage.

As the protective layer, there can be used a polymeric compound, metal oxide, metal fluoride, metal borate and the like. As the protective cover, there can be used a glass plate, a plastic plate the surface of which has been subjected to lower-water-permeation treatment, and the like, and there is suitably used a method in which the cover is pasted with an device substrate by a thermosetting resin or light-curing resin for sealing. If space is maintained using a spacer, it is easy to prevent an device from being injured. If an inner gas such as nitrogen and argon is sealed in this space, it is possible to prevent oxidation of a cathode, and further, by placing a desiccant such as barium oxide and the like in the above-described space, it is easy to suppress the damage of an device by moisture adhered in the production process. Among them, any one means or more are preferably adopted.

The polymer LED of the present invention can be used for a flat light source, a segment display, a dot matrix display, and a liquid crystal display as a back light, etc.

For obtaining light emission in plane form using the polymer LED of the present invention, an anode and a cathode in the plane form may properly be placed so that they are laminated each other. Further, for obtaining light emission in pattern form, there is a method in which a mask with a window in pattern form is placed on the above-described plane light emitting device, a method in which an organic layer in non-light emission part is formed to obtain extremely large thickness providing substantial non-light emission, and a method in which any one of an anode or a cathode, or both of them are formed in the pattern. By forming a pattern by any of these methods and by placing some electrodes so that independent on/off is possible, there is obtained a display device of segment type which can display digits, letters, simple marks and the like. Further, for forming a dot matrix device, it may be advantageous that anodes and cathodes are made in the form of stripes and placed so that they cross at right angles. By a method in which a plurality of kinds of polymeric compounds emitting different colors of lights are placed separately or a method in which a color filter or luminescence converting filter is used, area color displays and multi color displays are obtained. A dot matrix display can be driven by passive driving, or by active driving combined with TFT and the like. These display devices can be used as a display of a computer, television, portable terminal, portable telephone, car navigation, view finder of a video camera, and the like.

Further, the above-described light emitting device in plane form is a thin self-light-emitting one, and can be suitably used as a flat light source for back-light of a liquid crystal display, or as a flat light source for illumination. Further, if a flexible plate is used, it can also be used as a curved light source or a display.

The polymeric light-emitting substance of the present invention has triplet light-emitting complex structure in a molecule, and can form a light emitting layer by industrially simple application methods, such as a spin coat method, an inkjet method, and a printing method. Moreover, the polymeric light-emitting substance of the present invention contains triplet light-emitting complex, and can show high light emitting efficiency. Therefore, the polymeric light-emitting substance of the present invention can be used preferably for light-emitting materials of polymer LED etc.

Hereafter, in order to explain the present invention in detail with showing examples, but the present invention is not limited to these.

Here, about the number average molecular weight and the weight average molecular weight, the polystyrene reduced number average molecular weight and the weight average molecular weight were obtained by gel permeation chromatography (GPC), using chloroform as a solvent.

Synthesis of Monomer A-1

1.55 g of phosphonate obtained by reacting 1,4-dibromo-2,5-bis(bromomethyl)-benzene and phosphoric-acid triethyl, and 1.79 g of N-ethyl-3-carbazole carboxy aldehyde were dissolved in 30 g of tetrahydrofuran (dehydrated). After adding a solution in which 0.9 g of potassium-t-butoxide was dissolved beforehand in 10 g of tetrahydrofuran (dehydrated) dropwise into this solution at room temperature, it was succeedingly reacted at room temperature for 5 hours.

After the reaction, this solution was neutralized with adding acetic acid, then methanol was added to this solution and resulting precipitation was collected by filtration. The collected precipitation was washed with ethanol, and dried under reduced-pressure and 1.5 g of a crude product was obtained. Next, it was re-crystallized from chloroform and purified monomer A was obtained.

$^1$H-NMR (200 MHz, CDCl$_3$)

δ 8.24 (2H, brs), 8.14 (2H, d), 7.93 (2H, s), 7.71 (2H, d), 7.52 (12H, m), 4.37 (4H, q), 1.45 (6H, t)

A-1

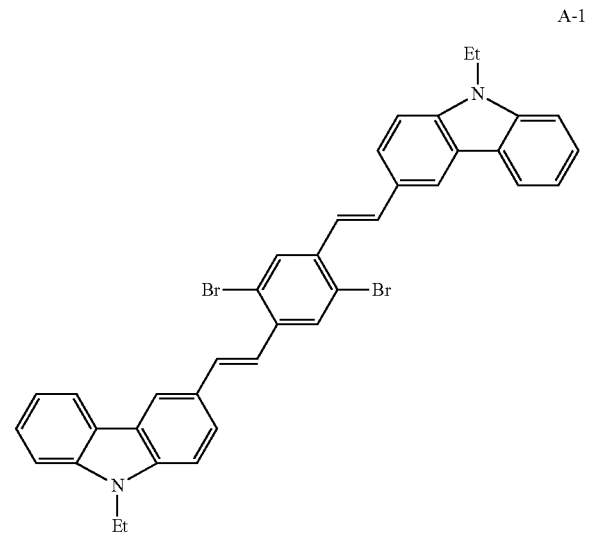 [SMILES: CCn1c2ccccc2c2cc(/C=C/c3cc(Br)c(/C=C/c4ccc5c(c4)c4ccccc4n5CC)cc3Br)ccc21]

Synthesis of Monomer A-2

Synthesis of 2-(bromophenyl)pyridine 3 g (19.3 mmol) of 2-phenyl pyridine and 40 mg (0.716 mmol) of iron powder were mixed and stirred. It was cooled to 0° C. and 4.0 g (25 mmol) of bromine was added dropwise with stirring, and watching heat generation, and it was raised to 90° C., and stirred for 10 hours. After the reaction, this reaction mixture was dissolved in chloroform to produce a solution, which was washed with 5% sodium thiosulfate aqueous solution. The chloroform solution was dried with sodium sulfate, and then concentrated. The residue was purified by silica gel column chromatography, and the desired 2-(bromophenyl)pyridine was obtained.

The amount was 1.6 g (6.83 mmol), and the yield was 35.4%. By LC-MS, M+ was 234.0.

Synthesis of tris(2-(bromophenyl)pyridine) iridium (III)

50 mg (0.1021 mmol) of trisacetylacetonate iridium (III) complex, 95.6 mg (0.4084 mmol) of 2-bromophenyl pyridine, and 20 ml of glycol were charged into a 50 ml eggplant type flask, and refluxed for 10 hours. 100 ml of 1 N hydrogen chloride aqueous solution was added to this reaction solution, and stirred for 30 minutes. The deposited solid was filtrated, and dissolved again in a small amount of methylene chloride to produce a solution. This solution was filtrated with silica gel column chromatography, and the residual metal decomposition material originated from the iridium complex was removed. Then, obtained solution was concentrated partway, and the yellow solid deposited by addition of methanol was filtrated and collected.

The desired product of tris(2-(bromophenyl)pyridine) iridium (III) 10.12 mg (0.0113 mmol) was obtained. The yield was 11.1%. By FD-MS, M+ was 893.

Synthesis of bis 2-(phenyl)pyridine)mono(2-(bromophenyl)pyridine)iridium (III) (monomer A-2)

0.642 g (1.31 mmol) of trisacetylacetonate iridium (III) complex, 0.41 g (1.75 mmol) of 2-(bromophenyl)pyridine, 0.54 g (3.5 mmol) of 2-(phenyl)pyridine, and 50 ml of glycol was supplied to were charged into a 100 ml eggplant type flask, and refluxed for 10 hours. 100 ml of 1 N hydrogen chloride aqueous solution was added to this reaction solution, and stirred for 30 minutes. The deposited solid was filtrated, and dissolved again in a small amount of methylene chloride to produce a solution. This solution was filtrated with silica gel column chromatography, and the residual metal decomposition material originated from the iridium complex was removed. Then, obtained solution was concentrated partway, and the yellow solid deposited by addition of methanol was filtrated and collected.

A mixture of bis(2-(phenyl)pyridine)mono(2-(bromophenyl)pyridine) iridium (III) as the main component was obtained, 0.13 g (0.177 mmol equivalent). The yield was about 13.5%. By FD-MS, M+ of the main component was 733. The mixture is a mixture of a tris(2-(bromophenyl)pyridine) iridium (III) complex (complex 4), mono(2-(phenyl)pyridine)bis(2-(bromophenyl)pyridine) iridium (III) complex (complex 3), bis(2-(phenyl)pyridine)mono(2-(bromo phenyl)pyridine) iridium (III) complex (complex 2), and tris (2-(phenyl)pyridine) iridium (III) complex (complex 1). Each ratios by FD-MS, are represented in below Table 1.

TABLE 1

| | Peak ratio | Composition ratio (%) | Note |
|---|---|---|---|
| Composition of monomer A-2 (mixture) FD-MS of complex | | | |
| Complex 1 | 31 | 12.2 | React to the end of the molecule which is discharged without reaction |
| Complex 2 | 86 | 33.7 | |
| Complex 3 | 100 | 39.2 | |
| Complex 4 | 38 | 14.9 | |

Synthesis of Polymer A 0.40 g (0.73 mmol) of 9,9-dioctyl-2,7-dibromo fluorene, 0.044 g (0.065 mmol) of monomer A-1, 0.012 g (0.016 mmol) of monomer A-2, and 0.30 g (1.9 mmol) of 2,2'-bipyridyl were charged into a reaction vessel, and then the inside of the reaction system was replaced with nitrogen gas. Into this, 20 ml of tetrahydrofuran (dehydrated solvent) which was deaerated with argon gas bubbling beforehand was added.

Next, 0.54 g (1.9 mmol) of bis(1,5-cyclooctadiene) nickel (0) was added to this mixed solution, and it was reacted at 60° C. for 3 hours. The reaction was conducted in nitrogen-gas atmosphere. After the reaction, this solution was cooled, and poured into a mixed solution of 25% aqueous ammonia 10 ml/methanol 120 ml/ion-exchanged water 50 ml, and stirred for about 1 hour. Next, the resulting precipitation was collected by filtration. This precipitation was washed with ethanol, and then dried under reduced-pressure for 2 hours. Next, this precipitation is dissolved in toluene 30 mL, 1N hydrogen chloride 30 mL is added to it, and stirred for 1 hour, and the aqueous layer was removed. 4% aqueous ammonia 30 mL was added to the organic layer, and the aqueous layer was removed after stirring for 1 hour. The organic layer was added dropwise into methanol 150 mL, and stirred for 1 hour, and the deposited precipite was filtrated and dried under reduced-pressure for 2 hours, and then it was dissolved in toluene 30 mL. Then, it was purified by passing through alumina column (alumina 20 g), the collected toluene solution was added to methanol 150 mL and stirred for 1 hour, the deposited precipitate was filtrated and dried under reduced-pressure for 2 hours. The yield of obtained copolymer was 0.14 g.

The polystyrene reduced number average molecular weight of the copolymer was $9.2 \times 10^4$, and the polystyrene reduced weight average molecular weight was $3.9 \times 10^5$.

Synthesis of Complex B

Synthesis of 1-bromo-3-trifluoromethyl sulfonyloxy benzene 12.1 g of 3-bromophenol, 12.8 g of 4-dimethylpyridine, and 50 ml of methylenechloride were charged into a four-necked flask under argon atmosphere. It was cooled with an ice bath, and 30 ml of methylene chloride solution of trifluoromethanesulfonic acid anhydride 24.7 g was added dropwise with ice bath cooling, for about 1 hour. The temperature was raised to room temperature by being left as it was, it was reacted at room temperature for 5 hours. The reaction mass was charged to silica gel and developed with toluene. The filtrate was concentrated and 20.4 g of a mixture containing 1-bromo-3-trifluoromethyl sulfonyloxy benzene was obtained.

Synthesis of 1-bromo-3-(2-thienyl)benzene 2.2 g of lithium bromide was charged into a four-necked flask under argon atmosphere, and dried with heating under reduced pressure. Subsequently, under argon atmosphere, diethyl ether 10 ml was charged. Furthermore, 9.9 g of a mixture containing 1-bromo-3-trifluoromethyl sulfonyloxybenzene and 0.72 g of [1,2-bis(diphenylphosphino)ethane] palladium (II) dichloride were charged, and it was cooled with an ice bath. 45 ml diethyl ether solution of 2-thienyl magnesium bromide (37.5 mmol) prepared by ordinary method, was added dropwise for about 10 minutes with ice bath cooling, and it was reacted for 6 hours.

The reaction mass was charged to silica gel and developed with chloroform. The filtrate was concentrated and a reaction mixture was obtained. It was purified with silica gel column (eluent: cyclohexane/toluene=40/1), and 1.96 g of a mixture containing 1-bromo-3-(2-thienyl)benzene was obtained.

Synthesis of N-3-(2-thienyl)phenylcarbazole)

Under argon atmosphere, 1.0 g of carbazole, 1.75 g of a mixture containing 1-bromo-3-(2-thienyl)-benzene, 0.08 g of tris(dibenzylidineacetone)dipalladium(0), 0.86 g of sodium tert-butoxide, and 5 ml of toluene and 0.06 g of tri(tert-butyl) phosphine were charged, and the temperature was raised to 100° C. It was reacted at 100° C., for 9 hours. 0.04 g of tris(dibenzylidineacetone)dipalladium(0) and 0.03 g of tri (tert-butyl)phosphine were added, and further reacted at 100° C., for 8 hours. Toluene 100 ml was added to the reaction mass, and washed and partitioned by 30 ml of ion-exchanged water 2 times. The organic layer was dried with anhydrous sodium sulfate, then filtrated and concentrated, and a reaction mixture was obtained. It was purified with silica gel column (eluent: cyclohexane/toluene=6/1), and 1.61 g of N-3-(2-thienyl)phenylcarbazole was obtained.

LC/MS: APCI method [M+H]+=326

Synthesis of Ligand B

Under argon atmosphere, N-3-(2-thienyl)phenylcarbazole (2.5 mmol, 0.81 g) and diethyl ether (5 ml) were charged into a four-necked flask. It was cooled with methanol/ice and n-butyl lithium (1.6M hexane solution) (2.3 ml) was added dropwise for about 5 minutes.

The temperature was raised to room temperature by being left as it was, and stirred for 10 minutes, then diethylether solution (0.5 ml) of 2-fluoropyridine (2.5 mmol, 0.24 g) was added dropwise for about 5 minutes. Then, the reaction was carried out with refluxing for 2 hours. After it was cooled to room temperature by being left as it was, 200 ml of toluene and 50 ml of ion-exchanged water were added and partitioned. The organic layer was dried with anhydrous sodium sulfate, filtrated and concentrated, and a reaction mixture was obtained. It was purified with silica gel column (eluent: cyclohexane/toluene=6/1), and 0.16 g of ligand B was obtained.

$^1$H-NMR (300 MHz, CDCl$_3$)

δ 8.58 (1H, d), 8.16 (2H, d), 7.89 (1H, brs), 7.76 (1H, d), 7.70 to 7.14 (13H, m)

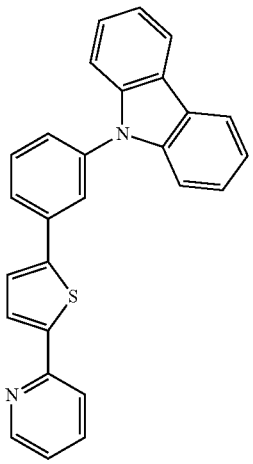

Ligand B

Synthesis of Complex B 57.3 mg of ligand B synthesized above, 17.4 mg of iridium (III) acetylacetonate, 10 ml of glycerol were charged, and replaced with argon. The temperature was raised to 200° C., for 1 hour, and was kept warm for 8 hours. After standing to cool to room temperature, it was added into 1N hydrogen chloride aqueous solution (30 ml), and the deposit was filtrated. The deposit was dissolved in a small amount of methylene chloride, and filtrated with silica gel column (eluent: methylene chloride). Obtained solution was concentrated and 13.7 mg of light orange crystal was obtained. By FD/MS measurement, molecule ion peak of complex B was detected.

FD/MS: 1397 [M+]

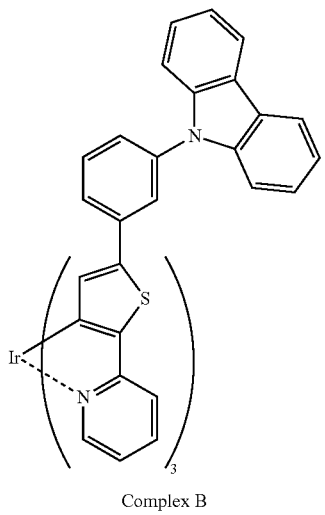

Complex B

Synthesis of Complex C

N-ethyl-3-bromocarbazole 5.00 g of N-ethylcarbazole was dissolved in 130 ml of dehydrated DMF in a flask whose atmosphere was replaced with argon. This solution was cooled to 0° C., 4.60 g of N-bromosuccinimide was charged as 5 divided fractions for 3 hours. After raising the temperature to room temperature and stirring for 12 hours, the reaction liquid was thrown into iced water and filtrated. The residue was washed with water and methanol, and dried under reduced-pressure to give 6.28 g crude product. It was purified with silica gel column chromatography (eluent: cyclohexane containing 0.1% triethylamine), and 5.68 g of N-ethyl-3-bromo carbazole was obtained.

$^1$H-NMR (300 MHz, CDCl$_3$)

δ 8.17 (1H, brs), 8.01 (1H, dd), 7.50 (1H, dd), 7.46 (1H, d), 7.35 (1H, d), 7.24 to 7.17 (2H, m), 4.26 (2H, q), 1.39 (3H, t)

MS (APCI, psitive)

m/z: 274, 276 [M+H]+

N-ethyl-3-(3-trifluoromethanesulfonyloxyphenyl) carbazole 1.00 g of N-ethyl-3-bromocarbazole was dissolved in 3.2 ml of dehydrated ether in a Schrenck tube which was flame-dried and argon gas-replaced. This solution was cooled to −78° C., and 2.4 ml of n-butyl lithium (2.64M hexane solution) was added dropwise. After raising the temperature to 0° C., and stirring for 1 hour, it was cooled again to −78° C., an ether solution of magnesium bromide prepared from magnesium 0.4 g and 1,2-dibromoethane 0.8 g was added dropwise. After raising the temperature to room temperature and stirring for 12 hours, this reaction solution was added dropwise into a solution which was prepared by suspending lithium bromide 0.28 g, 3-trifluoromethanesulfoxybromo benzene 0.82 g, and dichloro[1,3-bis(diphenylphosphino)propane] palladium(II) 0.09 g in dehydrated diethylether 2 ml, and cooled at 0° C. After stirring for 7 hours, 20 ml water was added dropwise and partitioned. The aqueous phase was extracted twice with 40 ml toluene, and the combined aqueous phase was washed with water and saturated NaCl aqueous solution, then concentrated, and 1.61 g of crude product was obtained. It was purified with silica gel column chromatography (eluent, hexane:ethyl-acetate=25:1), 0.33 g of N-ethyl-3-(3-bromophenyl)carbazole was obtained.

$^1$H-NMR (CDCl$_3$, 300 MHz)

δ 8.28 (1H, brs), 8.17 (1H, dd), 7.86 (1H, brs), 7.68 to 7.61 (2H, m), 7.52 to 7.16 (6H, m), 4.39 (2H, q), 1.45 (3H, t)

MS (APCI, psitive)

m/z: 350, 352 [M+H]+

Synthesis of Ligand C 0.30 g of N-ethyl-3-(3-bromophenyl)carbazole was dissolved in 0.9 ml dehydrated diethylether in a Schrenck tube which was flame-dried and argon gas-replaced, and it was cooled to −78° C.

After adding dropwise 0.4 ml (2.64M hexane solution) of n-butyl lithium into this solution, the temperature was raised to −10° C., and stirred for 1 hour, and cooled to −78° C., again. To this solution, a solution prepared by dissolving 0.08 g of 2-fluoro pyridine in 0.9 ml of dehydrated diethylether was added dropwise. The temperature was raised gradually to room temperature, and it was stirred for 12 hours, then partitioned with adding 5 ml of water. The aqueous phase was extracted 3 times with 5 ml toluene, and the combined organic phase was concentrated to give 0.39 g crude product.

MS (APCI, psitive)

m/z: 349 [M+H]+

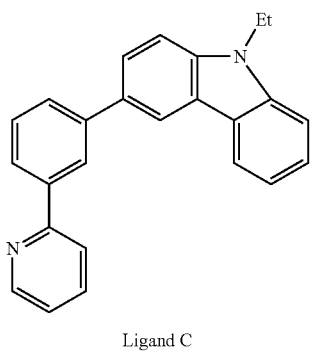 [SMILES: CCn1c2ccccc2c2cc(-c3cccc(-c4ccccn4)c3)ccc21]

Ligand C

Synthesis of Complex C

Complex C can be prepared by using ligand C instead of ligand B in the synthesis of the above complex B.

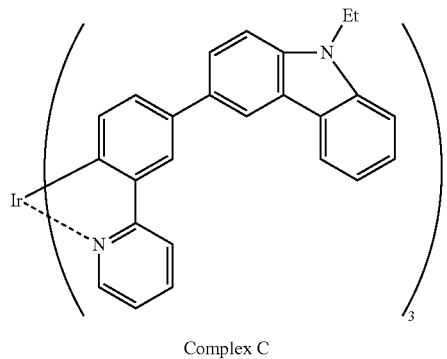

Complex C

<Measurement of Light Emission Strength>

A thin film was prepared by spin coating 0.2 wt % chloroform solution of the above polymeric light-emitting substance A on quartz. The light emission spectrum of this thin film was measured using a fluorospectrophotometer (produced by JOBIN YVON/SPEX Co., FL3-221 TAU fluorospectrophotometer). For calculation of light emission strength, the light emission spectrum excited at 350 nm was used. The relative value of light emission strength was determined by dividing the area of light emission spectrum which was plotted on wave number as abscissas by the absorbance at 350 nm. The measurement result is shown below.

Light Emission Strength

| Light Emission Wavelength (nm) | Relative Strength |
| --- | --- |
| 450 | 1.97 |
| 476 | 1.78 |
| 523 | 1.67 |

The invention claimed is:

1. A polymeric light-emitting substance wherein said light-emitting substance has an iridium complex structure showing light emission from triplet excited state in the main chain or side chain, and has a monovalent group represented by the following general formula (1) or (2):

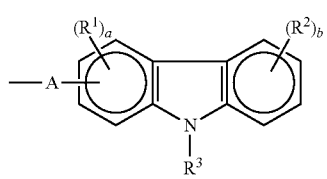

(1)

wherein A is a single bond or a divalent group derived from conjugate system, $R^1$ and $R^2$ each independently represent a halogen atom, alkyl group, alkoxy group, alkylthio group, alkylamino group, alkylsilyl group, aryl group, aryloxy group, arylthio group, arylamino group, arylsilyl group, arylalkyl group, arylalkoxy group, arylalkylthio group, arylalkylamino group, arylalkyl silyl group, acyl group, acyloxy group, imino group, amide group, arylalkenyl group, arylalkynyl group, cyano group, or a monovalent heterocyclic group, $R^3$ represents alkyl group, aryl group, arylalkyl group, arylalkenyl group, arylalkynyl group, or a monovalent heterocyclic group, a represents an integer of 0 to 3, b represents an integer of 0 to 4, and when a is two or more, a plurality of $R^1$s may be the same or different and when b is two or more, a plurality of $R^2$s may be the same or different;

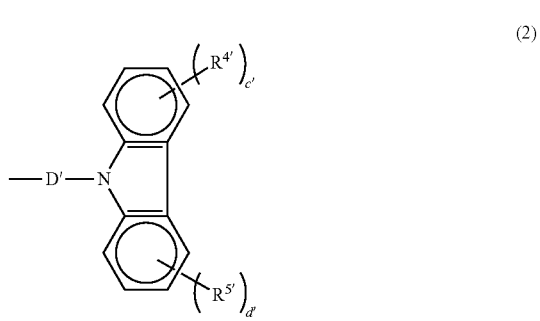

(2)

wherein D is a single bond or a divalent group derived from conjugate system, $R^4$ and $R^5$ each independently represent a halogen atom, alkyl group, alkoxy group, alkylthio group, alkylamino group, alkylsilyl group, aryl group, aryloxy group, arylthio group, arylamino group, arylsilyl group, arylalkyl group, arylalkoxy group, arylalkylthio group, arylalkylamino group, arylalkylsilyl group, acyl group, acyloxy group, imino group, amide group, arylalkenyl group, arylalkynyl group, cyano group, or a monovalent heterocyclic group, c and d each independently represent an integer of 0 to 4, and when c is two or more, a plurality of $R^4$s may be the same or different; when d is two or more, a plurality of $R^5$s may be the same or different;

wherein the main chain of said light-emitting substance is a conjugated type polymeric light-emitting substance, and contains a repeating unit represented by the following general formula (14),

(14)

wherein $Ar^6$ represents an arylene group or a divalent heterocyclic group, n is 0 or 1, R$^{20}$ and R$^{21}$ each independently represent a hydrogen atom, alkyl group, aryl group, arylalkyl group, arylalkenyl group, arylalkynyl group, monovalent heterocyclic group, or cyano group, and at least one of R$^{20}$, R$^{21}$, or a substituent on Ar$^6$, represents a group represented by the above formula (1) or (2).

2. A polymeric light-emitting substance according to claim 1, wherein at least one ligand of the iridium complex portion showing light emission from triplet excited state bonds to a metal through a nitrogen atom and/or a carbon atom.

3. A polymeric light-emitting substance according to claim 1 wherein at least one ligand of the iridium complex portion showing light emission from triplet excited state is a multi-dentate ligand.

4. A polymeric light-emitting substance according to claim 1 wherein at least one ligand of the iridium complex portion showing light emission from triplet excited state is a monovalent bi-dentate ligand represented by the below formula (15) or (16),

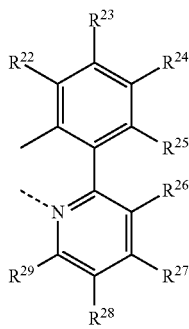

(15)

wherein R$^{22}$ to R$^{29}$ each independently represent a hydrogen atom, halogen atom, alkyl group, alkoxy group, alkylthio group, alkylamino group, alkylsilyl group, aryl group, aryloxy group, arylthio group, arylamino group, aryl silyl group, arylalkyl group, arylalkoxy group, arylalkylthio group, arylalkylamino group, arylalkylsilyl group, acyl group, acyloxy group, imino group, amide group, arylalkenyl group, arylalkynyl group, cyano group, or monovalent heterocyclic group, and at least one of R$^{22}$ to R$^{29}$ is a bond with a main chain or a side chain;

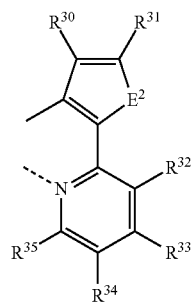

(16)

wherein E$^2$ represents an oxygen atom or a sulfur atom,

R$^{30}$ to R$^{35}$ each independently represent a hydrogen atom, halogen atom, alkyl group, alkoxy group, alkylthio group, alkylamino group, alkylsilyl group, aryl group, aryloxy group, arylthio group, arylamino group, arylsilyl group, arylalkyl group, aryl alkoxy group, arylalkylthio group, arylalkylamino group, arylalkylsilyl group, acyl group, acyloxy group, imino group, amide group, arylalkenyl group, arylalkynyl group, cyano group, or monovalent heterocyclic group, and at least one of R$^{30}$ to R$^{35}$ is a bond with a main chain or a side chain.

5. An organic electroluminescent device comprising a layer which contains the polymeric light-emitting substance according to claim 1 between electrodes consisting of an anode and a cathode.

* * * * *